(12) United States Patent
Decurtins et al.

(10) Patent No.: US 10,240,147 B2
(45) Date of Patent: Mar. 26, 2019

(54) PRODUCTION OF ENCODED CHEMICAL LIBRARIES

(71) Applicant: Philochem AG, Otelfingen (CH)

(72) Inventors: Willy Decurtins, Horgen (CH); Raphael Franzini, Zürich (CH); Dario Neri, Buchs (CH); Jörg Scheuermann, Wurenlos (CH); Moreno Wichert, Wangen-Nuolen (CH)

(73) Assignee: PHILOCHEM AG, Otelfingen (CH)

( * ) Notice: Subject to any disclaimer, the term of this patent is extended or adjusted under 35 U.S.C. 154(b) by 355 days.

(21) Appl. No.: 15/106,795

(22) PCT Filed: Dec. 11, 2014

(86) PCT No.: PCT/EP2014/077403
§ 371 (c)(1),
(2) Date: Jun. 20, 2016

(87) PCT Pub. No.: WO2015/091207
PCT Pub. Date: Jun. 25, 2015

(65) Prior Publication Data
US 2017/0009226 A1    Jan. 12, 2017

(30) Foreign Application Priority Data
Dec. 20, 2013  (GB) .................................. 1322692.3

(51) Int. Cl.
*C12N 15/10*  (2006.01)
*C40B 20/06*  (2006.01)
(Continued)

(52) U.S. Cl.
CPC .......... *C12N 15/1068* (2013.01); *C40B 20/06* (2013.01); *C40B 40/06* (2013.01); *C40B 50/10* (2013.01); *G01N 33/58* (2013.01); *C07H 21/02* (2013.01); *C07H 21/04* (2013.01); *C12Q 1/6874* (2013.01)

(58) Field of Classification Search
CPC .. C12N 15/1068; C12Q 1/6874; C40B 40/06; C40B 20/06; C07H 21/02; C07H 21/04; G01N 33/58
See application file for complete search history.

(56) References Cited

FOREIGN PATENT DOCUMENTS

WO    2003/076943 A1    9/2003
WO    2005/026387 A1    3/2005
(Continued)

OTHER PUBLICATIONS

International Application No. PCT/EP2014/077403, International Search Report and Written Opinion, dated Apr. 20, 2015.

*Primary Examiner* — Jeremy C Flinders
(74) *Attorney, Agent, or Firm* — Kilpatrick Townsend & Stockton LLP

(57) ABSTRACT

This invention relates to the synthesis of nucleic acid-encoded chemical libraries using common adaptor sequences. Nucleic acid strands coupled to chemical moieties may be contacted with identifier oligonucleotides comprising coding sequences encoding the chemical moieties and an adaptor oligonucleotides, such that the adaptor oligonucleotide hybridizes to both the nucleic acid strands and the identifier oligonucleotides to allow ligation of the identifier oligonucleotides to the nucleic acid strands. The adaptor oligonucleotide is then removed. Nucleic acid-encoded chemical libraries, and methods of producing or screening such libraries are provided.

27 Claims, 12 Drawing Sheets
Specification includes a Sequence Listing.

(51) Int. Cl.
*C40B 40/06* (2006.01)
*C40B 50/10* (2006.01)
*G01N 33/58* (2006.01)
*C12Q 1/6874* (2018.01)
*C07H 21/02* (2006.01)
*C07H 21/04* (2006.01)

(56) References Cited

FOREIGN PATENT DOCUMENTS

| WO | 2005/058479 A2 | 6/2005 |
|---|---|---|
| WO | 2007/062664 A2 | 6/2007 |
| WO | 2009/077173 A2 | 6/2009 |
| WO | 2010/094036 A1 | 8/2010 |
| WO | 2011/127933 A1 | 10/2011 |
| WO | 2013/036810 A1 | 3/2013 |

SEQUENCE LISTING

<160> NUMBER OF SEQ ID NOS: 15

<210> SEQ ID NO 1
<211> LENGTH: 25
<212> TYPE: DNA
<213> ORGANISM: Artificial sequence
<220> FEATURE:
<223> OTHER INFORMATION: Synthetic sequence: Chimeric adapter: DNA
      oligonucleotide with intermittent RNA nucleotides
<220> FEATURE:
<221> NAME/KEY: misc_feature
<222> LOCATION: (5)..(5)
<223> OTHER INFORMATION: RNA nucleotide
<220> FEATURE:
<221> NAME/KEY: misc_feature
<222> LOCATION: (11)..(11)
<223> OTHER INFORMATION: RNA nucleotide
<220> FEATURE:
<221> NAME/KEY: misc_feature

```
<222> LOCATION: (18)..(18)
<223> OTHER INFORMATION: RNA nucleotide

<400> SEQUENCE: 1
cgtcgatccg gcgccatggg actcg                                          25

<210> SEQ ID NO 2
<211> LENGTH: 25
<212> TYPE: DNA
<213> ORGANISM: Artificial sequence
<220> FEATURE:
<223> OTHER INFORMATION: Synthetic sequence: Chimeric adapter G1: DNA
      oligonucleotide with intermittent RNA nucleotides
<220> FEATURE:
<221> NAME/KEY: misc_feature
<222> LOCATION: (4)..(4)
<223> OTHER INFORMATION: RNA nucleotide
<220> FEATURE:
<221> NAME/KEY: misc_feature
<222> LOCATION: (11)..(11)
<223> OTHER INFORMATION: RNA nucleotide
<220> FEATURE:
<221> NAME/KEY: misc_feature
<222> LOCATION: (18)..(18)
<223> OTHER INFORMATION: RNA nucleotide

<400> SEQUENCE: 2
cgagtcccat ggcgccggat cgacg                                          25

<210> SEQ ID NO 3
<211> LENGTH: 20
<212> TYPE: DNA
<213> ORGANISM: Artificial sequence
<220> FEATURE:
<223> OTHER INFORMATION: Synthetic sequence: Chimeric adapter G2: DNA
      oligonucleotide with intermittent RNA nucleotides
<220> FEATURE:
<221> NAME/KEY: misc_feature
<222> LOCATION: (6)..(6)
<223> OTHER INFORMATION: RNA nucleotide
<220> FEATURE:
<221> NAME/KEY: misc_feature
<222> LOCATION: (13)..(13)
<223> OTHER INFORMATION: RNA nucleotide

<400> SEQUENCE: 3
gcctcgaggc gtgatcctac                                                20

<210> SEQ ID NO 4
<211> LENGTH: 21
<212> TYPE: DNA
<213> ORGANISM: Artificial sequence
<220> FEATURE:
<223> OTHER INFORMATION: Synthetic sequence: Chimeric test adapter: DNA
      oligonucleotide with intermittent RNA nucleotides
<220> FEATURE:
<221> NAME/KEY: misc_feature
<222> LOCATION: (4)..(7)
<223> OTHER INFORMATION: RNA nucleotides
<220> FEATURE:
<221> NAME/KEY: misc_feature
<222> LOCATION: (14)..(17)
<223> OTHER INFORMATION: RNA nucleotides

<400> SEQUENCE: 4
cgagtcccat ggcgcagctg c                                              21

<210> SEQ ID NO 5
<211> LENGTH: 80
<212> TYPE: DNA
<213> ORGANISM: Artificial sequence
```

```
<220> FEATURE:
<223> OTHER INFORMATION: Synthetic construct: Test ligation product
<220> FEATURE:
<221> NAME/KEY: misc_feature
<222> LOCATION: (22)..(29)
<223> OTHER INFORMATION: 6 variable nucleotides of code 1 of
      PCT/EP2014/077403
<220> FEATURE:
<221> NAME/KEY: misc_feature
<222> LOCATION: (51)..(56)
<223> OTHER INFORMATION: Abasic nucleotide backbone of PCT/EP2014/077403

<400> SEQUENCE: 5
cctgcatcga atggatccgt gnnnnnnnng cagctgcgcc atgggactcg nnnnnncagc    60
acacagaatt cagaagctcc                                                80

<210> SEQ ID NO 6
<211> LENGTH: 45
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (25)..(30)
<223> OTHER INFORMATION: 6 variable nucleotides of code 1 of
      PCT/EP2014/077403

<400> SEQUENCE: 6
ggagcttctg aattctgtgt gctgnnnnnn cgagtcccat ggcgc                    45

<210> SEQ ID NO 7
<211> LENGTH: 27
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (11)..(17)
<223> OTHER INFORMATION: 7 variable nucleotides of code 2 of
      PCT/EP2014/077403

<400> SEQUENCE: 7
cggatcgacg nnnnnnngcc tcgaggc                                        27

<210> SEQ ID NO 8
<211> LENGTH: 72
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (25)..(30)
<223> OTHER INFORMATION: 6 variable nucleotides of code 1 of
      PCT/EP2014/077403
<220> FEATURE:
<221> NAME/KEY: misc_feature
<222> LOCATION: (56)..(62)
<223> OTHER INFORMATION: 7 variable nucleotides of code 2 of
      PCT/EP2014/077403

<400> SEQUENCE: 8
ggagcttctg aattctgtgt gctgnnnnnn cgagtcccat ggcgccggat cgacgnnnnn    60
nngcctcgag gc                                                        72

<210> SEQ ID NO 9
<211> LENGTH: 31
```

```
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (16)..(21)
<223> OTHER INFORMATION: 6 complementary variable nucleotides of code 3
      of PCT/EP2014/077403

<400> SEQUENCE: 9
cgagtcccat ggcgcnnnnn ngtaggatca c                                   31

<210> SEQ ID NO 10
<211> LENGTH: 31
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (11)..(17)
<223> OTHER INFORMATION: Abasic nucleotide backbone of PCT/EP2014/077403

<400> SEQUENCE: 10
gcctcgaggc nnnnnnncgt cgatccggcg c                                   31

<210> SEQ ID NO 11
<211> LENGTH: 62
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (16)..(21)
<223> OTHER INFORMATION: 6 complementary variable nucleotides of code 3
      of PCT/EP2014/077403
<220> FEATURE:
<221> NAME/KEY: misc_feature
<222> LOCATION: (42)..(48)
<223> OTHER INFORMATION: Abasic nucleotide backbone of PCT/EP2014/077403

<400> SEQUENCE: 11
cgagtcccat ggcgcnnnnn ngtaggatca cgcctcgagg cnnnnnnncg tcgatccggc     60
gc                                                                   62

<210> SEQ ID NO 12
<211> LENGTH: 41
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (12)..(17)
<223> OTHER INFORMATION: Abasic nucleotide backbone of PCT/EP2014/077403

<400> SEQUENCE: 12
catgggactc gnnnnnncag cacacagaat tcagaagctc c                        41

<210> SEQ ID NO 13
<211> LENGTH: 72
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (11)..(17)
```

```
<223> OTHER INFORMATION: Abasic nucleotide backbone of PCT/EP2014/077403
<220> FEATURE:
<221> NAME/KEY: misc_feature
<222> LOCATION: (43)..(48)
<223> OTHER INFORMATION: Abasic nucleotide backbone of PCT/EP2014/077403

<400> SEQUENCE: 13
gcctcgaggc nnnnnnncgt cgatccggcg ccatgggact cgnnnnnnca gcacacagaa    60
ttcagaagct cc                                                         72

<210> SEQ ID NO 14
<211> LENGTH: 103
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (16)..(21)
<223> OTHER INFORMATION: 6 complementary variable nucleotides of code 3
      of PCT/EP2014/077403
<220> FEATURE:
<221> NAME/KEY: misc_feature
<222> LOCATION: (42)..(48)
<223> OTHER INFORMATION: Abasic nucleotide backbone of PCT/EP2014/077403
<220> FEATURE:
<221> NAME/KEY: misc_feature
<222> LOCATION: (74)..(79)
<223> OTHER INFORMATION: Abasic nucleotide backbone of PCT/EP2014/077403

<400> SEQUENCE: 14
cgagtcccat ggcgcnnnnn ngtaggatca cgcctcgagg cnnnnnnncg tcgatccggc    60
gccatgggac tcgnnnnnnc agcacacaga attcagaagc tcc                     103

<210> SEQ ID NO 15
<211> LENGTH: 103
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (25)..(30)
<223> OTHER INFORMATION: 6 variable nucleotides of code 1 of
      PCT/EP2014/077403
<220> FEATURE:
<221> NAME/KEY: misc_feature
<222> LOCATION: (56)..(62)
<223> OTHER INFORMATION: 7 variable nucleotides of code 2 of
      PCT/EP2014/077403
<220> FEATURE:
<221> NAME/KEY: misc_feature
<222> LOCATION: (83)..(88)
<223> OTHER INFORMATION: 6 variable nucleotides of code 3 of
      PCT/EP2014/077403

<400> SEQUENCE: 15
ggagcttctg aattctgtgt gctgnnnnnn cgagtcccat ggcgccggat cgacgnnnnn    60
nngcctcgag gcgtgatcct acnnnnnngc gccatgggac tcg                     103
```

PRODUCTION OF ENCODED CHEMICAL LIBRARIES

This application is the U.S. national stage of PCT/EP2014/077403, filed Dec. 11, 2014, which claims the benefit of priority to United Kingdom Application No. 1322692.3, filed Dec. 20, 2013, both of which are incorporated by reference herein in their entirety for all purposes.

This invention relates to encoded chemical libraries, particularly nucleic acid-encoded self-assembling chemical libraries.

Nucleic acid-encoded chemical libraries are collections of chemical moieties covalently linked to identifier oligonucleotides encoding the identity of the chemical moieties. The members of nucleic acid encoded chemical libraries display pharmacophores made up of one or more chemical moieties (also called "building blocks"). These chemical libraries can be used to identify pharmacophores which are candidate binding agents or have improved characteristics, for example improved binding.

Diverse populations of pharmacophores are produced by different combinations of chemical moieties. Each library member is tagged with a nucleic acid strand comprising nucleotide sequences that encode the chemical moieties that constitute the pharmacophore that is displayed by the member. This allows rapid identification of selected library members during screening.

DNA-encoded chemical library (DEL) technology allows the synthesis and screening of pharmacophores of unprecedented size and quality. DEL represents an advance in medicinal chemistry, which bridges the fields of combinatorial chemistry and molecular biology and promises to revolutionise the drug discovery field and to reshape the way pharmaceutically relevant compounds are traditionally discovered. Recent advances in ultrahigh-throughput nucleic acid sequencing (e.g. Illumina sequencing, SOLiD technology, etc.) indicate that it should be possible to sequence even billions of sequence tags per sequencing run. With suitable synthetic and encoding procedures, it should be possible to construct, perform selections, and decode nucleic acid-encoded libraries comprising multiple building blocks and containing millions of chemical compounds [1].

DNA encoded chemical libraries may display pharmacophores that are formed of chemically linked chemical moieties that are all attached to a single strand of nucleic acid ("single pharmacophore libraries") or pharmacophores that are formed of chemical moieties that are attached to two different strands of nucleic acid hybridised together, one or more chemical moieties being attached to each strand ("dual pharmacophore libraries").

DNA-encoded chemical libraries were proposed first by Sydney Brenner and Richard Lerner in 1992 ([2]; U.S. Pat. No. 5,573,905; WO93/20242). These authors postulated the alternating stepwise synthesis of a polymer (e.g. a peptide) and an oligonucleotide sequence (serving as a coding sequence) on a common linker (e.g. a bead) in split and pool cycles. After affinity capture on a target protein, the population of identifier oligonucleotides of the selected library members would be amplified by PCR and, in theory, utilised for enrichment of the bound molecules by serial hybridisation steps to a subset of the library. In principle, the affinity-capture procedure could be repeated, possibly resulting in a further enrichment of the active library members. Finally, the structures of the chemical entities would be decoded by cloning and sequencing the PCR products. It was postulated that encoding procedures could be implemented by a variety of methods, including chemical synthesis, DNA polymerization or ligation of DNA fragments [2].

The feasibility of the orthogonal, solid-phase synthesis of peptides and oligonucleotides was demonstrated by attaching a test peptide (the pentapeptide leucine enkephalin) and an encoding identifier oligonucleotide onto controlled-pore glass beads [3]. The peptide bound to a specific antibody and the corresponding DNA coding tag was amplified by PCR. The technology was used to construct a collection of $\sim 10^6$ heptapeptide sequences and their corresponding identifier oligonucleotide tags on beads. The library was incubated with a fluorescently labelled anti-peptide antibody, and binders were selected successfully by fluorescent-assisted cell sorting [4]. In their original paper, Brenner and Lerner suggested that the alternate synthesis of chemical compounds and oligonucleotides could also be implemented in the absence of beads. The use of enzyme catalysed ligation of coding DNA fragments is now established in the field (US 2006-0246450; WO 02/103008; WO2004/013070; WO2004/074429; WO2007/062664 and WO2005/058479).

Various methods of generating DNA-encoded chemical libraries have been described in the art (see for example [1, 2, 5-9]; WO2009/077173; WO2003/076943)

Standard strategies for encoding DNA-encoded chemical libraries based on two sets of building blocks involve the stepwise ligation of double-stranded DNA-fragments (containing a code for the unambiguous identification of each building block) after each addition of a chemical moiety in the library ([2], US 2006-0246450; WO 02/103008; WO2004/013070; WO2004/074429; WO2007/062664 and WO 2005/058479). In other words, the insertion of a chemical building block in a nascent chemical structure is associated with the ligation of a DNA-fragment that serves as code for that building block. The final code of the complete molecule is provided by the sum of the codes, corresponding to the individual building blocks.

However, in these standard strategies, each building block requires the synthesis and subsequent ligation of two complementary oligonucleotides. Thus, the synthesis of a library with n×m building blocks requires the synthesis of 2n+2m oligonucleotides.

A more economical method for the encoding of DNA-encoded chemical libraries consisting of two sets of n×m building blocks involves coupling the first n chemical moieties at the 5' end of n oligonucleotides [1]. In a split and pool synthetic strategy, the addition of m second building blocks to the nascent chemical structures was encoded by annealing the first n oligonucleotides with m partially complementary oligonucleotides that provided a code for the second reaction step. The structures were converted into double-stranded nucleic acid fragments by a Klenow-assisted polymerization step. Although this method is simple and efficient, it is not applicable for the synthesis of libraries with 3 or more sets of building blocks.

A general and economical method for the encoding of nucleic acid-encoded chemical libraries, based on any number of sets of building blocks would therefore be useful.

The present inventors have recognised that the annealing of oligonucleotides with common adaptor sequences allows the efficient and economical synthesis of nucleic acid-encoded chemical libraries. For example, a nucleic acid-encoded chemical library or a sub-library for use in generating a nucleic acid-encoded chemical library may be synthesised using fewer than two oligonucleotides for the addition and encoding of each building block.

A first aspect of the invention provides a method of producing a nucleic acid encoded chemical sub-library comprising;
 (i) providing a population of nucleic acid strands, each nucleic acid strand being coupled or couplable to one or more members of a diverse population of chemical moieties,
 (ii) contacting the nucleic acid strands coupled or couplable to the one or more chemical moieties with identifier oligonucleotides comprising coding sequences and one or more adaptor oligonucleotides, such that the adaptor oligonucleotides hybridize to both the nucleic acid strands and the identifier oligonucleotides to form partially double-stranded trimeric complexes,
 wherein each nucleic acid strand is contacted with an identifier oligonucleotide comprising a coding sequence that encodes a chemical moiety that is coupled or couplable to the nucleic acid strand, and;
 wherein each adaptor oligonucleotide forms multiple complexes with different nucleic acid strands and identifier oligonucleotides,
 (iii) ligating the nucleic acid strands to the identifier oligonucleotides in the partially double-stranded complexes, such that the identifier oligonucleotides are incorporated into the nucleic acid strands,
 thereby producing a sub-library of chemical moieties coupled to nucleic acid strands, wherein one or more chemical moieties are coupled to each nucleic acid strand and each nucleic acid strand comprises a coding sequence that encodes a chemical moiety coupled to the nucleic acid strand.

Preferably, all the nucleic acid strands in the population are contacted with the same adaptor oligonucleotide i.e. the same adaptor oligonucleotide hybridises to all of the nucleic acid strands in the population and all of the identifier oligonucleotides.

A nucleic acid-encoded self-assembling library or sub-library is a collection of library members or nascent library members, each of which displays a pharmacophore that is made up of one or more chemical moieties. The identity of the one or more chemical moieties that constitute the pharmacophore is encoded into each library member through a nucleic acid strand that incorporates a coding sequence. The members of the library display a diverse population of pharmacophores. This allows the screening of a large number of pharmacophores. For example, a nucleic acid-encoded self-assembling library may comprise $10^6$ or more different pharmacophores for screening.

Two or more nucleic acid encoded sub-libraries may be combined to generate a nucleic acid-encoded self-assembling library.

Nucleic acid-encoded libraries may be useful in the identification of pharmacophores which are candidates for binding to a target of interest, such as a protein, or which have improved characteristics compared to previously known pharmacophores, such as improved binding affinity to a target of interest. Suitable targets for nucleic acid-encoded libraries of pharmacophores are well known in the art.

Following screening, the identity of the pharmacophore that is displayed by a selected library member may be determined by decoding the coding sequences that are incorporated into the nucleic acid strand of the selected library member.

A member of a nucleic acid-encoded chemical library ('library member') may be formed from two nucleic acid strands (a first and a second strand) and one or more chemical moieties.

A nucleic acid strand may be DNA, RNA or chimeric RNA/DNA. Preferably, the nucleic acid strand(s) in the chemical libraries described herein are DNA.

The first nucleic acid strand of the library member may be coupled to one, two, three, or more than three chemical moieties and the second nucleic acid strand of the member may be coupled to zero, one, two, three, or more than three chemical moieties. The chemical moieties may be coupled to one of the 5' and 3' ends of the first nucleic acid strand and the other of the 5' and 3' ends of the second nucleic acid strand. The chemical moieties in each member form the pharmacophore that is displayed by the member. A chemical library contains library members that together display a diverse population of pharmacophores. The nucleic acid strands hybridize to form a duplex nucleic acid molecule which is coupled to the pharmacophore that is displayed by the library member. The nucleic acid strands may self-assemble through the hybridization of complementary regions in each strand to form a double-stranded or partially double stranded nucleic acid molecule.

In some embodiments, a chemical library member may be formed from a first nucleic acid strand coupled to one or more chemical moieties that form a pharmacophore, and a second nucleic acid strand that is hybridised to the nucleic acid strand that is not coupled to a chemical moiety (i.e. only the first nucleic acid strand contributes to the pharmacophore). For example, the first nucleic acid strand may be coupled to three chemical moieties and the second strand may not be coupled to any chemical moieties.

In other embodiments, a chemical library member may be formed from a first nucleic acid strand and a second nucleic acid strand, each of which is coupled to one or more chemical moieties, such that the chemical moieties coupled to the strands together form a pharmacophore (i.e. both the nucleic acid strands contribute to the pharmacophore). For example, the first nucleic acid strand may be coupled to one chemical moiety and the second nucleic acid strand may be coupled to one chemical moiety or the first nucleic acid strand may be coupled to two chemical moieties and the second nucleic acid strand may be coupled to one chemical moiety.

The nucleic acid strands that form the library members may themselves be members of a sub-library, each nucleic acid strand in the sub-library being coupled to a different chemical moiety or combination of chemical moieties.

The self-assembled library may be formed from the hybridisation of a sub-library of first nucleic acid strands, each first nucleic acid strand being coupled to one or more members of a first diverse population of chemical moieties, with a sub-library of second nucleic acid strands, each second nucleic acid strand being coupled to one or more members of a second diverse population of chemical moieties. The first and second diverse populations may be the same or different. When the sub-libraries of nucleic acid strands hybridise together to form double-stranded library members, pharmacophores are generated from the different combinations of the chemical moieties coupled to the nucleic acid strands. This increases the number of different pharmacophores in the library.

A sub-library may comprise different chemical moieties coupled to nucleic acid strands. The nucleic acid strands in a sub-library may assemble through hybridisation with nucleic acid strands from the same sub-library or a different sub-library, for example a sub-library of nucleic acid strands conjugated to a different number of chemical moieties, to produce a double-stranded library. For example, in the simplest scenario, a sub-library comprising nucleic acid strands coupled to one chemical moiety may assemble with a partner nucleic acid strand which is not coupled to a chemical moiety. The pharmacophore would then consist of one chemical moiety. In a further example, nucleic acid strands coupled to single chemical moieties may assemble with nucleic acid strands coupled to two chemical moieties, thereby presenting a pharmacophore consisting of three chemical moieties. These examples are for illustration only and any number of combinations can be envisaged. For some purposes, a pharmacophore formed by chemical moieties coupled to one nucleic acid strand may be preferred as the moieties are bound together and therefore represent a lead-like compound. For other purposes, a pharmacophore formed by chemical moieties coupled to different nucleic acid strands may be preferred.

A nucleic acid strand is a polynucleotide chain (e.g. a DNA, RNA or RNA/DNA chain) which may be coupled to one or more chemical moieties. A nucleic acid strand may hybridize to a second nucleic acid strand through complementary regions in the two strands. A nucleic acid strand may be coupled to 0, 1, 2, 3, 4, 5 or more chemical moieties which may form all or part of the pharmacophore.

When a nucleic acid strand hybridizes to one or more partner nucleic acid strands to form a library member, the chemical moieties that are coupled to the strands form the pharmacophore that is displayed by the library member. In some embodiments, only one of the strands is coupled to chemical moieties in the pharmacophore (often termed a "single-pharmacophore" library). In other embodiments, both of the strands may be coupled to chemical moieties in the pharmacophore (often termed a "dual-pharmacophore" library).

During the production of a library member as described herein, a nucleic acid strand may act as a scaffold into which one or more coding sequences are incorporated, for example by the ligation of identifier oligonucleotides comprising coding sequences onto the nucleic acid strand or the polymerase mediated extension of the nucleic acid strand along a template that comprises the complement of a coding sequence.

In some embodiments, a nucleic acid strand for use in the methods described herein may initially contain coding sequences encoding one or more chemical moieties. For example, the nucleic acid strand may initially contain a coding sequence that encodes the chemical moiety that is coupled or couplable to the nucleic acid strand. One or more further identifier oligonucleotides comprising coding sequences encoding further chemical moieties coupled or couplable (i.e. capable of being coupled) to the nucleic acid strand may be added during the production of the library member as described herein.

A nucleic acid strand may initially be coupled to one or more chemical moieties and further chemical moieties may be subsequently coupled to the nucleic acid strand.

The nucleic acid strand may be coupled to the chemical moiety at any step of the methods disclosed herein. For example, the nucleic acid strand may be coupled to the chemical moiety before, or after the step of ligating the nucleic acid strand to the identifier oligonucleotide. For example coupling may be performed before step (i), before step (ii) or after step (iii). Suitable methods for coupling chemical moieties to nucleic acid strands are well-known in the art.

The nucleic acid strand may comprise a proximal end that is coupled to the chemical moiety, for example the 5' end, and a distal end to which the coding sequence is added, for example the 3' end. An annealing region which hybridises with the adaptor oligonucleotide may be located adjacent the distal end of the nucleic acid strand to facilitate ligation of an identifier oligonucleotide.

The nucleic acid strand may comprise first and second hybridisation regions to anneal primers for the amplification of the strand, for example after screening. Amplification products produced by amplification of the nucleic acid strand may comprise the coding sequences encoding the chemical moieties that form the pharmacophore displayed by the library member. The typical length of regions for primer annealing is between 10 and 28 nucleotides (in single stranded format), or base pairs (in double stranded format). In double stranded format, one of the two nucleic acid strands of the region may form a sequence specific dimer with a PCR primer at an appropriate hybridisation temperature. A typical hybridisation temperature for the sequence specific hybridisation of PCR primers to PCR primer regions is between 40 and 70° C. PCR primers can be longer than the hybridisation region of the nucleic acid strand or contain additional sequences (e.g., at their respective 5' ends). This may be useful for later steps of the decoding process.

The one or more chemical moieties coupled to the nucleic acid strand or strands of a library member form a pharmacophore. A pharmacophore is a collection of molecular features or elements which is capable of specifically interacting with a target. Different combinations of chemical moieties produce different pharmacophores which are displayed by different members of the library.

The pharmacophore may be formed from chemical moieties which are covalently bound together; chemical moieties which are not covalently bound together; or combinations of both. Typically, chemical moieties on the same nucleic acid strand will be covalently bonded together and chemical moieties on different nucleic acid strands will be brought together by the assembly of the nucleic acid strands. For example, one or more chemical moieties coupled to a nucleic acid strand may associate with one or more moieties attached to a partner nucleic acid strand to form a pharmacophore.

Suitable targets for binding to pharmacophores include biological targets, for example biological macromolecules, such as proteins. The target may be a receptor, enzyme, antigen or oligosaccharide. The target may be a compound, for example a synthetic compound. The interaction with the target is generally through specific binding of all or part of the pharmacophore with the target. In other words, some or all or the chemical moieties, or parts of the chemical moieties which form the pharmacophore may specifically bind to the target.

The binding between the pharmacophore and target may occur through intermolecular forces such as ionic bonds, hydrogen bonds and van der Waals forces, which are generally reversible. The binding may occur through covalent bonding, which is generally irreversible, although this is generally rare in biological systems.

The pharmacophore formed by the chemical moieties may, for example, be a ligand, substrate, inhibitor or activator or may be useful in the development thereof. The pharmacophore may be an agonist or antagonist or a candidate agonist or antagonist or may be used as a model or lead in the development of such an agonist or antagonist.

A chemical moiety may form all or part of a pharmacophore. A single chemical moiety may be the pharmacophore or preferably may associate with other chemical moieties coupled to the library member to form a pharmacophore comprising multiple chemical moieties. The pharmacophore and/or chemical moieties are used in screening.

A chemical library member may display a pharmacophore which comprises or consists of any of 1, 2, 3, 4, 5 or more chemical moieties. The chemical moieties may be attached to one or both nucleic acid strands. For example, a first strand may be coupled to 1, 2, 3, 4, 5 or more chemical moieties and a second strand may be coupled to 0, 1, 2, 3, 4, 5 or more chemical moieties In some preferred embodiments, the total molecular weight of the chemical moieties in the pharmacophore may be less than 1 kD, preferably less than 500 D.

Suitable chemical moieties include small organic molecules, amino acid residues or other amino-containing moieties (optionally with appropriate amino protection); and peptides or globular proteins (including antibody domains). In some embodiments, a chemical moiety may have a molecular weight of 300 Da or less, for example about 100 to 300 Da. Populations of chemical moieties for use in the generation of libraries are well known in the art (see [1] to [9]).

A chemical moiety may be covalently coupled to the nucleic acid strand directly or indirectly, for example via a linker. Suitable linkers, such as alkyl chains, are well known in the art. The chemical moiety may be coupled directly using conventional synthetic chemistries, for example amide or other conventional linkages.

Chemical moieties may be coupled to a nucleic acid strand via other chemical moieties. For example, each of the chemical moieties coupled to a nucleic acid strand may be covalently bonded to other chemical moieties and one of the chemical moieties may be coupled to the nucleic acid strand. Suitable methods for covalently bonding chemical moieties are well known in the art. In some embodiments, a pharmacophore may be formed from a single compound comprising the covalently-bound chemical moieties coupled to a nucleic acid strand.

In other embodiments, the pharmacophore displayed by a library member may be formed from two or more chemical moieties which are covalently bonded to each other, and a further one or more chemical moieties which are not covalently bonded to the covalently bonded moieties.

For example, two or more covalently bonded chemical moieties may be coupled to one of a nucleic acid strand or a partner nucleic acid strand and form a pharmacophore with a further one or more chemical moieties coupled to the other of a nucleic acid strand or a partner nucleic acid strand, when the strands assemble to form a double-stranded library member.

An example of this structure is shown in FIGS. 2A, 2B and 2C, where the pharmacophore is formed from bbA, bbB and bbC. bbB and bbA are covalently bonded to each other and are also coupled to a nucleic acid strand while bbC is coupled to a partner nucleic acid strand but is not covalently bonded to bbA or bbB.

A chemical moiety may be coupled to the 5' or 3' terminal of a nucleic acid strand.

If there are two or more chemical moieties coupled to a nucleic acid strand, these may be joined to one another by one or more chemical reactions and their residues will be linked by one or more chemical bonds.

The chemical moieties may be joined to one another by covalent bonds or by non-covalent interactions.

Library members as described herein comprise a double-stranded nucleic acid molecule. Preferably, one of the nucleic acid strands comprises coding sequences that encode all of the chemical moieties that constitute the pharmacophore displayed by the library member.

The adaptor oligonucleotide serves as a template to facilitate the ligation of the nucleic acid strand and the identifier oligonucleotide containing the coding sequence. A single adaptor oligonucleotide may facilitate the ligation of multiple nucleic acid strands and identifier oligonucleotides. For example, a set consisting of 1, 2, 3, 4, 5 or more adaptor oligonucleotides may be used to facilitate ligation of all of the nucleic acid strands in the population to the identifier oligonucleotide containing the corresponding coding sequence. Preferably, the sequence of the adaptor oligonucleotide is the same regardless of the chemical moiety(s) coupled to the nucleic acid strand i.e. only 1 adaptor oligonucleotide is used. This reduces the total number of oligonucleotides required to generate the nucleic acid encoded chemical library.

The adaptor oligonucleotide hybridises with the nucleic acid strand and identifier oligonucleotide and brings the ends of the nucleic acid strand and identifier oligonucleotide into association within a double-stranded trimeric complex, such that they can be ligated together by a ligase. The adaptor may bring into association the 3' end of the nucleic acid strand to the 5' end of the identifier oligonucleotide or the 5' end of the nucleic acid strand to the 3' end of the identifier oligonucleotide.

The association is maintained by hybridization of a first annealing region of the adaptor to a complementary annealing region of the nucleic acid strand and a second annealing region of the adaptor to a complementary annealing region of the identifier oligonucleotide. The complementary annealing regions contain a nucleotide sequence that is complementary to the annealing region. The sequences of the complementary annealing region of the nucleic acid strand and the identifier oligonucleotide are the same, regardless of the chemical moiety(s) coupled to the nucleic acid strand, to allow the same adaptor oligonucleotide sequence to be used to encode all the chemical moieties in the library.

The first annealing region of the adaptor may be proximal to the chemical moiety and may hybridise with a complementary annealing region at the distal end of the nucleic acid strand. The second annealing region of the adaptor may be distal to the chemical moiety and may hybridise with the proximal complementary annealing region of the identifier oligonucleotide.

The proximal and distal annealing regions of the adaptor may comprise or consist of nucleic acid or RNA bases or both. The proximal and distal annealing regions contain sufficient numbers of bases so that they can hybridise to complementary regions on the nucleic acid strand and identifier oligonucleotide respectively. Typically, an annealing region will contain at least 6 nucleotides, and more preferably at least 9 nucleotides. Normally, the annealing region will contain no more than 20 nucleotides, preferably not more than 15 nucleotides. For example, the first and second annealing regions of the adaptor may be 9 to 15 bases in length. A suitable adaptor oligonucleotide may, for example be 15 to 35 bases, preferably 18 to 30 bases in length.

The adaptor oligonucleotide hybridises to the nucleic acid strand and the identifier oligonucleotide such that a complex that comprises a double-stranded region is formed in the vicinity of the ends of the nucleic acid strand and the identifier oligonucleotide that are to be ligated.

In some embodiments, the adaptor may remain hybridised to the first nucleic acid strand, for example within a nucleic acid spacer strand, and may form part of the library member that is produced.

In other embodiments, the adaptor may be removable or removed by purification following the ligation step. For example, adaptor may be separated under denaturing conditions on the basis of their small size relative to the nucleic acid strand incorporating the identifier oligonucleotide.

More preferably, the adaptor oligonucleotide may be cleavable. Cleavage of the adaptor oligonucleotide produces fragments which are too short to remain hybridised to the nucleic acid strand and the identifier oligonucleotide. The adaptor oligonucleotide is thus removed from the nucleic acid strand and the identifier oligonucleotide by cleavage after ligation has occurred.

Cleavage or degradation of the adaptor results in separation of the adaptor oligonucleotide from the nucleic acid strand. In some embodiments, the nucleic acid strand may be purified following removal of the adaptor for example to remove fragments of a cleaved or degraded adaptor. Suitable purification methods are well known in the art.

The adaptor oligonucleotide may be cleaved enzymatically, for example using RNAase, or chemically, for example by base hydrolysis (typically, exposure to pH>12 at room temperature or greater).

The adaptor oligonucleotide may be DNA, RNA or chimeric (i.e. containing both deoxyribonucleotides and ribonucleotides).

In some preferred embodiments, the adaptor oligonucleotide is chimeric. In addition to deoxyribonucleotides, a suitable chimeric adaptor oligonucleotide may comprise one or more ribonucleotides, for example two or more, three or more, four or more or five or more ribonucleotides. The ribonucleotide bases in the adaptor may be consecutive or non-consecutive. The ribonucleotide sequence may be located within the adaptor such that cleavage of the RNA, e.g. via hydrolysis produces fragments which are too short to hybridise to the nucleic acid strand and the identifier oligonucleotide. For example, the adaptor may comprise one or more contiguous sequences of 2, 3, 4, 5, 6, 7, 8, or more deoxyribonucleotide bases that are separated by 1, 2, 3, 4 or more ribonucleotide bases. Examples of suitable chimeric adaptor oligonucleotides for use as described herein are shown in Tables 1 and 2.

RNA adaptors or chimeric adaptor oligonucleotides may be conveniently cleaved by treatment with RNAase. RNAse is a nuclease which catalyses the degradation of RNA into smaller components. RNAse is readily available from commercial suppliers.

Suitable adaptor oligonucleotides may be synthesised using appropriate techniques.

Hybridization of the adaptor oligonucleotide to the nucleic acid strand and the identifier oligonucleotide brings an end of the nucleic acid strand into proximity to an end of the identifier oligonucleotide so that a ligase enzyme may act to join the identifier oligonucleotide to the nucleic acid strand. Suitable hybridisation conditions for the hybridisation of polynucleotides are well-known in the art and include for example a temperature of between 0° C. and 70° C.

Identifier oligonucleotides suitable for use as described herein comprise a coding sequence that encodes a chemical moiety.

The coding sequence (or coding region) can be any sequence of nucleic acid bases that is uniquely associated with a particular chemical moiety. This allows the identity of the chemical moiety to be determined by sequencing or otherwise 'reading' the coding sequence.

A coding sequence contains sufficient nucleotides to uniquely identify the chemical moiety for which it is coding. For example, if the chemical moiety has 20 variants, the coding sequence needs to contain at least 3 nucleotides ($4^2=16$, $4^3=64$). The coding sequence may be longer than necessary. The benefit of employing coding sequences that are longer than necessary is that they provide the opportunity to differentiate codes by more than just a single nucleotide difference, which gives more confidence in the decoding process. For example, a first chemical moiety from a population of 20 different moieties (20 compounds) may be encoded by 6 nucleotides, and a second chemical moiety from a population of 200 different moieties may be encoded by 8 nucleotides. The size of the coding sequence therefore depends on the number of chemical moieties to be encoded (i.e. the number of different chemical moieties in the library). A sequence of nucleotides and/or its complement may be used as a coding sequence to encode a chemical moiety. Suitable sequences for encoding chemical moieties in a library are well-known in the art.

Preferably, the coding sequences of the identifier oligonucleotides are flanked by constant regions. The constant regions are of sufficient length to allow an efficient hybridization and ligation, for example 3-20 bases, preferably 9-15 bases. Examples of suitable sequences are shown in Tables 5-7.

The constant regions of the identifier oligonucleotide may comprise one or more complementary annealing regions that hybridize to annealing regions of the adaptor. Preferably, the sequence of the complementary annealing region is the same in all the identifier oligonucleotides regardless of the coding sequence i.e. identifier oligonucleotides encode the different chemical moieties (and therefore having different coding sequences) comprise the same complementary annealing region. This allows a single adaptor to be used for the ligation of different identifier oligonucleotides to nucleic acid strands.

The complementary annealing regions of the identifier oligonucleotide are of sufficient length to allow for specific hybridisation between the complementary annealing region and the annealing region of the adaptor. Typically, a complementary annealing region will contain at least 6 nucleotides, more preferably at least 9 nucleotides and no more than 15 nucleotides. Suitable conditions for the sequence specific hybridisation of two polynucleotides are well known in the art.

Complementary annealing regions may be located either side of the coding sequence in the identifier oligonucleotide. For example, a first complementary annealing region may be on the proximal side of the coding sequence (i.e. nearest the end that is ligated to the nucleic acid strand) and a second complementary annealing region may be on the distal side of the coding sequence (i.e. furthest the end that is ligated to the nucleic acid strand). The first and second complementary annealing regions may have the same sequence or more preferably different sequences to each other.

The complementary annealing region may be capable of hybridizing to a complementary region in a second nucleic acid strand to facilitate the assembly of double-stranded library members.

Identifier oligonucleotides and chemical moieties may be added to the library member in alternate cycles, at least partly because of different reaction conditions being required for the two steps. In some embodiments, the chemical moiety can be added first and then its identifier oligonucleotide incorporated into the nucleic acid strand, or the identifier oligonucleotide can be incorporate into the nucleic acid strand and then the chemical moiety encoded by the incorporated identifier oligonucleotide may be added to the nascent library member. In methods of the invention, coupling may occur before step i) before step ii) or after step iii). In some cases, the identifier oligonucleotide may be used to direct synthesis or addition of the encoded chemical moiety, in which case the identifier oligonucleotide may be added before the chemical moiety.

The adaptor may be hybridized to the nucleic acid strand and identifier oligonucleotide through the annealing of annealing regions in the adaptor to complementary annealing regions in the nucleic acid strand and the identifier oligonucleotide.

Hybridization establishes a non-covalent sequence-specific base-pairing between one or more complementary strands of nucleic acids. Under suitable reaction conditions the complementary strands will anneal and form a double stranded complex. Suitable hybridisation conditions are well-known in the art. Typical hybridisation temperatures for the sequence specific annealing of two polynucleotide strands may be between 0° C. and 70° C.

The nucleic acid strand may be ligated to the identifier oligonucleotide by any suitable technique known in the art.

Preferably, the nucleic acid strand and identifier oligonucleotide may be enzymatically ligated, e.g. using DNA or RNA ligase. DNA and RNA ligases catalyze the formation of a phosphodiester bond between the 3' hydroxyl and 5' phosphate of adjacent DNA or RNA residues, respectively. The ligation step joins an end of the nucleic acid strand to an end of the identifier oligonucleotide such that the identifier oligonucleotide is incorporated into the nucleic acid strand. Suitable ligation conditions are well-known in the art.

In some embodiments, following ligation, the adaptor may be separated or removed from the nucleic acid strand comprising the ligated identifier oligonucleotide, for example by cleavage or degradation, as described above. In other embodiments, the adaptor may remain hybridised as part of the double stranded nucleic acid molecule within library members.

The nucleic acid strand may be hybridised to a second nucleic acid strand in order to assemble a library member comprising a double-stranded nucleic acid molecule.

The second nucleic acid strand is capable of hybridizing to the nucleic acid strand, as described above. The second nucleic acid strand may comprise one or more hybridization regions which hybridize to complementary regions in the first nucleic acid strand thereby allowing the first and second nucleic acid strands to assemble or dimerise as a double-stranded or partially double stranded complex. Suitable hybridization regions may comprise between 18 and 24 bases, in order for the nucleic acid strands to self-assemble into a library member.

One or both of the nucleic acid strands may comprise first and second primer regions as described above.

As described above, the second nucleic acid strand may be coupled to one or more chemical moieties. For example, the partner nucleic acid strand may be coupled to 1, 2, 3, 4, 5 or more chemical moieties. The coupling may be covalent and may be direct or via a linker as described herein. In some embodiments, the second nucleic acid strand may be coupled or couplable to a second chemical moiety. The second nucleic acid strand may comprise a second coding sequence that encodes the second chemical moiety. In other embodiments, the second nucleic acid strand may not be coupled to a chemical moiety.

As described above, the chemical moieties that are coupled to the first nucleic acid strand or the first and second nucleic acid strands form a pharmacophore, when the strands self-assemble through hybridisation to form the library member.

The nucleic acid strand or the second nucleic acid strand may comprise a spacer region. The spacer region is non-hybridizable and may be called a non-hybridizable spacer.

The spacer region is an abasic region that does not hybridise to nucleotide sequences and is not a template for a nucleic acid polymerase. Suitable spacer regions may comprise an abasic phosphodiester backbone or a linker, such as an alkyl chain, polyethylene glycol or other oligomer that spans the spacer region.

Suitable spacer regions may be obtained from commercial suppliers. The spacer region may be located in a first nucleic acid strand at a position that would otherwise hybridise with a coding sequence located in the second nucleic acid strand in the double stranded nucleic acid molecule or may be located in the second nucleic acid strand at the region that would otherwise hybridise with a coding sequence in the first nucleic acid strand. In some embodiments, regions complementary to the first coding sequence; the first and second coding sequences; or the first, second and third coding sequences may be replaced by spacer regions.

A nucleic acid strand containing one or more spacer regions at positions corresponding to coding sequences may hybridise to nucleic acid strands containing different coding sequences. This may be useful in the production of diversity in self-assembling libraries.

In some embodiments, the hybridisation of a first and a second nucleic acid strand may leave a single stranded overhanging region in the first nucleic acid strand. The single-stranded region of the first nucleic acid strand may comprise a first coding sequence. The first nucleic acid strand may further comprise a spacer region that corresponds in the double stranded nucleic acid molecule to a second coding region in the second nucleic acid strand, such that the first nucleic acid strand does not hybridize to the second coding region of the second nucleic acid strand. A method may comprise;

extending the second nucleic acid strand along the first nucleic acid strand, such that the second nucleic acid strand incorporates the complement of the first coding sequence.

The second nucleic acid strand of the library member may thereby comprise a first coding sequence encoding a first chemical moiety and a second coding sequence encoding a second chemical moiety.

Suitable techniques for extending a nucleic acid strand along a template nucleic acid strand are well known in the art. For example, the second nucleic acid strand may be extended by addition of nucleotides for polymerisation (normally in excess), preferably deoxynucleotides (dNTPs), and a polymerase (e.g. Taq or Klenow polymerase) in a suitable buffer, incubated at a suitable temperature (e.g. 37° C. for Klenow polymerase or 65° C. or 72° C. for Taq). In some embodiments, the nucleic acid strands of a nucleic acid encoded chemical sub-library may be coupled to a single chemical moiety.

A method of producing a nucleic acid encoded chemical sub-library may comprise, (i) providing a first diverse population of chemical moieties, (ii) coupling a nucleic acid strand to the diverse population of chemical moieties, (iii) contacting the nucleic acid strands coupled to the chemical moieties in the population with identifier oligonucleotides comprising coding sequences and one or more adaptor oligonucleotides, such that the adaptor oligonucleotides hybridize to the nucleic acid strands and the identifier oligonucleotides to form partially double-stranded complexes, wherein each nucleic acid strand is contacted with an identifier oligonucleotide that comprises a coding sequence that encodes the chemical moiety coupled to the nucleic acid strand, and;

each adaptor oligonucleotide hybridizes to more than one nucleic acid strand and more than one identifier oligonucleotide, and (iv) ligating the nucleic acid strands to the identifier oligonucleotides in the partially double-stranded complexes, such that the identifier oligonucleotides are incorporated into the nucleic acid strands, thereby producing a sub-library of different chemical moieties, each chemical moiety being coupled to a nucleic acid strand comprising a coding sequence that encodes the chemical moiety In some preferred embodiments, all the nucleic acid strands are contacted with the same adaptor oligonucleotide.

Following ligation, the adaptor may be removed, as described above. In some preferred embodiments, the adaptor may be cleaved, for example by base hydrolysis or enzymatic treatment.

The nucleic acid strand may comprise a spacer at a position that corresponds to a second coding sequence in a second nucleic acid strand. A method may further comprise;

(v) hybridizing the nucleic acid strands to second nucleic acid strands to form a double-stranded complex, wherein the second nucleic acid strands are coupled to a second diverse population of chemical moieties, each second nucleic acid strand comprising a second coding sequence that encodes the chemical moiety that is coupled to it, the position of the second coding sequence in the second nucleic acid strands corresponding in the double-stranded complex to the position of the spacer in the first nucleic acid strand in the double-stranded complex, such that the second coding sequence does not hybridise to the first nucleic acid strand, (vi) extending the second nucleic acid strand along the nucleic acid strand to produce a library comprising members having;

the first nucleic acid strand and the second nucleic acid strand annealed together;

a chemical moiety from the first diverse population being coupled to the first nucleic acid strand and a chemical moiety from the second diverse population being coupled to the second nucleic acid strand, said chemical moieties forming a pharmacophore for screening, wherein the second nucleic acid strand comprises a first coding sequence that encodes the chemical moiety from the first diverse population and a second coding sequence that encodes the chemical moiety from the second diverse population.

Methods of the invention may be useful in the generation of nucleic acid encoded chemical libraries. Examples of suitable methods are shown in FIGS. 1A and 1B.

For example, a method of producing a nucleic acid encoded chemical library may comprise, (i) providing a first nucleic acid strand comprising a non-hybridisable spacer and having a first chemical moiety conjugated thereto, (ii) contacting the first nucleic acid strand with an adaptor and an identifier oligonucleotide comprising a coding sequence encoding the first chemical moiety, wherein the adaptor comprises a first annealing region portion which hybridizes to the first nucleic acid strand, and a second annealing region which hybridizes to the identifier oligonucleotide to form a double-stranded complex comprising the first nucleic acid strand, cleavable adaptor and identifier oligonucleotide, (iii) ligating the first nucleic acid strand to the identifier oligonucleotide in the double-stranded complex, such that the identifier oligonucleotide is incorporated into the first nucleic acid strand; and (iv) removing the adaptor to produce a first nucleic acid strand linked to the chemical moiety and comprising a coding sequence encoding the chemical moiety, (v) repeating steps (i) to (iv) in series or in parallel using different first chemical moieties and coding sequences and the same adaptor to produce a diverse population of first chemical moieties, each chemical moiety being coupled to a first nucleic acid strand which comprises a first coding sequence encoding the first chemical moiety, (vi) contacting the diverse population of first chemical moieties with a diverse population of second chemical moieties, each second chemical moiety being coupled to a second nucleic acid strand which comprises a second coding sequence encoding the second chemical moiety coupled thereto, such that the first and second nucleic acid strands hybridise to form a double-stranded nucleic acid molecule, wherein the position of the second coding sequence in the second nucleic acid strands corresponds to the position of the non-hybridisable spacer in the first nucleic acid strands, such that the second coding sequence does not hybridise to the first nucleic acid strands in the in the double-stranded nucleic acid molecules, and (vii) extending the second nucleic acid strands along the first nucleic acid strands to produce a nucleic acid encoded chemical library each member of the library comprising;

a pharmacophore comprising a member of the diverse population of first chemical moieties and a member of a diverse population of second chemical moieties and;

a nucleic acid strand comprising a first coding sequence that encodes the first chemical moiety of the pharmacophore and a second coding sequence that encodes the second chemical moiety of the pharmacophore.

In some embodiments, further chemical moieties may be coupled to one or both of the nucleic acid strands, for example using a so-called "split and pool" method. Examples of suitable methods are shown in FIGS. 2 and 3. For example, steps (i) to (iv) may be repeated to couple a second chemical moiety to the first nucleic acid strand and incorporate a second coding sequence encoding the second chemical moiety into the first nucleic acid strand. For example, a method may further comprise;

(v) coupling a diverse population of second chemical moieties to the first nucleic acid strands, (vi) contacting the first nucleic acid strands coupled to the second chemical moieties with a second adaptor and a second identifier oligonucleotide comprising a coding sequence, such that the second adaptor hybridizes to the first nucleic acid strands and the identifier oligonucleotides to form partially double-stranded complexes, wherein each first nucleic acid strand is contacted with a second identifier oligonucleotide that comprises a second coding sequence that encodes the second chemical moiety that is coupled to the first nucleic acid strand, and;

each second adaptor oligonucleotide hybridizes to more than one first nucleic acid strand and more than one second identifier oligonucleotide, and (vii) ligating the first nucleic acid strands to the second identifier oligonucleotides in the double-stranded complexes, such that the second coding sequence identifier oligonucleotides are incorporated into the nucleic acid strands.

The adaptor may then be removed, for example by cleavage and/or purification, to produce a sub-library; each member of the sub-library comprising a first and a second chemical moiety coupled to a first nucleic acid comprising coding sequences encoding the first and second chemical moieties.

Step v) may be performed before step vi) or after step vii).

The second chemical moieties are coupled to the same ends of the nucleic acid strands as the first chemical moieties, so that the second chemical moieties and first chemical moieties form a pharmacophore on the same strand for screening.

The second chemical moiety may be coupled to the first chemical moiety or to the first nucleic acid strand, either directly or through a linker.

Preferably, all the nucleic acid strands are contacted with a second adaptor oligonucleotide having the same nucleotide sequence i.e. the same second adaptor oligonucleotide sequence hybridises to all of the nucleic acid strands and second identifier oligonucleotides.

The second adaptor oligonucleotide may be the same as the first adaptor oligonucleotide or more preferably different.

The second adaptor hybridizes to the distal end of the nucleic acid strand i.e. the end that is not linked to the chemical moiety. In some embodiments, the second adaptor may hybridise to a complementary annealing sequence of the first identifier oligonucleotide which is incorporated into the nucleic acid strand. Steps (v) to (vii) may be repeated one or more times to couple further chemical moieties to the first nucleic acid strand and incorporate coding sequences encoding the further chemical moieties into the first nucleic acid strand, for example as shown in FIGS. 3A and 3B. For example, a method may further comprise;

(viii) coupling a diverse population of further chemical moieties to the first nucleic acid strands, (ix) contacting the first nucleic acid strands coupled to the further chemical moieties with a further adaptor oligonucleotide and a further identifier oligonucleotide comprising a coding sequence, such that the further adaptor oligonucleotide hybridizes to the nucleic acid strands and the identifier oligonucleotides to form partially double-stranded complexes, wherein each nucleic acid strand is contacted with a further identifier oligonucleotide that comprises a further coding sequence that encodes the further chemical moiety that is coupled to the nucleic acid strand, and;

each further adaptor oligonucleotide hybridizes to more than one nucleic acid strand and more than one further identifier oligonucleotide, and (x) ligating the nucleic acid strands to the further identifier oligonucleotides in the double-stranded complexes, such that the further coding sequence identifier oligonucleotides are incorporated into the nucleic acid strands.

The adaptor may then be removed, for example by cleavage and purification to produce a sub-library; each member of the sub-library comprising first, second and further chemical moieties coupled to a nucleic acid strand comprising coding sequences encoding the first, second and further chemical moieties.

Step viii) may be performed before step ix) or after step x).

The further chemical moiety may be coupled to the same end of the nucleic acid strand as the first and second chemical moieties, so that the chemical moieties form a pharmacophore for screening. The further chemical moiety may be coupled to the first chemical moiety, the second chemical moiety or the nucleic acid strand, either directly or through a linker.

Preferably, all the nucleic acid strands are contacted with a further adaptor oligonucleotide having the same nucleotide sequence i.e. the same further adaptor oligonucleotide sequence hybridises to all of the nucleic acid strands and further identifier oligonucleotides.

The further adaptor may have the same sequence as the first and second adaptors or more preferably, a different sequence.

The further adaptor hybridizes to the distal end of the nucleic acid strand i.e. the end that is not linked to the chemical moiety. In some embodiments, the further adaptor may hybridise to a complementary annealing sequence of the second identifier oligonucleotide which is incorporated into the nucleic acid strand.

Steps (viii) to (x) may be repeated one or more times to incorporate one or more further coding sequences into the nucleic acid strand and couple the nucleic acid strand to one or more chemical moieties. For example, a nucleic strand may coupled to 3, 4, 5 or 6 or more chemical moieties.

A method may comprise repeating steps i) to iv), i) to vii) or i) to x) in series or in parallel using different first, second and/or further chemical moieties to produce a library comprising a diverse population of library members having different combinations of the first, second and further chemical moieties.

In some embodiments, n chemical moieties may be coupled to a nucleic acid strand as described above. The nth coding sequence (i.e. the coding sequence encoding the nth chemical moiety; the final chemical moiety to be coupled to the strand) may be incorporated into the nucleic acid strand by primer extension. A suitable method is shown in FIG. 3B.

For example, an identifier oligonucleotide comprising the nth coding sequence of a nucleic acid strand coupled to n chemical moieties (e.g. the second or further coding sequence) may be hybridised to the region adjacent the 3' end of the nucleic acid strand to produce a single-stranded 5' overhang of identifier oligonucleotide sequence that comprises the final coding sequence. The nucleic acid strand may then be extended 5' to 3' along the identifier oligonucleotide template to incorporate the complement of the final coding sequence into the extended nucleic acid strand. In some embodiments, the identifier oligonucleotide may be extended 5' to 3' along the nucleic strand to provide a second nucleic strand hybridised to the nucleic strand.

Suitable methods of 5' to 3' extension of nucleic acid strands along a template, for example using DNA polymerases and active fragments thereof, are well known in the art.

A sub-library produced as described above may comprise a diverse population of library members comprising different chemical moieties or different combinations of chemical moieties.

In some embodiments, a nucleic acid encoded chemical sub-library may display pharmacophores consisting of two or more chemical moieties that are coupled to a nucleic acid strand that includes coding sequences encoding the two or more chemical moieties. A suitable method is shown in FIG. 3A. For example, a method of producing a member of a nucleic acid encoded chemical library may comprise;

(i) providing a first diverse population of chemical moieties, (ii) coupling first nucleic acid strands to the diverse population of chemical moieties, (iii) contacting the first nucleic acid strands coupled to the chemical moieties with an adaptor oligonucleotide and an identifier oligonucleotide comprising a coding sequence, such that the adaptor oligonucleotide hybridizes to the nucleic acid strand and the identifier oligonucleotide to form a partially double-stranded complex, wherein each nucleic acid strand is contacted with an identifier oligonucleotide that comprises a coding sequence that encodes the chemical moiety coupled to the nucleic acid strand, and;

wherein all the nucleic acid strands are contacted with the same adaptor oligonucleotide, (iv) ligating the nucleic acid strands to the identifier oligonucleotides in the partially double-stranded complexes, such that the identifier oligonucleotides are incorporated into the nucleic acid strands, (v) coupling a diverse population of further chemical moieties to the first nucleic acid strands, (vi) contacting the first nucleic acid strands coupled to the further chemical moieties with a further adaptor and a further identifier oligonucleotide comprising a coding sequence, such that the further adaptor hybridizes to the nucleic acid strands and the identifier oligonucleotides to form partially double-stranded complexes, wherein each nucleic acid strand is contacted with a further identifier oligonucleotide that comprises a further coding sequence that encodes the further chemical moiety that is coupled to the nucleic acid strand, and;

wherein all the first nucleic acid strands are contacted with the same adaptor oligonucleotide, and (vii) ligating the nucleic acid strands to the further identifier oligonucleotides in the double-stranded complexes, such that the further coding sequence identifier oligonucleotides are incorporated into the nucleic acid strands.

(viii) optionally repeating steps (v) to (vii) one or more times, thereby producing a library member comprising first chemical moiety and one or more further chemical moieties, said moieties forming a pharmacophore for screening, and a nucleic acid strand comprising a first coding sequence which encodes the first chemical moiety and one or more further coding sequences which encode the one or more further chemical moieties.

In some embodiments, the adaptor and the further adaptor or further adaptors may have the same nucleotide sequence. In preferred embodiments, the adaptor and the further adaptor or further adaptors may have different nucleotide sequences.

Preferably, steps (v) to (vii) are repeated once, so that the sub-library comprises members having three chemical moieties and a nucleic acid strand comprising a first coding sequence which encodes the first chemical moiety, a second coding sequence which encodes the second chemical moiety and a third coding sequence which encodes the third chemical moiety.

Preferably, the first nucleic acid strands of the sub-library are hybridised with a second nucleic acid strand to produce a nucleic acid encoded chemical library for screening that comprises double-stranded nucleic acid.

The second nucleic acid strand may comprise spacers that correspond to the first, second and/or further coding sequences in the first nucleic acid strand, so that the same second nucleic acid strand may be hybridised to different first nucleic acid strands. In some embodiments, the second nucleic acid strand may be extended along the template of the first nucleic acid strand following hybridisation, such that it comprises the complement of one or more of the first, second and/or further coding sequences. In some embodiments, the second nucleic acid strand may not be coupled to chemical moieties.

In other embodiments, a sub-library of first nucleic acid strands coupled to first and second diverse populations of chemical moieties, and optionally third or more diverse populations of chemical moieties, as described above, may hybridise or self-assemble to a sub-library of second nucleic acid strands coupled to a further diverse population of chemical moieties, and optionally additional diverse population of chemical moieties, to produce a self-assembling library that displays pharmacophores formed by the chemical moieties that are coupled to both the first and second nucleic acid strands. Suitable self-assembling libraries may be produced by the methods shown in FIGS. 2A to 2E. For example, a nucleic acid encoded chemical library may be produced by a method comprising;

(i) providing a sub-library of first nucleic acid strands coupled to first and second diverse populations of chemical moieties ("first and second chemical moieties"), wherein each first nucleic acid strand comprises a first coding sequence which encodes the member of the first diverse population of chemical moieties that is coupled to the first nucleic acid strand, (ii) contacting the first nucleic acid strands with an adaptor oligonucleotide and first identifier oligonucleotides comprising coding sequences, such that the adaptor oligonucleotide hybridizes to the first nucleic acid strands and the first identifier oligonucleotides to form partially double-stranded complexes, wherein each first nucleic acid strand is contacted with a first identifier oligonucleotide comprising a coding sequence which encodes the member of the second population of chemical moieties that is coupled to the first nucleic acid strand, and;

wherein all the first nucleic acid strands in the sub-library are contacted with the same adaptor oligonucleotide, (iii) ligating the first nucleic acid strands to the first identifier oligonucleotides in the complexes, such that the second coding sequences are incorporated into the first nucleic acid strands;

(iv) contacting the first nucleic acid strands with a nucleic acid spacer strand, second identifier oligonucleotides, and a sub-library of second nucleic acid strands coupled to a third diverse population of chemical moieties ("third chemical moieties"), thereby forming partially double-stranded complexes, wherein each first nucleic acid strand is contacted with a second identifier oligonucleotide comprising a third coding sequence that encodes the member of the third population of chemical moieties that is coupled to the second nucleic acid strand, and;

wherein all the nucleic acid strands in the population are contacted with the same nucleic acid spacer strand, (v) ligating the first nucleic acid strand to the second identifier oligonucleotide such that the third coding sequence is incorporated into the nucleic acid strand; and, (vi) optionally ligating the second nucleic acid strand to the nucleic acid spacer strand, thereby producing a library comprising pharmacophores labelled with double-stranded nucleic acid molecules comprising first and second nucleic acid strands.

In another example, a nucleic acid encoded chemical library may be produced by a method comprising;

(i) providing a sub-library of first nucleic acid strands coupled to first and second diverse populations of chemical moieties ("first and second chemical moieties"), wherein each first nucleic acid strand comprises a first coding sequence which encodes the member of the first diverse population of chemical moieties that is coupled to the first nucleic acid strand, (ii) contacting the first nucleic acid strands with an adaptor oligonucleotide and first identifier oligonucleotides comprising coding sequences, such that the adaptor oligonucleotide hybridizes to the first nucleic acid strands and the first identifier oligonucleotides to form partially double-stranded complexes, wherein each first nucleic acid strand is contacted with a first identifier oligonucleotide comprising a coding sequence which encodes the member of the second population of chemical moieties that is coupled to the first nucleic acid strand, and;

wherein all the first nucleic acid strands in the sub-library are contacted with the same adaptor oligonucleotide, (iii) ligating the first nucleic acid strands to the first identifier oligonucleotides in the complexes, such that the second coding sequences are incorporated into the first nucleic acid strands;

(iv) contacting the first nucleic acid strands with a sub-library of second nucleic acid strands coupled to a third diverse population of chemical moieties ("third chemical moieties"), thereby forming partially double-stranded complexes, wherein each second nucleic acid strand comprises spacer regions at positions correspond to the first and second coding sequences in the first nucleic acid strand and a third coding sequence that encodes the member of the third population of chemical moieties that is coupled to the second nucleic acid strand; said third coding sequence forming a 5' overhang in the partially double-stranded complex, (v) extending the first nucleic acid strand along the second nucleic acid strand to incorporate the complement of the third coding sequence into the first nucleic acid strand; and, thereby producing a library comprising pharmacophores labelled with double-stranded nucleic acid molecules comprising first and second nucleic acid strands.

Each pharmacophore in the library is formed from the members of the first and second diverse populations of chemical moieties that are coupled to the first nucleic acid strand of a library member and the member of the third diverse population of chemical moieties that is coupled to the second nucleic acid strand of the library member.

The first nucleic acid strand of each library member comprises a first coding sequence that encodes the member of the first diverse population of chemical moieties that is coupled to the first nucleic acid strand, a second coding sequence encoding the member of the second diverse population of chemical moieties that is coupled to the first nucleic acid strand, and a third coding sequence encoding the member of the third diverse population of chemical moieties that is coupled to the second nucleic acid strand of the library member.

A suitable second nucleic acid strand for use in a method described above hybridises to the first nucleic acid strand and may comprise;
 a) a first hybridization portion which hybridizes to the first nucleic acid strand,
 b) a non-hybridizable spacer at a position that corresponds, when the first and second strands are hybridised together, to the position of the first coding sequence in the first nucleic acid strand; and
 c) a second hybridization portion which hybridizes to the first nucleic acid strand.

In some preferred embodiments, identical second nucleic acid strands may be coupled to all of the members of the third diverse population of chemical moieties.

A suitable nucleic acid spacer strand for use in a method described above hybridises to the first nucleic acid strand and may comprise;
 a) a first hybridization portion which hybridizes to the first nucleic acid strand,
 b) a non-hybridizable spacer at a position that corresponds, when the first nucleic acid strand and the nucleic acid spacer strand are hybridised together, to the position of the second coding sequence in the first nucleic acid strand
 c) a second hybridization portion which hybridizes to the first nucleic acid strand; and,
 d) a complementary annealing region which hybridizes to the second identifier oligonucleotide.

In some preferred embodiments, the same nucleic acid spacer strand may be used to produce all the members of the library i.e. all of the members may be produced using identical nucleic acid spacer strands.

A suitable second identifier oligonucleotide for use in a method described above hybridises to the nucleic acid spacer strand and may comprise;
 a) a first annealing region which hybridizes to the nucleic acid spacer strand,
 b) a third coding sequence encoding the member of the third diverse population of chemical moieties that is coupled to the second nucleic acid strand.

In some preferred embodiments, the same first annealing region may be used in all of the second identifier oligonucleotides that are used to produce the library i.e. all of the second identifier oligonucleotides may comprise an identical first annealing region. The diverse third coding sequences will necessarily be employed in the second identifier oligonucleotides, depending on the identity of the member of the third diverse population of chemical moieties that is coupled to a particular second nucleic acid strand.

Following each ligation step, the adaptor oligonucleotide may be removed by cleavage and/or purification, as described above.

The first and second chemical moieties may be coupled to one of the 5' end or the 3' end of the nucleic acid strand and the third chemical moiety may be coupled to the other of the 5' end or the 3' end of the partner strand of the library member. In some preferred embodiments, first and second chemical moieties may be coupled to the 5' end of the first nucleic acid strand and the third chemical moiety may be coupled to the 3' end of the second nucleic acid strand.

Self-assembly of the sub-library of first nucleic acid strands and the sub-library of second nucleic acid strands by hybridisation as described above produces an encoded self-assembly chemical library comprising a diverse population of library members displaying pharmacophores formed from different combinations of the first, second and third chemical moieties coupled to the first and second nucleic acid strands as shown in FIG. 2A to 2E.

The sub-library of first nucleic acid strands may be produced by a method comprising;
(i) providing a first nucleic acid strand having first and second chemical moieties coupled thereto,
wherein the nucleic acid strand comprises a first coding sequence which encodes the first chemical moiety,
(ii) contacting the nucleic acid strand with an adaptor oligonucleotide and a first identifier oligonucleotide comprising a second coding sequence that encodes the second chemical moiety,
such that the adaptor oligonucleotide hybridizes to the nucleic acid strand and the identifier oligonucleotide to form a partially double-stranded complex,
(iii) ligating the nucleic acid strand to the first identifier oligonucleotide in the complex, such that the second coding sequence is incorporated into the nucleic acid strand; and,
(iv) repeating steps (i) to (iii) in series or in parallel to using different first and second chemical moieties and first and second coding sequences and the same adaptor oligonucleotide to produce a diverse population of pairs of first and second chemical moieties coupled to first nucleic acid strands,
each pair of chemical moieties being coupled to a first nucleic acid strand which comprises a first coding sequence encoding the first chemical moiety and a second coding sequence encoding the second chemical moiety coupled thereto.

Examples of suitable methods are shown in FIGS. 2A, 2C and 2D.

The diverse population of pairs of first and second chemical moieties coupled to first nucleic acid strands produced by step v) may then be combined or pooled into a single diverse population or sub-library.

In some embodiments, the sub-library of first nucleic acid strands may be hybridised with a sub-library of second nucleic acid strands that comprise spacer regions and a third coding sequence.

The sub-library of second nucleic acid strands may be produced by a method comprising;
(i) providing a second nucleic acid strand having a third chemical moiety coupled thereto,
wherein the second nucleic acid strand comprises a first spacer region at a position corresponding to the first coding sequence in the first nucleic acid strand,
(ii) contacting the second nucleic acid strand with an adaptor oligonucleotide and a nucleic acid spacer strand comprising a second spacer region at a position corresponding to the second coding sequence in the first nucleic acid strand,
such that the adaptor oligonucleotide hybridizes to the second nucleic acid strand and the nucleic acid spacer strand to form a partially double-stranded complex,
(iii) ligating the second nucleic acid strand to the nucleic acid spacer strand in the complex, such that the second spacer region is incorporated into the second nucleic acid strand;
(iv) contacting the second nucleic acid strand with an adaptor oligonucleotide and a second identifier oligonucleotide comprising a third coding sequence that encodes the third chemical moiety,
such that the adaptor oligonucleotide hybridizes to the second nucleic acid strand and the second identifier oligonucleotide to form a partially double-stranded complex,
(v) ligating the second nucleic acid strand to the second identifier oligonucleotide in the complex, such that the third coding sequence is incorporated into the second nucleic acid strand;
(vi) repeating steps (i) to (v) in series or in parallel using different third chemical moieties and third coding sequences and the same adaptor oligonucleotide to produce a diverse population of third chemical moieties coupled to second nucleic acid strands,
each third chemical moiety being coupled to a second nucleic acid strand which comprises first and second spacer regions and a third coding sequence encoding the third chemical moiety coupled thereto.

An example of a suitable method is shown in FIG. 2D.

The third coding sequence (i.e. the coding sequence encoding the third chemical moiety) from the second nucleic acid of the members of the library or its complement may be incorporated into the first nucleic acid strand of the members by primer extension. A method may comprise;
(vii) contacting the sub-library of first nucleic acid strands to the sub-library of second nucleic acid strands,
the second nucleic acid strand hybridising to the first nucleic acid strand to form a double-stranded complex having a 5' overhang comprising the third coding sequence,
(viii) extending the first nucleic acid strand along the second nucleic acid strand to incorporate the complement of the third coding sequence into the first nucleic acid strand;
thereby producing library in which each member comprises a pharmacophore formed by the first and second chemical moieties coupled to the first nucleic acid strand and the third chemical moiety coupled to the second nucleic acid strand; wherein the first nucleic acid strand comprises first, second and third coding sequences that encode the first, second and third chemical moieties, respectively.

An example of a suitable method is shown in FIG. 2E.

In other embodiments, a separate identifier oligonucleotide comprising the third coding sequence may be employed. A method may comprise;
(vi) splitting the sub-library of first nucleic acid strands into pools;
(vii) contacting a pool of the sub-library with a second nucleic acid strand coupled to a third chemical moiety, a nucleic acid spacer strand and a second identifier oligonucleotide comprising a third coding sequence that encodes the third chemical moiety that is coupled to the second nucleic acid strand, the second nucleic acid strand and the nucleic acid spacer strand hybridising to the first nucleic acid strand and the second identifier oligonucleotide to form a partially double-stranded complex, wherein the second identifier oligonucleotide comprises a third coding sequence that encodes the third chemical moiety that is coupled to the second nucleic acid strand, (viii) ligating the nucleic acid strands to the second identifier oligonucleotide such that the third coding sequence is incorporated into the first nucleic acid strand;

(ix) optionally ligating the second nucleic acid strand to the nucleic acid spacer strand, (x) repeating steps vi) to ix) in series or in parallel using different third chemical moieties and third coding sequences, wherein second nucleic acid strands and nucleic acid spacer strands having the same nucleotide sequence are used for more than one different third chemical moiety and second identifier oligonucleotide, to produce multiple pools of the first nucleic acid strands, the first nucleic strands in each pool being hybridised to second nucleic acid strands coupled to different third chemical moieties, and (xi) combining the pools into a single diverse population or library, each member of the library comprising a pharmacophore formed by the first and second chemical moieties coupled to the first nucleic acid strand and the third chemical moiety coupled to the second nucleic acid strand; wherein the first nucleic acid strand comprises first, second and third coding sequences that encode the first, second and third chemical moieties, respectively.

An example of a suitable method is shown in FIG. 2A.

Preferably, identical second nucleic acid strands and nucleic acid spacer strands are used in all of the repetitions of step (x).

In some embodiments, the first, second or further adaptor oligonucleotide may be removed following each ligation step. For example, the adaptor oligonucleotide may be removed by purification and/or fragmentation, as described above.

The third coding sequence (i.e. the coding sequence encoding the third chemical moiety) may be incorporated into the first nucleic acid strand by primer extension, for example as set out in FIG. 2C. A method may comprise;

(vi) splitting the sub-library of first nucleic acid strands into pools;

(vii) contacting a pool of the sub-library with a second nucleic acid strand coupled to a third chemical moiety, a nucleic spacer strand and a second identifier oligonucleotide comprising a third coding sequence that encodes the third chemical moiety that is coupled to the second nucleic acid strand, the second nucleic acid strand, nucleic spacer strand and second identifier oligonucleotide hybridising to the first nucleic acid strand to form a double-stranded complex having a 5' overhang comprising the third coding sequence, (viii) extending the first nucleic acid strand along the second identifier oligonucleotide to incorporate the complement of the third coding sequence into the first nucleic acid strand;

(ix) optionally ligating the second nucleic acid strand to the nucleic acid spacer strand and second identifier oligonucleotide, (x) repeating steps vi) to ix) in series or in parallel using different third chemical moieties and third coding sequences, wherein second nucleic acid strands and nucleic acid spacer strands having the same nucleotide sequence are used for more than one different third chemical moiety and second identifier oligonucleotide, to produce multiple pools of first nucleic acid strands, the first nucleic strands in each pool comprising different third coding sequences and being hybridised to second nucleic acid strands coupled to different third chemical moieties, and (xi) combining the pools into a single diverse population or library, each member of the library comprising a pharmacophore formed by the first and second chemical moieties coupled to the first nucleic acid strand and the third chemical moiety coupled to the second nucleic acid strand; wherein the first nucleic acid strand comprises first, second and third coding sequences that encode the first, second and third chemical moieties, respectively.

In other embodiments, the adaptor oligonucleotide forms part of a nucleic acid spacer strand that remains hybridised to the first nucleic acid strand and is optionally ligated to the second nucleic acid strand. A nucleic acid encoded chemical library may be produced by a method comprising;

(i) providing a sub-library of first nucleic acid strands coupled to first and second diverse populations of chemical moieties ("first and second chemical moieties"), wherein each first nucleic acid strand comprises a first coding sequence which encodes the member of the first diverse population of chemical moieties that is coupled to the first nucleic acid strand, (ii) contacting the first nucleic acid strands with first identifier oligonucleotides comprising second coding sequences and one or more nucleic acid spacer strands, such that the first nucleic acid spacer strands hybridize to the first nucleic acid strands and the first identifier oligonucleotides to form partially double-stranded complexes, wherein each first nucleic acid strand is contacted with a first identifier oligonucleotide comprising a second coding sequence which encodes the member of the second population of chemical moieties that is coupled to the first nucleic acid strand, and;

each nucleic acid spacer strand hybridises to more than one different first identifier oligonucleotide and first nucleic acid strands coupled to more than one different second chemical moiety, (iii) ligating the first nucleic acid strands to the first identifier oligonucleotides in the complexes, such that the second coding sequences are incorporated into the first nucleic acid strands;

(v) contacting the first nucleic acid strands hybridised to the nucleic acid spacer strand with a sub-library of second nucleic acid strands coupled to a third diverse population of chemical moieties ("third chemical moieties") and second identifier oligonucleotides, thereby forming double-stranded complexes, wherein each first nucleic acid strand is contacted with a second identifier oligonucleotide that comprises a third coding sequence that encodes the member of the third population of chemical moieties that is coupled to the second nucleic acid strand that is contacted therewith, and;
(vi) ligating the first nucleic acid strand to the second identifier oligonucleotide such that the third coding sequence is incorporated into the first nucleic acid strand; and,
(vii) optionally ligating the second nucleic acid strand to the nucleic acid spacer strand,
thereby producing a library comprising pharmacophores formed by the first and second chemical moieties coupled to the first nucleic acid strand and the third chemical moiety coupled to the second nucleic acid strand; wherein the first nucleic acid strand comprises first, second and third coding sequences that encode the first, second and third chemical moieties, respectively.

An example of a suitable method is shown in FIG. 2B.

Preferably, all the first nucleic acid strands in the sub-library are contacted with an identical nucleic acid spacer strand.

Suitable second nucleic acid strands are described above.

Preferably, identical second nucleic acid strands are coupled to all of the members of the third diverse population of chemical moieties.

A suitable nucleic acid spacer strand hybridises to the first nucleic acid strand and may comprise;
a) a first hybridization portion which hybridizes to the first nucleic acid strand,
b) a first non-hybridizable spacer at a position that corresponds, when the first nucleic acid strand and the nucleic acid spacer strand are hybridised together, to the position of the second coding sequence in the first nucleic acid strand
c) a second hybridization portion which hybridizes to the first nucleic acid strand;
d) a first annealing region which hybridizes to the second identifier oligonucleotide,
e) a second non-hybridizable spacer at a position that corresponds, when the second identifier oligonucleotide and the nucleic acid spacer strand are hybridised together, to the position of the third coding sequence in the second identifier oligonucleotide and;
f) a second annealing region which hybridizes to the second identifier oligonucleotide.

In some preferred embodiments, the same nucleic acid spacer strand sequence may be used to produce all the members of the library i.e. all of the members may be produced using identical nucleic acid spacer strands.

A suitable second identifier oligonucleotide for use in a method described above hybridises to the nucleic acid spacer strand and may comprise;
a) a first complementary annealing region which hybridizes to the nucleic acid spacer strand,
b) a third coding sequence encoding the member of the third diverse population of chemical moieties that is coupled to the second nucleic acid strand and;
a) a second complementary annealing region which hybridizes to the nucleic acid spacer strand.

In some preferred embodiments, all of the second identifier oligonucleotides that are used to produce the library may comprise the same first and second complementary annealing regions i.e. all of the second identifier oligonucleotides may comprise an identical first and second annealing regions. This allows identical nucleic acid spacer strands to be used for all second identifier oligonucleotides. Diverse third coding sequences will necessarily be employed in the second identifier oligonucleotides, depending on the identity of the member of the third diverse population of chemical moieties that is coupled to a particular second nucleic acid strand.

As described above, in some embodiments, a sub-library of second nucleic acid strands comprising one or more nucleic acid spacer strands and second identifier oligonucleotide sequences may be produced before hybridisation to the sub-library of first nucleic acid strands. In other embodiments, one or more nucleic acid spacer strands and second identifier oligonucleotide sequences may be ligated to the second nucleic acid strands after hybridisation to the first nucleic acid strands.

As described above, self-assembly of the sub-library of first nucleic acid strands and the sub-library of second nucleic acid strands by hybridisation as described above produces an encoded self-assembly chemical library comprising a diverse population of library members displaying pharmacophores formed from different combinations of the first, second and third chemical moieties coupled to the first and second nucleic acid strands.

The sub-library of first nucleic acid strands may be produced by a method comprising;
(i) providing a first nucleic acid strand having first and second chemical moieties coupled thereto, wherein the nucleic acid strand comprises a first coding sequence which encodes the first chemical moiety,
(ii) contacting the nucleic acid strand with a nucleic acid spacer strand and a first identifier oligonucleotide comprising a second coding sequence that encodes the second chemical moiety,
such that the nucleic acid spacer strand hybridizes to the nucleic acid strand and the first identifier oligonucleotide to form a partially double-stranded complex,
(iii) ligating the nucleic acid strand to the first identifier oligonucleotide in the complex, such that the second coding sequence is incorporated into the nucleic acid strand in the complex; and,
(iv) repeating steps (i) to (iii) in series or in parallel using different first and second chemical moieties and first and second coding sequences, wherein each nucleic acid spacer strand hybridises to first nucleic acid strands coupled to more than one combination of first and second chemical moieties and first identifier oligonucleotides comprising more than one different second coding sequence, to produce a diverse population of pairs of first and second chemical moieties coupled to first nucleic acid strands,
each pair of chemical moieties being coupled to a first nucleic acid strand which comprises a first coding sequence encoding the first chemical moiety and a second coding sequence encoding the second chemical moiety coupled thereto, the nucleic acid spacer strand being hybridised to the first nucleic acid strand.

Suitable methods are illustrated in FIG. 2B.

Preferably, an identical nucleic acid spacer strand is used in each repetition of step (iv).

In some embodiments, the nucleic acid spacer strand remains hybridised to the first nucleic acid strand.

In other embodiments, the nucleic acid spacer strand may be removed, for example, by denaturation and purification, and then rehybridised to the first nucleic acid strand.

The diverse population of pairs of first and second chemical moieties coupled to first nucleic acid strand/nucleic acid spacer strand complexes, as produced by step (iv), may then be combined or pooled into a single sub-library.

A method may comprise;
(vi) splitting the sub-library of first nucleic acid strands and nucleic acid spacer strand complexes into pools;
(vii) contacting a pool of the sub-library with a second nucleic acid strand coupled to a third chemical moiety and a second identifier oligonucleotide comprising a third coding sequence that encodes the third chemical moiety, thereby forming a double-stranded complex comprising the first and second nucleic acid strands, the nucleic acid spacer strand, the second identifier oligonucleotide and the first, second and third chemical moieties,
wherein the second identifier oligonucleotide comprises a third coding sequence that encodes the third chemical moiety that is coupled to the second nucleic acid strand,
(viii) ligating the first nucleic acid strands to the second identifier oligonucleotide such that the third coding sequence is incorporated into the first nucleic acid strand;
(ix) optionally ligating the second nucleic acid strand to the nucleic acid spacer strand,
(x) repeating steps vi) to ix) in series or in parallel using different third chemical moieties and third coding sequences, and identical second nucleic acid strands and nucleic acid spacer strands, thereby producing a library of diverse pharmacophores,
wherein each nucleic acid spacer strand hybridises to second nucleic acid strands that are coupled to more than one different third chemical moiety and second identifier oligonucleotides that comprise more than one different third coding sequence,
each member of the library comprising a pharmacophore formed by the first and second chemical moieties coupled to the first nucleic acid strand and the third chemical moiety coupled to the second nucleic acid strand; wherein the first nucleic acid strand comprises first, second and third coding sequences that encode the first, second and third chemical moieties, respectively.

Preferably, nucleic acid spacer strands having identical nucleotide sequences are used for each repetition of step (x).

Suitable methods are illustrated in FIG. 2B.

Libraries produced by the methods described above may comprise 500 or more, 1000 or more, 10000 or more, 100000 or more or 1000000 or more different library members, each different member displaying a different pharmacophore formed from a different combination of chemical moieties.

Once the encoded chemical library members have been synthesised as described above, they can be combined into an encoded chemical library, for example by including the library members together in a single vessel or single reaction mixture. This facilitates screening of the chemical library.

Another aspect of the invention provides a method of generating a nucleic acid encoded chemical library comprising;
producing multiple diverse library members using a method described above and
combining the library members to produce a chemical library.

Within a chemical library, members may include nucleic acid strands which are coupled to the same number and type of chemical moiety but which are linked in a different order to each nucleic acid strand. For example, where a nucleic acid strand is coupled to two chemical moieties, A and B, some nucleic acid strands may include the moieties linked in the order A-B, where A is distal to the nucleic acid strand and B is proximal to the nucleic acid strand, while others may contain the same two chemical moieties linked in the order B-A where B is distal to the nucleic acid strand and A is proximal to the nucleic acid strand. Assembly of each of these strands individually with a partner strand coupled to a single moiety 'C' will produce two library members having pharmacophores with different structures, even though they are composed of the same chemical moieties.

The same principle applies to chemical library members which include three chemical moieties, A', B' and C', where members may include the moieties linked as A'-B'-C', A'-C'-B', B'-A'-C', B'-C'-A', C'-A'-B' and/or C'-B'-A' (ordered as proximal-middle-distal with respect to the nucleic acid strand in each case). Other arrangements of chemical moieties are possible, for example A' and B' may both be linked to C' but not to each other, or all of A', B' and C' may form a covalently linked compound.

The same principle applies to chemical library members having four, five or more chemical moieties. Thus, it can be seen that the number of combinations of chemical moieties in the pharmacophore is increased which can aid selection.

The number of different members in a chemical library represents the complexity of a library and is defined by number of different chemical moieties, the number of chemical moieties in each pharmacophore, and therefore the number of different pharmacophores in the library. The number of different pharmacophores of any particular library can be determined by multiplying the number of different types of chemical moieties together. For example, if each library member has two chemical moieties in the pharmacophore, and there are twenty types of each chemical moiety, then the resulting library has 400 members. If, for example, there are three chemical moieties in the pharmacophore, each of which has twenty variants, then the resulting library has 8000 members.

The relative amounts of the individual chemical moieties within the library can vary from about 0.2 equivalents to about 10 equivalents, where an equivalent represents the average amount of a chemical moiety within the library. Preferably each chemical moiety is present in the library in approximately equimolar amounts.

If desired, the members of a chemical library may be linked to a solid support such as a bead, array or other substrate surface. Alternatively the library members can be free in solution.

One exemplary use for a chemical library is for lead optimization. Lead optimization may involve combining a known pharmacophore, formed from one or more chemical moieties with one or more further chemical moieties, as described herein with the aim of improving the characteristics of the known pharmacophore, for example the binding affinity. In this case, nucleic acid strands from a first and second sub-library may be hybridized to form a library. The first sublibrary may comprise library members which are coupled to the known pharmacophore and the second sub-library comprises members coupled to one or more candidate chemical moieties. The second sublibrary generally comprises a variety of different chemical moieties, because this increases the variety of structure in the pharmacophores of the assembled library members. The identities of the chemical moieties in the resultant pharmacophore are encoded into the library member using the methods described herein.

An encoded chemical library generated according to the methods of the present invention provides a repertoire of chemical diversity in which each chemical moiety is linked to a identifier oligonucleotide that facilitates identification of the chemical moiety. The library may be used to screen for pharmacophores with particular properties, e.g. pharmacophores that bind a target molecule e.g. a protein. By screening an encoded chemical library, it is possible to identify optimised chemical structures that participate in binding interactions with a biological macromolecule by drawing upon a repertoire of structures randomly formed by the association of diverse chemical moieties without the necessity of either synthesising them one at a time or knowing their interactions in advance.

Encoded chemical libraries produced as described herein may be used in a variety of such methods. For example, the library can be used in a method for identifying a pharmacophore that participates in a preselected binding interaction with a biological macromolecule.

A method for identifying a pharmacophore which binds to a target of interest comprises the following steps:
  (a) admixing a chemical library produced as described above with a preselected biological macromolecule under binding conditions (i.e., a binding reaction admixture) for a time period sufficient for the biological macromolecule to interact with the library and form a binding reaction complex with at least one member thereof;
  (b) isolating the binding reaction complex from the library admixture to form an isolated complex;
  (c) determining the coding sequences of the nucleic acid moieties present in the isolated binding reaction complex,
thus identifying the chemical moieties that participated in the binding reaction.

A typical biological macromolecule exhibiting a preselected binding interaction can be any of a variety of molecules (e.g. proteins) that bind selectively to another molecule, including antibodies to antigens, lectins to oligosaccharides, receptors to ligands, enzymes to substrates and the like mediators of molecular interactions. Therefore, a preselected binding interaction is defined by the selection of the biological macromolecule with which a library member is to bind.

The assembly of double-stranded libraries displaying pharmacophores formed from chemical moieties on each of the strands allows the production of libraries containing large numbers of different pharmacophores. For example, a method for producing a nucleic acid encoded chemical library may comprise,
  (i) producing a first diverse population (A) of one or more chemical moieties coupled to first nucleic acid strands using a method described above,
  (ii) producing a second diverse population (B) of one or more chemical moieties coupled to second nucleic acid strands using a method described above,
  wherein the first nucleic acid strands hybridise to the second nucleic acid strands to form library members, such that the chemical moieties coupled to the first and second nucleic acid strands of each library member form a pharmacophore,
  (iii) combining the first and second diverse populations to produce a library of library members comprising a double-stranded nucleic acid molecule (A×B).

As described above, the first and second nucleic acid strands may comprise one or more regions which are complementary to each other allowing self-assembly when the diverse populations are combined.

Another aspect of the invention provides a nucleic acid encoded chemical library comprising library members produced by a method described above.

Another aspect of the invention provides a method of screening a nucleic acid encoded chemical library comprising;
  producing a nucleic acid encoded chemical library using a method described above,
  contacting the library with a target molecule and
  selecting one or more library members which bind to the target.

The target molecule is a molecule which the pharmacophore is a candidate for interacting with. The target molecule may be a biological molecule as described herein or any other molecule of interest.

The library is contacted with a target molecule under binding conditions for a time period sufficient for the target molecule to interact with the library and form a binding reaction complex with a least one member thereof.

Binding conditions are those conditions compatible with the known natural binding function of the target molecule. Those compatible conditions are buffer, pH and temperature conditions that maintain the biological activity of the target molecule, thereby maintaining the ability of the molecule to participate in its preselected binding interaction. Typically, those conditions include an aqueous, physiologic solution of pH and ionic strength normally associated with the target molecule of interest.

For example, where the binding interaction is to identify a member in the library able to bind an antibody molecule, the preferred binding conditions would be conditions suitable for the antibody to immunoreact with its immunogen, or a known immunoreacting antigen. For a receptor molecule, the binding conditions would be those compatible with measuring receptor ligand interactions.

A time period sufficient for the admixture to form a binding reaction complex is typically that length of time required for the biological macromolecule to interact with its normal binding partner under conditions compatible with interaction. Although the time periods can vary depending on the molecule and its respective concentration, admixing times are typically for at least a few minutes, and usually not longer than several hours, although nothing is to preclude using longer admixing times for a binding reaction complex to form.

A binding reaction complex is a stable product of the interaction between a target molecule and a pharmacophore as described herein. The product is referred to as a stable product in that the interaction is maintained over sufficient time that the complex can be isolated from the rest of the members of the library without the complex becoming significantly disassociated.

The admixture of a library of the invention with a target molecule can be in the form of a heterogeneous or homogeneous admixture. Thus, the members of the library can be in the solid phase with the target molecule present in the liquid phase. Alternatively, the target molecule can be in the solid phase with the members of the library present in the liquid phase. Still further, both the library members and the target molecule can be in the liquid phase.

The selected library members may be isolated and/or purified.

A binding reaction complex may be isolated from the binding reaction admixture by any separation means that is selective for the complex, thereby isolating that library member, or members, which has/have bound to the target. There are a variety of separation means, depending on the status of the target.

For example, a target which is a biological macromolecule may be provided in admixture in the form of a solid phase reagent, i.e., affixed to a solid support, and thus can readily be separated from the liquid phase, thereby removing the majority of library members. Separation of the solid phase from the binding reaction admixture can optionally be accompanied by washes of the solid support to rinse library members having lower binding affinities off the solid support.

Alternatively, for a homogeneous liquid binding reaction admixture, a secondary binding means specific for the biological macromolecule can be utilized to bind the molecule and provide for its separation from the binding reaction admixture.

For example, an immobilised antibody immunospecific for the biological macromolecule can be provided as a solid phase-affixed antibody to the binding reaction admixture after the binding reaction complex is formed. The immobilised antibody immunoreacts with the biological macromolecule present in the binding reaction admixture to form an antibody-biological macromolecule immunoreaction complex. Thereafter, by separation of the solid phase from the binding reaction admixture, the immunoreaction complex, and therefore any binding reaction complex, is separated from the admixture to form isolated library member.

Alternatively, a binding means can be operatively linked to target molecule to facilitate its retrieval from the binding reaction admixture. Exemplary binding means are one of the following high affinity pairs: biotin-avidin, protein A-Fc receptor, ferritin-magnetic beads, and the like. Thus, the target is operatively linked (conjugated) to biotin, protein A, ferritin and the like binding means, and the binding reaction complex is isolated by the use of the corresponding binding partner in the solid phase, e.g., solid-phase avidin, solid-phase Fc receptor, solid phase magnetic beads and the like.

The use of solid supports on which to operatively link proteinaceous molecules is generally well known in the art. Useful solid support matrices are well known in the art and include cross-linked dextran such as that available under the tradename SEPHADEX from Pharmacia Fine Chemicals (Piscataway, N.J.); agarose, borosilicate, polystyrene or latex beads about 1 micron to about 5 millimeters in diameter, polyvinyl chloride, polystyrene, cross-linked polyacrylamide, nitrocellulose or nylon-based webs such as sheets, strips, paddles, plates microtiter plate wells and the like insoluble matrices.

The nucleic acid strand or the partner nucleic acid strand of the selected library members may be sequenced to identify the chemical moieties that form the pharmacophore displayed by the selected library members.

The identifier oligonucleotides of the library members that bind to the target molecules may be amplified by PCR, which allows very low amounts of template nucleic acid to be detected. Subsequent decoding of the enriched nucleic acid uses either nucleic acid sequencing or hybridisation to oligonucleotide microarrays, depending on the architecture of the library and its size.

A preferred method for decoding is the use of high throughput sequencing methods, such as the 454-Roche Genome Sequencer system. For sequencing with the 454-Roche Genome Sequencer system, PCR products have to contain suitable adaptor sequences at their extremities (called adaptor sequence A and B), which can be either added after a PCR reaction by ligation, or they can be incorporated in the PCR reactions, if the PCR primers contain on their 5'-ends sequences corresponding to an adaptor region. The next step of a particular sequencing process is the annealing of PCR amplicons on nucleic acid Capture Beads, emulsification of beads and PCR reagents in water-in-oil microreactors, and clonal emPCR amplification inside these microreactors. After breaking of the emulsion, the Capture beads are mixed with Enzyme Beads, and loaded on a PicoTiterPlate. Pyrosequencing allows the recording of individual sequences for each nucleic acid species displayed at Capture Beads, trapped in the wells of PicoTiterPlates. This allows the parallel sequencing of a vast amount (typically more than 100,000 per PicoTiterPlate) of individual nucleic acid species at a time. With further improvement of the sequencing technology, it will be possible to sequence more than 1,000,000 individual nucleic acid species at a time.

Further details and examples of the use of library screening techniques have been described in the art [1] to [9].

Suitable primers may be primers which bind to primer regions in the nucleic acid strand or partner strand.

Various further aspects and embodiments of the present invention will be apparent to those skilled in the art in view of the present disclosure.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described below.

FIG. 1A shows an encoding strategy for a chemical library member using a chimeric cleavable adaptor as described herein. In this scheme, a nucleic acid strand is first coupled to a chemical moiety (or 'building block'). The nucleic acid strand contains a non-coding spacer region. A cleavable chimeric adaptor is used to couple an identifier oligonucleotide to the distal end of the nucleic acid strand with respect to the moiety. The identifier oligonucleotide contains a coding sequence (codeB) which encodes the identity of the chemical moiety attached to the nucleic acid strand. The adaptor hybridizes to complementary bases on the distal end of the nucleic acid strand and proximal end of the identifier oligonucleotide. This brings an end of the identifier oligonucleotide into proximity to an end of the nucleic acid strand, such that ligation can occur under suitable conditions. The ends of the identifier oligonucleotide and nucleic acid strand are then ligated and the adaptor is removed. A partner nucleic acid strand is then hybridized to the first nucleic acid strand. The partner nucleic acid strand is coupled to a further chemical moiety and includes an identifier oligonucleotide containing a coding sequence (codeA) encoding the identity of its chemical moiety. The nucleotide sequence of the partner stand is then extended by polymerase-mediated fill-in so that the coding sequence encoding the identity of the first chemical moiety is located on the same strand as the coding sequence for the second chemical moiety, in this case the partner strand.

The encoded chemical library member, which contains a pharmacophore comprising two chemical moieties, can then be used for selection experiments on a target of interest. Following selection, candidate chemical library members are decoded by PCR amplification of the partner nucleic acid strand, which contains the coding sequences of both chemical moieties. The spacer region located in the nucleic acid strand prevents amplification of this strand.

FIG. 1B shows an alternative strategy to that described in FIG. 2A. Here, the adaptor is used to couple an identifier oligonucleotide containing a coding sequence to the nucleic acid strand before the chemical moiety encoded by the coding sequence is coupled to the nucleic acid strand. Construction of the encoded library member then proceeds as in FIG. 1A.

FIG. 2A shows an encoding strategy for the production of a three building block pharmacophore library in which the building blocks are coupled to both strands of the members. A nucleic acid strand is first coupled to first and second chemical moieties ('building blocks'). The nucleic acid strand contains coding sequence (codeA) encoding the first chemical moiety. A cleavable chimeric adaptor is used to couple an identifier oligonucleotide to the distal end of the nucleic acid strand with respect to the moieties. The identifier oligonucleotide contains a coding sequence (codeB) which encodes the identity of the second chemical moiety attached to the nucleic acid strand. The adaptor hybridizes to complementary bases on the distal end of the nucleic acid strand and proximal end of the identifier oligonucleotide forming a complex between identifier oligonucleotide, nucleic acid strand and adaptor. This brings an end of the identifier oligonucleotide into proximity to an end of the nucleic acid strand, such that ligation can occur under suitable conditions. The ends of the identifier oligonucleotide and nucleic acid strand are then ligated and the adaptor is removed. The nucleic acid strand is then contacted with a partner nucleic acid strand, a nucleic acid spacer strand and a second identifier oligonucleotide to form a complex. The partner nucleic acid strand is coupled to a third chemical moiety. The partner nucleic acid strand hybridizes to the nucleic acid strand thought complementary regions and includes a spacer region which does not hybridize to a coding region (codeA) of the nucleic acid strand. The nucleic acid spacer strand also hybridises to the nucleic acid strand and includes a spacer region which does not hybridize to the further coding region (codeB) of the nucleic acid strand. The second identifier oligonucleotide contains a coding sequence (codeC) encoding the identity of the third chemical moiety. The second identifier oligonucleotide hybridises to complementary regions on the nucleic acid spacer tag. The second identifier oligonucleotide is then ligated to the nucleic acid strand and the nucleic acid spacer strand is ligated to the partner nucleic acid strand. Coding information for all three chemical moieties in the pharmacophore is now encoded on the nucleic acid strand.

FIG. 2B shows an alternative strategy for the production of a three building block pharmacophore library in which the building blocks are coupled to both strands of the members.

Here, a nucleic acid strand is first coupled to first and second chemical moieties ('building blocks'). The nucleic acid strand contains a first coding sequence (codeA) encoding a first chemical moiety. The nucleic acid strand is then contacted with a nucleic acid spacer strand and a first identifier oligonucleotide to form a complex. The first identifier oligonucleotide contains a second coding sequence encoding the identity of the second chemical moiety. The nucleic acid spacer strand contains first and second non-hybridizable spacer regions at a position in the nucleic acid spacer strand corresponding to the position of the second coding sequence in and a further, third coding sequence in the nucleic acid strand. The nucleic acid spacer strand hybridizes to the nucleic acid strand and first identifier oligonucleotide through complementary regions. The nucleic acid strand is then ligated to the first identifier oligonucleotide. The complex comprising the nucleic acid spacer strand and nucleic acid strand is then contacted with a second identifier oligonucleotide and partner nucleic acid strand, which hybridize through complementary regions to form a complex. In the complex each coding region is located in a position corresponding to a non-hybridizable spacer region. The partner nucleic acid strand is coupled to a third chemical moiety and contains a spacer region at a position in the nucleic acid partner strand corresponding to the position of the first coding sequence in the nucleic acid strand. The second identifier oligonucleotide contains a third coding sequence encoding the identity of the third chemical moiety.

The partner nucleic acid strand may be ligated to the nucleic acid spacer strand and the second identifier oligonucleotide is ligated to the nucleic acid strand.

FIG. 2C shows an alternative strategy for the production of a three building block pharmacophore library in which the building blocks are coupled to both strands of the members.

A nucleic acid strand is first coupled to first and second chemical moieties ('building blocks'). The nucleic acid strand contains coding sequence (codeA) encoding the first chemical moiety. A cleavable chimeric adaptor is used to couple an identifier oligonucleotide to the distal end of the nucleic acid strand with respect to the moieties. The identifier oligonucleotide contains a coding sequence (codeB) which encodes the identity of the second chemical moiety attached to the nucleic acid strand. The adaptor hybridizes to complementary bases on the distal end of the nucleic acid strand and proximal end of the identifier oligonucleotide forming a complex between identifier oligonucleotide, nucleic acid strand and adaptor. This brings an end of the identifier oligonucleotide into proximity to an end of the nucleic acid strand, such that ligation can occur under suitable conditions. The ends of the identifier oligonucleotide and nucleic acid strand are then ligated and the adaptor is removed. The nucleic acid strand is then contacted with a partner nucleic acid strand, a nucleic acid spacer strand and a second identifier oligonucleotide to form a complex. The partner nucleic acid strand is coupled to a third chemical moiety. The partner nucleic acid strand hybridizes to the nucleic acid strand through complementary regions and includes a spacer region which does not hybridize to a coding region (codeA) of the nucleic acid strand. The nucleic acid spacer strand also hybridises to the nucleic acid strand and includes a spacer region which does not hybridize to the further coding region (codeB) of the nucleic acid strand. The second identifier oligonucleotide contains a coding sequence (codeC) encoding the identity of the third chemical moiety. The proximal end of the second identifier oligonucleotide hybridises to complementary regions at the distal end of the nucleic acid strand to produce a 5' overhang that contains the coding sequence (codeC). The nucleic acid strand is then extended along the second identifier oligonucleotide using a polymerase. The second identifier oligonucleotide may be ligated to the nucleic acid strand and the nucleic acid spacer strand. Coding information for all three chemical moieties in the pharmacophore is now encoded on the nucleic acid strand.

FIGS. 2D and 2E shows another alternative strategy for the production of a three building block pharmacophore library in which the building blocks are coupled to both strands of the members.

A nucleic acid strand is first coupled to first and second chemical moieties ('building blocks'). The nucleic acid strand contains a first coding sequence (codeA) encoding the first chemical moiety. A cleavable chimeric adaptor is used to couple an identifier oligonucleotide to the distal end of the nucleic acid strand with respect to the moieties. The identifier oligonucleotide contains a second coding sequence (codeB) which encodes the identity of the second chemical moiety attached to the nucleic acid strand. The adaptor hybridizes to complementary bases on the distal end of the nucleic acid strand and proximal end of the identifier oligonucleotide forming a complex between identifier oligonucleotide, nucleic acid strand and adaptor. This brings an end of the identifier oligonucleotide into proximity to an end of the nucleic acid strand, such that ligation can occur under suitable conditions. The ends of the identifier oligonucleotide and nucleic acid strand are then ligated and the adaptor is removed.

A partner nucleic acid strand is coupled to a third chemical moiety. The partner nucleic acid strand contains a first spacer region (d-spacer) at a position corresponding to the first coding sequence (codeA) of the nucleic acid strand. The first spacer region does not hybridize to the first coding sequence (codeA).

A first cleavable chimeric adaptor is used to couple a nucleic acid spacer strand to the distal end of the partner nucleic acid strand with respect to the third chemical moiety. The nucleic acid spacer strand is capable of hybridizing to the nucleic acid strand and contains a second spacer region (d-spacer II) at a position corresponding to the second coding sequence (codeB) of the nucleic acid strand. The second spacer region does not hybridize to the coding sequence (codeB).

A second cleavable chimeric adaptor is used to couple a second identifier oligonucleotide to the distal end of the partner nucleic acid strand with respect to the third chemical moiety (i.e. the second identifier oligonucleotide is coupled to the 5' end of the nucleic acid spacer strand). The second identifier oligonucleotide contains a third coding sequence (codeC) encoding the identity of the third chemical moiety. The first and second cleavable chimeric adaptors are then removed by purification, RNAse or pH to leave a partner nucleic acid strand comprising a third coding sequence and first and second spacer regions at positions corresponding to the first and second coding sequences of the nucleic acid strand.

The nucleic acid strand and the partner nucleic acid strand are then hybridized together through complementary regions in the strands to form a complex (FIG. 2E). The proximal end of the second identifier oligonucleotide of the partner strand with respect to the third chemical moiety hybridises to complementary regions at the distal end of the nucleic acid strand to produce a 5' overhang in the complex that contains the third coding sequence (codeC). The nucleic acid strand is then extended along the partner strand using a polymerase. Coding information for all three chemical moieties in the pharmacophore is now encoded on the nucleic acid strand.

FIGS. 3A and 3B show strategies for the production of a three building block pharmacophore library in which the building blocks are coupled to a single strand of the library members. A nucleic acid strand is coupled to a first chemical moiety. The nucleic acid strand is then contacted with a cleavable adaptor and a first identifier oligonucleotide which hybridize through complementary regions to form a trimeric complex. The first identifier oligonucleotide contains a code sequence encoding the identity of the first chemical moiety. The first identifier oligonucleotide is ligated to the nucleic acid strand and the adaptor is cleaved. A second chemical moiety is then coupled to the first chemical moiety. The nucleic acid strand is then contacted with a further cleavable adaptor and a second identifier oligonucleotide which hybridizes through complementary regions to form a complex. The second identifier oligonucleotide contains a code sequence encoding the identity of the second chemical moiety. The second identifier oligonucleotide is ligated to the nucleic acid strand and the adaptor is cleaved. A third chemical moiety is then coupled to the first chemical moiety. In FIG. 3A, the nucleic acid strand is then contacted with a further cleavable adaptor and a third identifier oligonucleotide which hybridize through complementary regions to form a trimeric complex. The third identifier oligonucleotide contains a code sequence encoding the identity of the third chemical moiety. The third identifier oligonucleotide is ligated to the nucleic acid strand and the adaptor is cleaved. The nucleic acid strand may than be combined with a complementary sub-library to form a nucleic acid-encoded library. In FIG. 3B, the nucleic acid strand is then contacted with a third identifier oligonucleotide which contains a code sequence encoding the identity of the third chemical moiety. The third identifier oligonucleotide hybridizes through complementary regions to the 3' end of the nucleic acid strand to form a complex with a single stranded 5' overhang comprising the code sequence. The nucleic acid strand is then filled in along the single stranded identifier oligonucleotide template using a polymerase such as a Klenow fragment to incorporate the complement of the code sequence. The nucleic acid strand may than be combined with a complementary sub-library to form a nucleic acid-encoded library.

EXPERIMENTS

Figure 1A:
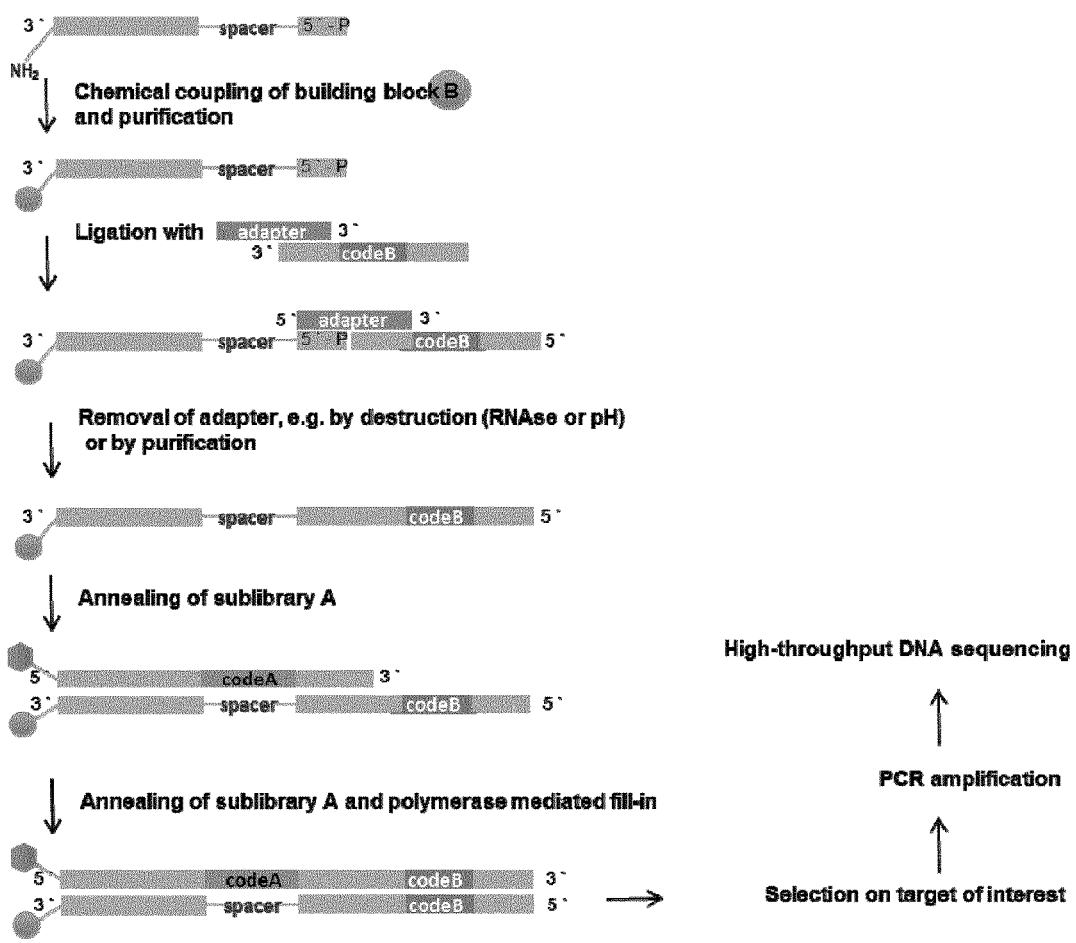
Figure 1B:
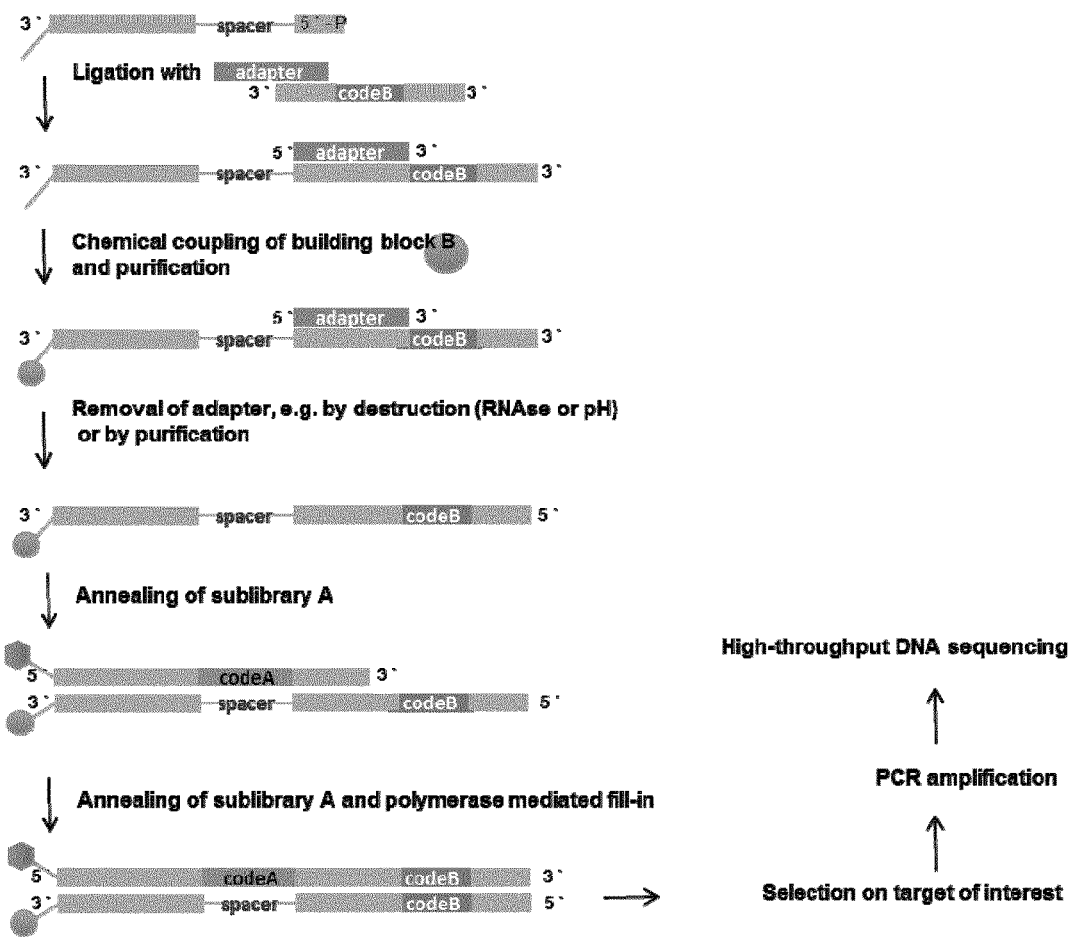

Example 1: Construction of a Sub-Library of Oligonucleotide-Compound Conjugates Using 3'-Aminomodified, 5'-Phosphorylated Oligonucleotides Synthetic oligonucleotides were purchased from various commercial suppliers. They were stored as 1 mM and 100

µM stock solutions in at −20° C. Chemical compounds were purchased from various commercial suppliers. Enzymes were purchased from various commercial suppliers.

1.1 Agarose and Polyacrylamide Gel Electrophoresis

DNA consisting of 10 to 300 nucleotides was analyzed on native polyacrylamide 20% TBE gels (1.0 mm, 12 well, Invitrogen) or on denaturing polyacrylamide 15% TBE-Urea gels (1.0 mm, 12 well, Invitrogen). A current of 60 mA with a voltage of 180 V was applied for 75 minutes on the electrophoresis box (Novex). The gels were stained with SYBR Green I. Preparative gel electrophoresis was performed on 2.0% agarose/TBE gels (stained with ethidium bromide) using 60 mA and 100 V for 25 minutes. SYBR Green I and ethidium bromide were detected by UV excitation.

1.2 Synthesis of Fmoc-Protected Amino Acid and Carboxylic Acid Oligonucleotide Conjugates 12.5 µl 100 mM Fmoc-protected amino acids or carboxylic acids (1.25 µmol in dry dimethyl sulfoxide [DMSO]) were activated for 30 min at 30° C. with 12 µl 100 mM 1-ethyl-3-(3-dimethylaminopropyl)carbodiimide (EDC, 1.2 µmol) and 10 µl 333 mM N-hydroxysulfosuccinimide (S-NHS, 3.3 µmol, in DMSO/H2O, 2:1) in 215 µl dry DMSO and subsequently reacted overnight at 30° C. with 5 µl of amino-modified oligonucleotide (5 nmol) dissolved in 50 µl 500 mM triethylamine/hydrogen chloride (TEA/HCl, 25 µmol, pH=10.0). Carboxylic acids were quenched with 20 µl 500 mM Tris/HCl (pH=8.1) at 30° C. for 1 h. Fmoc-protected amino acids were quenched and concurrently deprotected with 5 µl 1 M tris(hydroxymethyl)aminomethane (Tris) and 5 µl pure TEA at 30° C. for 1 h. After quenching and deprotection, the DNA-compound conjugate was precipitated with ethanol (see protocol for ethanol precipitation for compound-conjugates) before purifying by HPLC. The separated and collected compound conjugates were vacuum-dried overnight, redissolved in 100 µl $H_2O$, and analyzed by ESI-MS.

1.3 Synthesis of Sulfonamide Oligonucleotide Conjugates

25 µl 100 mM sulfonyl chloride (2.5 µmol in dry acetonitrile [MeCN]) were mixed with 25 µl 1 M sodium hydrogen carbonate in H2O (pH=9.0), 100 µl MeCN, 95 µl H2O and subsequently reacted with 5 µl of the amino-modified oligonucleotide (5 nmol) overnight at 30° C. The reaction was quenched with 20 µl 500 mM Tris/HCl (pH=8.1) at 30° C. for 1 h. After quenching the DNA-compound conjugate was precipitated with ethanol (see protocol for ethanol precipitation for compound-conjugates) before purification by HPLC. The separated and collected compound conjugates were vacuum-dried overnight, redissolved in 100 µl H2O, and analyzed by ESI-MS.

1.4 Synthesis of Oligonucleotide Conjugates from Carboxylic Acid Anhydrides 5.2 µl 100 mM carboxylic acid anhydrides (25 µl, 2.5 µmol in dry DMSO) were mixed together with 25 µl 500 mM sodium hydrogen phosphate in H2O (pH=7.1), 195 µl DMSO, 35 µl H2O and subsequently reacted with 5 µl of the amino-modified oligonucleotide (5 nmol) overnight at 30° C. The reaction was quenched with 20 µl 500 mM Tris/HCl (pH=8.1) at 30° C. for 1 h. After quenching, the DNA-compound conjugate was precipitated with ethanol (see protocol for ethanol precipitation for compound-conjugates) before purifying by HPLC. The separated and collected compound conjugates were vacuum-dried overnight, redissolved in 100 µl of H2O, and analyzed by ESI-MS.

1.5 Ethanol Precipitation of Compound-Oligonucleotide Conjugates

Before HPLC purification, the compound-olignucleotide conjugates were precipitated with ethanol. In this procedure, 100 µl 3 M sodium acetate (pH=4.7) and 30 µl 5 M acetic acid were added to the reactions. After vortexing, 1100 µl pure (100%) ethanol was added and the reactions were allowed to stand for 30 min at 22° C. and 30 min at −20° C. before centrifugation (30 min, 13'200 rpm, 4° C.). Immediately after centrifugation, the supernatant was carefully discarded and the pellet was dissolved in 500 µl 100 mM triethylammonium acetate (TEAA) buffer (pH=7.0) and subjected to HPLC purification.

1.6 High-Performance Liquid Chromatography (HPLC) of Oligonucleotide-Compound Conjugates Oligonucleotide-conjugated compounds for the library were separated from the unreacted amino-modified Elib4.aT oligo by HPLC. A reverse-phased C18-XTerra column (5 µm, 10×150 mm, Waters) with organic/inorganic particle (silica and polymeric supports) was used as stationary phase. As a mobile phase, an aqueous, 100 mM triethylammonium acetate (TEAA) buffer C (pH=7.0) was used together with an acetonitrile gradient (buffer D: 100 mM TEAA in 80% MeCN/20% H2O. Depending on the retention time for a class of compounds, either a short (16 min, for more hydrophilic compounds) or a long (30 min, for more hydrophobic compounds a gradient program was run (T=30° C., p=0-300 bar).

In order to distinguish oligonucleotides and oligonucleotide-conjugates from starting compounds and side-products, absorption was monitored at 260 nm and 280 nm. The oligonucleotide absorption ratio 260 nm/280 nm is typically 1.8/1. The collection of fractions was started after 4 min with a minimum intensity threshold of 30'000 (106:=Abs=1 for the observed channel [260 nm]). The minimum fraction collecting frame was 5 s, the maximum 300 s.

1.7 Liquid Chromatography-Mass Spectrometry (LC-MS)

Mass-analysis of the oligo-coupled compounds was performed by the combination of liquid chromatography with electrospray ionization mass spectrometry (LC-ESI-MS). A reverse-phased C18-XBridge column (2.5 µm, 2.1×50 mm, Waters) with organic/inorganic particle (silica and polymeric supports) was used as stationary phase. As a mobile phase, 400 mM 1,1,1,3,3,3-hexafluoroisopropanol (HFIP), 2 mM triethylamin (TEA) buffer C was applied with a methanol gradient (buffer D: 400 mM HFIP, 2 mM TEA in 50% H2O/50% methanol (T=30° C., p=0-200 bar). A tandem-quadrupole mass spectrometer (Quattro micro API, Waters, Milford, Conn.) with electrospray ionization (ESI) source was used for mass detection and analysis. Mass spectrometric analyses were performed in negative ion-mode. ESI interface parameters were set as follows: disolvation temperature: 200° C., source temperature: 110° C.; capillary voltage: 3.0 kV; cone voltage: 40 V; scan time: 0.5 s; inter-scan delay time: 0.1 s.

1.8 Encoding by Ligation

50 µl 2 µM compound-oligonucleotide conjugate (100 µmol), 10 µl 15 µM coding oligonucleotide (150 pmol), 10 µl 30 µM chimeric RNA/DNA adapter oligonucleotide, 10 µl NEB 10x ligase buffer and 19.5 µl H2O were mixed and heated up to 90° C. for 2 min. Then the mixture was passively cooled down to 22° C. (hybridization). Afterwards, 0.5 µl NEB ligase was added. Ligation was performed at 16° C. for 10 hours. The ligase was inactivated for 15 min at 70° C.

1.9 Degradation of the Chimeric DNA/RNA Adapter

Hydrolysis of the RNA was achieved when an equivalent volume (13 µl) of 200 mM sodium hydroxide and the ligation solution was mixed and incubated for 5 h at 22° C. The solution was then neutralized to pH=7.9. Alternatively, enzymatic cleavage was effectively carried out by adding 5.3 µl of 10× RNase H reaction buffer, 33.7 H2O and 1.5 µl RNase H. RNase H was inactivated by heat denaturation (15 min, 70° C.). Optionally, the ligated oligonucleotide-compound conjugates could be purified again by ethanol precipitation as described above. Equimolar amounts of encoded compounds were then mixed together to generate the desired sub-library

Example 2: Construction of a Sub-Library of Oligonucleotide-Compound Conjugates Using 3'-Aminomodified, 5'-Phosphorylated Oligonucleotides

2.1 Preparation of Amino-Modified Encoding Oligonucleotides

Amino-modified encoding oligonucleotides necessary were either purchased from a commercial supplier or obtained by encoding by ligation: 50 µl 2 µM amino-modified oligonucleotide (100 pmol), 10 µl 15 µM coding oligonucleotide (150 pmol), 10 µl 30 µM chimeric RNA/DNA adapter oligonucleotide, 10 µl NEB 10× ligase buffer and 19.5 µl H2O were mixed and heated up to 90° C. for 2 min. Then the mixture was passively cooled down to 22° C. (hybridization). Afterwards, 0.5 µl NEB ligase was added. Ligation was performed at 16° C. for 10 hours. The ligase was inactivated for 15 min at 70° C.

2.2 Degradation of the Chimeric DNA/RNA Adapter

Hydrolysis of the RNA was achieved when an equivalent volume (13 µl) of 200 mM sodium hydroxide and the ligation solution was mixed and incubated for 5 h at 22° C. The solution was then neutralized to pH=7.9 Alternatively, enzymatic cleavage was effectively carried out by adding 5.3 µl of 10× RNase H reaction buffer, 33.7 H2O and 1.5 µl RNase H. RNase H was inactivated by heat denaturation (15 min, 70° C.). Optionally, the ligated oligonucleotide-compound conjugates could be purified again by Ethanol precipitation as described above.

The sub-library of compound-oligonucleotide conjugates was then obtained by chemically modifying the individual amino-modified encoded oligonuclotides, followed by Ethanol precipitation, HPLC purification, and MS-based analytics, as described in Example 1. Equimolar amounts of encoded compounds were then mixed together to the desired sub-library.

Example 3: Construction of a Sub-Library of Oligonucleotide-Compound Conjugates Using 5'-Aminomodified Oligonucleotides Commercially purchased oligonucleotides carrying a 5' primary amino group and an individual encoding sequence were coupled to carboxylic acids, acyl chlorides, cyclic anhydrides, or isothiocyanates. Some of the carboxylic acids contained an Fmoc-protected amino group. Typically, for acyl chlorides, 200 µL of a 25 µM solution of oligonucleotide in 100 mM NaHCO3, pH 9, was added to 200 µL of a 4 mM solution of acyl chloride in MeCN.

In the case of isothiocyanates, 100 µL of a 50 µM solution of oligonucleotide in 100 mM KHPO4, pH 7.1, was added to 200 µL of a 2.6 mM solution of isothiocyanate in DMSO. For cyclic anhydrides, 100 µL of a 50 µM solution of oligonucleotide in 100 mM KHPO4, pH 7.1, was added to 200 µL of a 2.6 mM solution of anhydride in DMSO. To activate the carboxylic acids, 22 µL of a solution containing 45 mM EDC and 180 mM sulfo-NHS in 15% H2O/85% DMSO was added to 230 µL of a 5.5 mM solution of the carboxylic acid in DMSO. After 30 min at 30° C., 60 µL of a solution of 83 µM oligonucleotide in 420 mM TEA/HCl, pH 10, was added. All reactions were stirred for 12 h at 30° C. The reactions were quenched by adding 20 µL of 500 mM Tris/HCl, pH 8, and stirred for an additional 1 h at 30° C. In the case of Fmoc-protected compounds, the quenching and removal of the Fmoc group was performed by addition of 5 µL of 1 M Tris and 5 µL of triethylamine and stirring for 1 h at 30° C.

For HPLC purification, 400 µL of 100 mM TEAA, pH 7, was added to the reaction mixture. In the case of the Fmoc samples, 20 µL of 1 M HCl was additionally added. Purifications were performed by HPLC on an XTerra Prep RP18 column (5 µM, 10×150 mm) using a linear gradient from 10 to 40% MeCN in 100 mM TEAA. The desired samples were redissolved in 100 µL of H2O. An amount of 5 µL was analyzed by LC-ESI-MS on an XTerra RP18 column (5 µM, 4.6×20 mm) using a linear gradient from 0 to 50% MeOH over 1 min in 400 mM HFIP/5 mM TEA. The mass spectrum was measured from 900 to 2000 m/z by a Waters Quattro Micro instrument. The mass spectra of oligonucleotides before and after conjugation were analyzed. The samples containing the oligonucleotide-compound conjugates of the expected size were pooled and precipitated by adding 10% v/v of 3 M NaAc, pH4.7, and 250% v/v of EtOH. The pellets were collected by centrifugation and washed by addition of ice cold 85% EtOH, followed by drying under vacuum. The oligonucleotide-compound conjugates were then redissolved in 100 µL of H2O, and the OD260 was determined by a ND-1000 (Nanodrop). Equimolar amounts of encoded compounds were then mixed together to generate the desired sub-library.

Example 4: Construction of a Sub-Library Displaying Two Chemical Building Blocks (2BB) Using 5'-Aminomodified Oligonucleotides

4.1 DNA-Conjugation of Carboxylic Acids as First Building Block (BB1)

Protected DNA 45-mers with a terminal 5'-amino modifier C12 attached to the solid support (controlled pore glass) were distributed into synthesis cartridges (approx. 50 nmol). The supports were washed with MeCN and DCM (2×). A solution of 3% trichloroacetic in DCM (1-2 mL) was dropwise eluted from the cartridge followed by washing with DCM (2 mL) and these two steps were repeated 5 times. The solid support was washed with DCM (1×1 mL) and MeCN (2×1 mL). The solid support was treated with a solution of Fmoc-L-DAP(Mtt)-OH (50 mM), HATU (50 mM) and DIEA (150 mM) in DMF (0.5 mL) and let react for 2 h at room temperature. The solution was removed and the solid support rinsed with DMF (2×1 mL), MeCN (1×1 mL) and DCM (2×1 mL). The Mtt-group was removed as described above for the Mmt-group. The solid support was then treated with a solution of the corresponding carboxylic acid (50 mM), HATU (50 mM) and DIEA (150 mM) in DMF (0.5 mL) and let react overnight. The solution was removed and the support rinsed with DMF (2×1 mL), MeCN (2×1 mL) and dried under a stream of air. The DNA was cleaved from the solid support and deprotected by 2 h incubation in conc. aq. NH3/MeNH2 (AMA) (1 mL) at room temperature. The AMA solution was evaporated, the residue dissolved in water (0.2 mL) and the DNA conjugates purified by reverse-phase HPLC. Product-containing fractions were combined, evaporated and analyzed by LC-MS measurement.

4.2 DNA-Conjugation of Carboxylic Acids as Second Building Block (BB2)

Equimolar amounts of the DNA-conjugates obtained as described above were combined and further derivatized: The combined conjugates (0.75 nmol) were immobilized on DEAE sepharose (0.1 mL of slurry). The resin was washed with 10 mM aq. AcOH (2×0.5 mL), water (2×0.5 mL) and DMSO (2×0.5 mL). To the resin-immobilized DNA was added a solution of the corresponding carboxylic acid (50 mM), EDC (50 mM) and HOAt (5 mM) in DMSO (0.5 mL). The slurry was agitated for 2 h at room temperature. The solution was removed and the resin washed with DMSO (1×0.5 mL) and treated with freshly activated reaction solution. These steps were repeated to reach three coupling steps of 2 h each. The reaction solution was removed and the resin washed with DMSO (2×0.5 mL) and 10 mM aq. AcOH (3×0.5 mL). The DNA was eluted from the resin by incubation with 3 M AcOH buffer (pH 4.75) for 5 min. The DNA-conjugates were isolated by ethanol-precipitation and the pellets redissolved in deionized water (50 µL). To ensure a high degree of conversion for chemical BB2, all used carboxylic acids were tested for coupling efficiency and only carboxylic acids with high conversion yields in test reactions (typically >80%) were used for library synthesis. The individual DNA-chemical conjugates constitute a (not pooled) sub-library which is encoded for BB1 but not yet for BB2 and can be used as starting material for the library construction described in Examples 6-8.

Example 5: Preparation of a DNA-Encoded Library [1+1 Library (FIG. 1A+1B)]

20 µl 0.5 µM of pooled 3'-compound oligonucleotide conjugates (e.g. sub-library of Example 1 or 2), 1 µl 10 µM of pooled 5'-compound oligonucleotide conjugates (e.g. sub-library of Example 3), 10 µl 10×NEB2 reaction buffer, 57 µl H$_2$O and 8 µl 500 µM dNTPs were mixed and heated up to 90° C. for 2 min, then cooled to 22° C. for hybridization. 2 µl NEB Klenow polymerase was added and the sample was incubated at 25° C. for 90 min, optionally followed by a purification step. The obtained encoded self-assembling chemical library could optionally be stored or directly used for target-based selections.

Figure 2A:
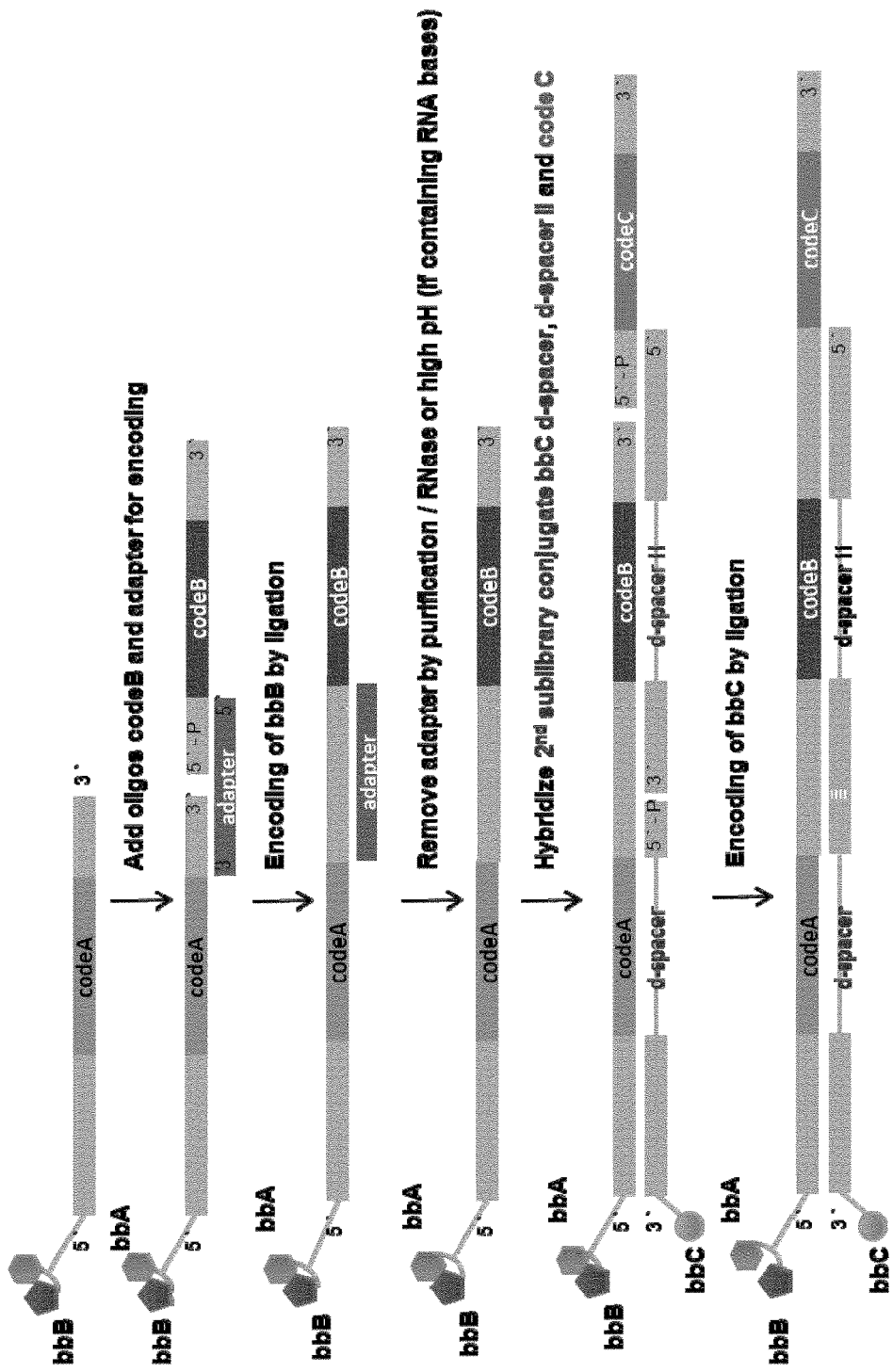

Example 6: Preparation of a DNA-Encoded Library [2+1 Library (FIG. 2A)]

The individual sub-library members of Example 3, which carry the chemical building blocks BB1 and BB2 and which are encoded for BB1 (but not yet for BB2) were encoded for BB2 according to the following procedure:

6.1 Encoding by Ligation

50 µl of 2 µM compound-oligonucleotide conjugate (100 pmol), 10 µl 15 µM coding oligonucleotide (150 pmol), 10 µl 30 µM chimeric RNA/DNA adapter oligonucleotide, 10 µl NEB 10× ligase buffer and 19.5 µl H$_2$O were mixed and heated up to 90° C. for 2 min. Then the mixture was passively cooled down to 22° C. (hybridization). Afterwards, 0.5 µl NEB ligase was added. Ligation was performed at 16° C. for 10 hours. The ligase was inactivated for 15 min at 70° C.

6.2 Degradation of the Chimeric DNA/RNA Adapter

Hydrolysis of the RNA was achieved when an equivalent volume (13 µl) of 200 mM sodium hydroxide and the ligation solution was mixed and incubated for 5 h at 22° C. The solution was then neutralized to pH-7.9. Alternatively, enzymatic cleavage was effectively carried out by adding 5.3 µl of 10× RNase H reaction buffer, 33.7 H2O and 1.5 µl RNase H. RNase H was inactivated by heat denaturation (15 min, 70° C.). Optionally, the ligated oligonucleotide-compound conjugates could be purified again by Ethanol precipitation as described above.

Equimolar amounts of encoded compounds were then mixed together to the desired sub-library A. A portion of sub-library A was then split into 200 vials (10 µl of 20 nM compound-oligonucleotide conjugates) and each vial contained: 10 µl of 20 nM individual sub-library B member, 10 µl of 20 nM DNA/RNA adaptor oligonucleotide (d-spacerII) and 10 µl of 20 nM individual coding oligonucleotide (code C), 10 µl NEB 10× ligase buffer and 10 µl H2O. The solutions were mixed and heated up to 90° C. for 2 min. Then the mixture was cooled down to 22° C. (hybridization). Afterwards, 0.5 µl NEB ligase was added. Ligation was performed at 16° C. for 10 hours. Equimolar amounts of the 200 vials were mixed together, optionally followed by a purification step. The obtained DNA-encoded chemical library could optionally be stored or directly used for target-based selections.

Figure 2B:
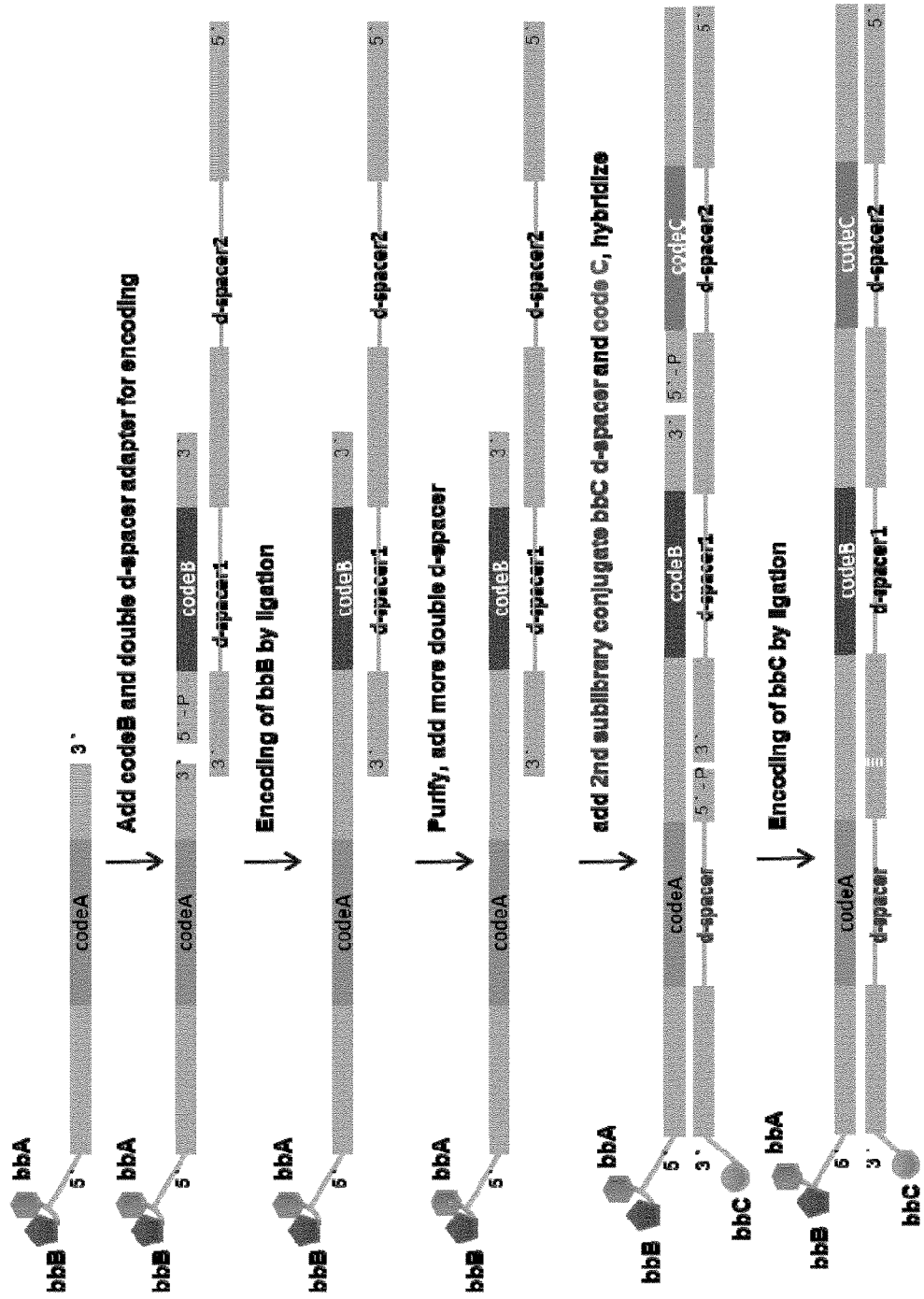

Example 7: Preparation of a DNA-Encoded Library [2+1 Library (FIG. 2B)]

The individual sub-library members of Example 3, which carry the chemical building blocks BB1 and BB2 and which are encoded for BB1 (but not yet for BB2) were encoded for BB2 according to the following procedure:

7.1 Encoding by Ligation

50 µl of 2 µM compound-oligonucleotide conjugate (100 pmol), 10 µl 15 µM coding oligonucleotide (150 pmol), 10 µl 30 µM adapter oligonucleotide containing 2 abasic sites, 10 µl NEB 10× ligase buffer and 19.5 µl H2O were mixed and heated up to 90° C. for 2 min. Then the mixture was passively cooled down to 22° C. (hybridization). Afterwards, 0.5 µl NEB ligase was added. Ligation was performed at 16° C. for 10 hours. The ligase was inactivated for 15 min at 70° C. Optionally, the ligated oligonucleotide-compound conjugates could be purified as described above.

Equimolar amounts of encoded compounds were then mixed together to the desired sub-library A. A portion of sub-library A was then split into 200 vials (10 µl of 20 nM compound-oligonucleotide conjugates) and each vial contained: 10 µl of 20 nM individual sub-library B member, 10 µl of 20 nM adapter oligonucleotide containing 2 abasic sites and 10 µl of 20 nM individual coding oligonucleotide (code C), 10 µl NEB 10× ligase buffer and 10 µl H$_2$O. The solutions were mixed and heated up to 90° C. for 2 min. Then the mixture was cooled down to 22° C. (hybridization). Afterwards, 0.5 µl NEB ligase was added. Ligation was performed at 16° C. for 10 hours. Equimolar amounts of the 200 vials were mixed together, optionally followed by a purification step. The obtained DNA-encoded chemical library could optionally be stored or directly used for target-based selections.

Figure 2C:
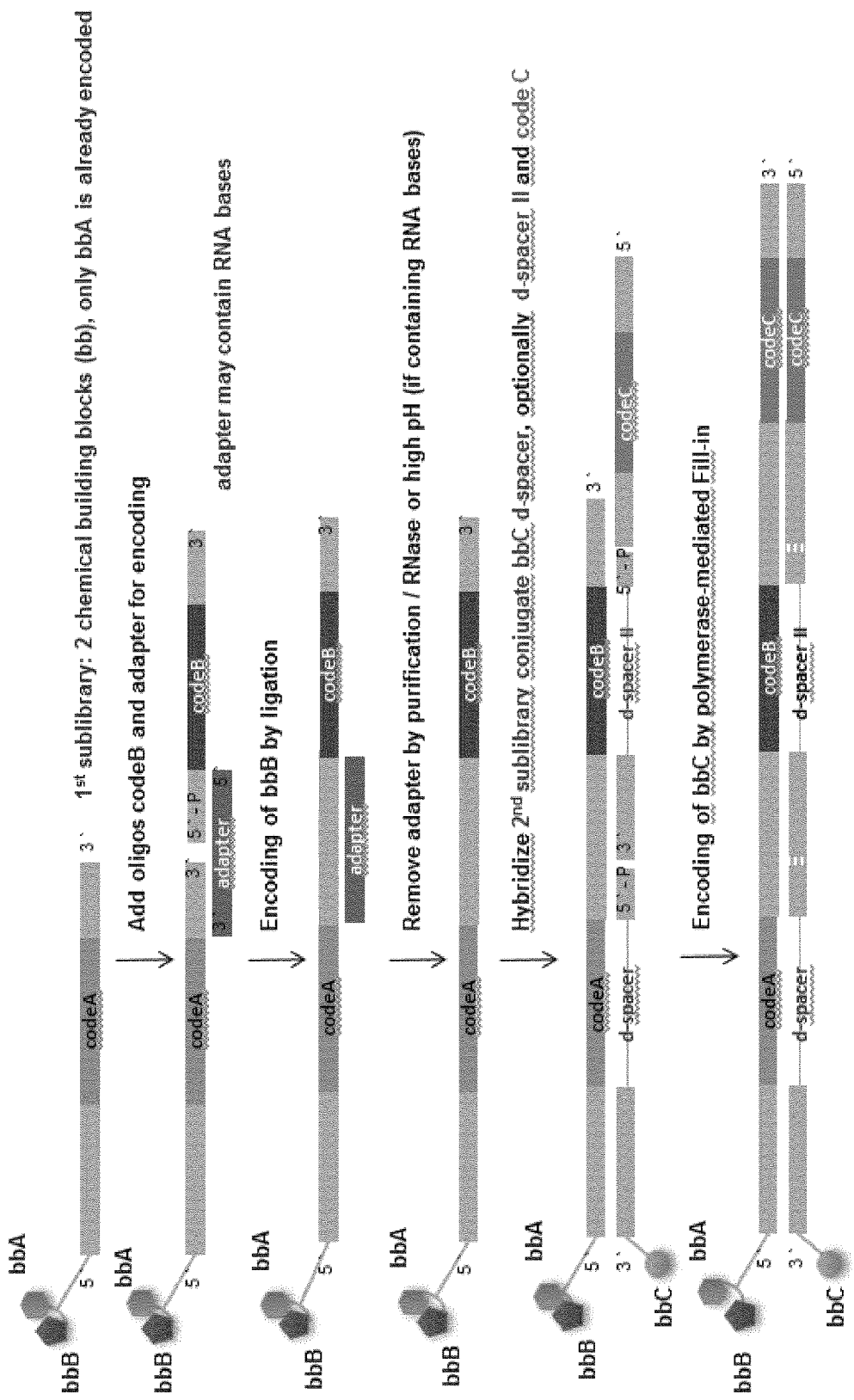

Example 8: Preparation of a DNA-Encoded Library [2+1 Library (FIG. 2C)]

The individual sub-library members of Example 3, which carry the chemical building blocks BB1 and BB2 and which are encoded for BB1 (but not yet for BB2) were encoded for BB2 according to the following procedure.

8.1 Encoding by Ligation

50 µl of 2 µM compound-oligonucleotide conjugate (100 pmol), 10 µl 15 µM coding oligonucleotide (150 pmol), 10 µl 30 µM chimeric RNA/DNA adapter oligonucleotide, 10 µl NEB 10× ligase buffer and 19.5 µl H$_2$O were mixed and heated up to 90° C. for 2 min. Then the mixture was passively cooled down to 22° C. (hybridization). Afterwards, 0.5 µl NEB ligase was added. Ligation was performed at 16° C. for 10 hours. The ligase was inactivated for 15 min at 70° C.

8.2 Degradation of the Chimeric DNA/RNA Adapter

Hydrolysis of the RNA was achieved when an equivalent volume (13 µl) of 200 mM sodium hydroxide and the ligation solution was mixed and incubated for 5 h at 22° C. The solution was then neutralized to pH=7.9. Alternatively, enzymatic cleavage was effectively carried out by adding 5.3 µl of 10× RNase H reaction buffer, 33.7 H$_2$O and 1.5 µl RNase H. RNase H was inactivated by heat denaturation (15 min, 70° C.). Optionally, the ligated oligonucleotide-compound conjugates could be purified again by Ethanol precipitation as described above.

Equimolar amounts of encoded compounds were then mixed together to the desired sub-library A. A portion of sub-library A was then split into 200 vials (10 µl of 20 nM compound-oligonucleotide conjugates) and each vial contained: 10 µl of 20 nM individual sub-library B member, 10 µl of 20 nM DNA/RNA adaptor oligonucleotide (d-spacerII) and 10 µl of 20 nM individual coding oligonucleotide (code C), 10 µl 10×NEB2 reaction buffer, 52 µl H2O and 8 µl 500 µM dNTPs were mixed and heated up to 90° C. for 2 min, then cooled to 22° C. for hybridization. 2 µl Klenow polymerase was added and the sample was incubated at 25° C. for 90 min, optionally followed by a purification step. Equimolar amounts of the 200 vials were mixed together, optionally followed by a purification step. The obtained DNA-encoded chemical library could optionally be stored or directly used for target-based selections.

Example 9: Chimeric Adaptors

Chimeric adapters were used to facilitate the ligation mediated by T4 DNA ligase, as this enzyme only seals nicks in double stranded DNA. Chimeric adapters were required for the enzymatic reaction but needed to be disposed of afterwards. The Chimeric adapters were DNA oligonucleotides with intermittent RNA nucleotides. The adapter-specific disintegration was achieved by NaOH-treatment of the ligation products, which cleaves the chimeric adapters at the RNA sites. An alternative disintegration strategy is the cleavage using RNase H. For the 2+1 library of Example 10, the three Chimeric Adapters shown in Table 1 were employed.

9.1 Degradation Tests

Figure 4:
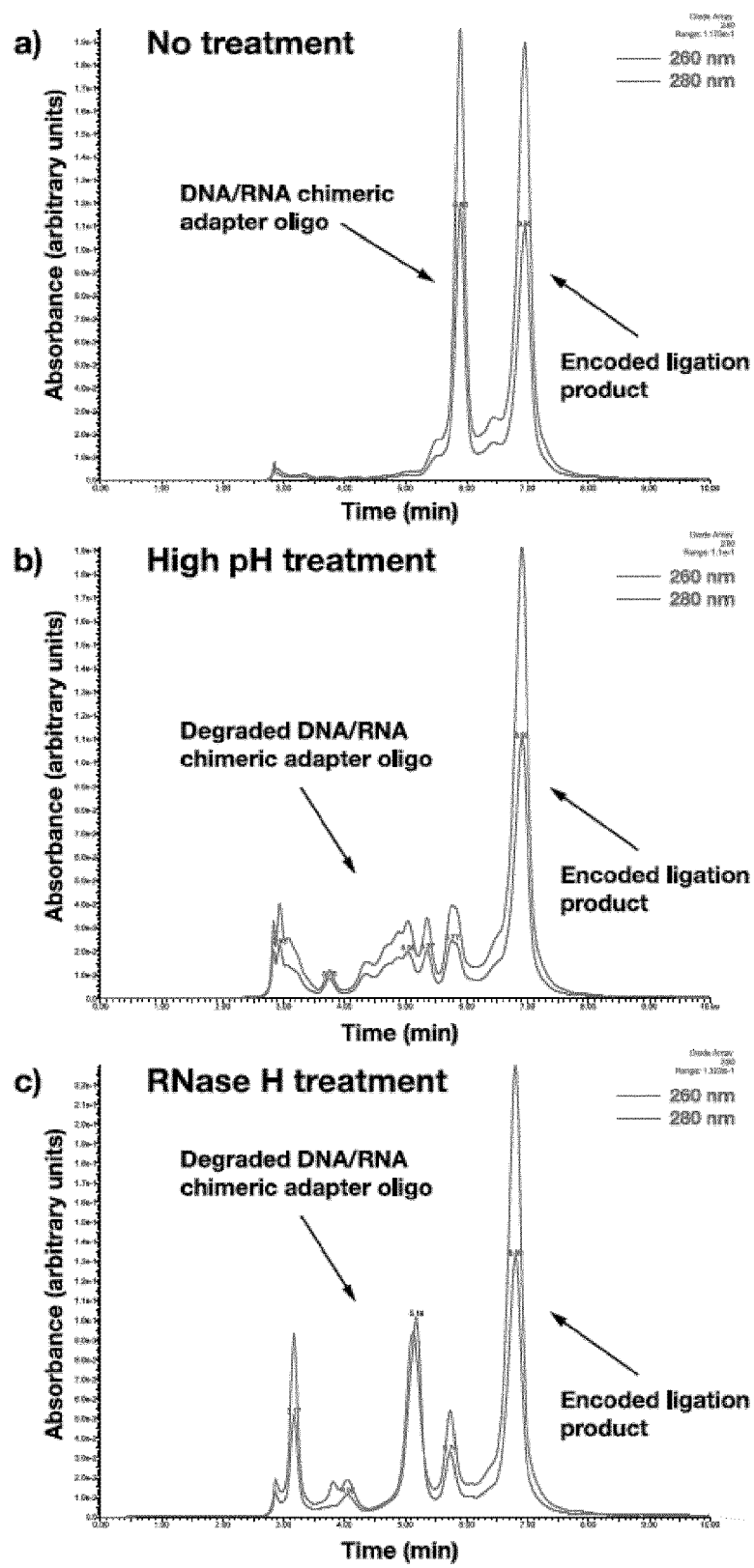
FIG. 4 shows analytical HPLC traces (recording absorbance at 260 nm and 280 nm respectively) of A) untreated chimeric adapter and encoded ligation oligonucleotide product of Table 2, B) high pH treatment with NaOH of the same oligonucleotides and C) RNase H treatment of the same oligonucleotides.

The Chimeric Adapters shown in Table 2 were tested for degradation by means of NaOH treatment (high pH) or RNase H treatment. FIG. 4 shows analytical HPLC traces (recording absorbance at 260 nm and 280 nm respectively) of a) untreated chimeric adapter and encoded ligation oligonucleotide product, b) high pH treatment with NaOH of the same oligonucleotides and c) RNase H treatment of the same oligonucleotides. Both methods show disintegration of the DNA/RNA chimeric adapter oligonucleotide.

9.3 Ligation

Figure 5:
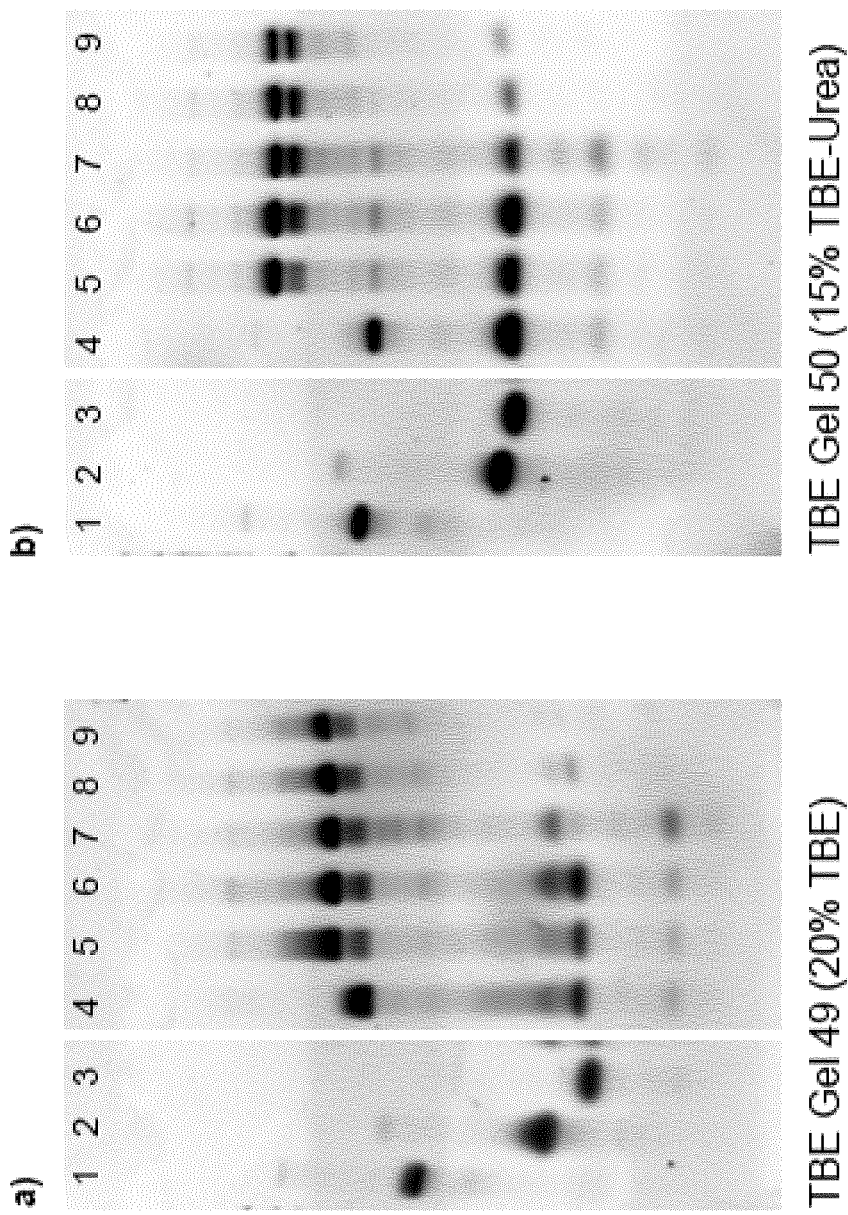
FIG. 5 shows the results of polyacrylamide gel electrophoresis of the 5' coupled oligonucleotides and ligation products shown in Table 3 using TBE Gel 49 (20% TBE) (FIG. 5A) and TBE Gel 50 (15% TBE Urea) (FIG. 5B).

The ligation of nucleic acid strands carrying compounds at their 5' end using chimeric adapters was assessed. TBE and TBE-Urea gels (life technologies, Novex TBE Gels, 20%, 15 well, Cat. No. EC63155BOX; life technologies, Novex® TBE-Urea Gels, 15%, 15 well, Cat. No. EC68855BOX), were loaded as shown in Table 3 and subjected to electrophoresis. The results are shown in FIG. 5 and indicate that strands were successfully ligated and the chimeric adapters removed by standard purification techniques.

Figure 6:
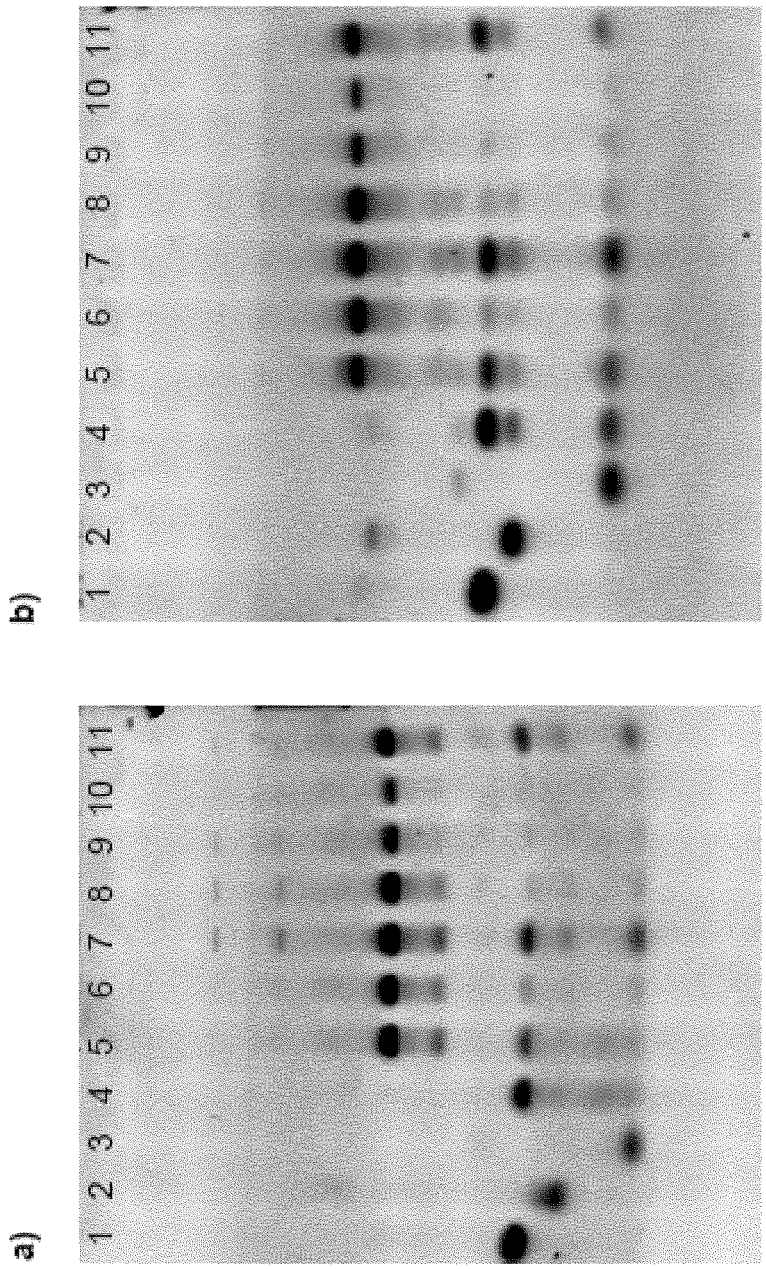
FIG. 6 shows the results of polyacrylamide gel electrophoresis of the 3' coupled oligonucleotides and ligation products shown in Table 4 using TBE Gel 57 (20% TBE) (FIG. 6A) and TBE Gel 58 (15% TBE Urea) (FIG. 6B).

The ligation of nucleic acid strands carrying compounds at their 3' end using chimeric adapters was assessed. TBE and TBE-Urea gels (life technologies, Novex TBE Gels, 20%, 15 well, Cat. No. EC63155BOX; life technologies, Novex® TBE-Urea Gels, 15%, 15 well, Cat. No. EC68855BOX), were loaded as shown in Table 4 and subjected to electrophoresis. The results are shown in FIG. 6 and indicate that strands were successfully ligated and the chimeric adapters removed by standard purification techniques.

Figure 2D:
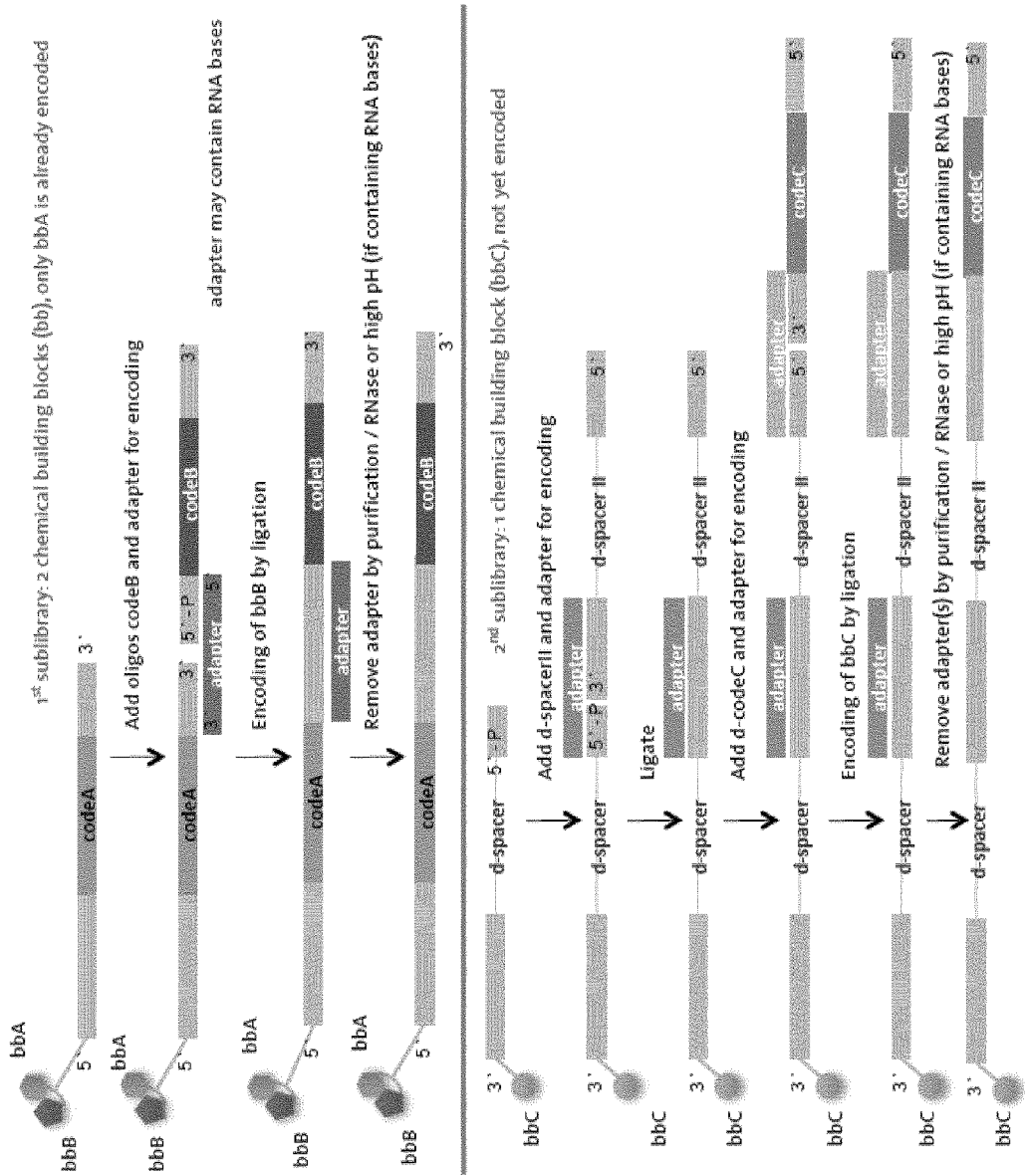
Figure 2E:
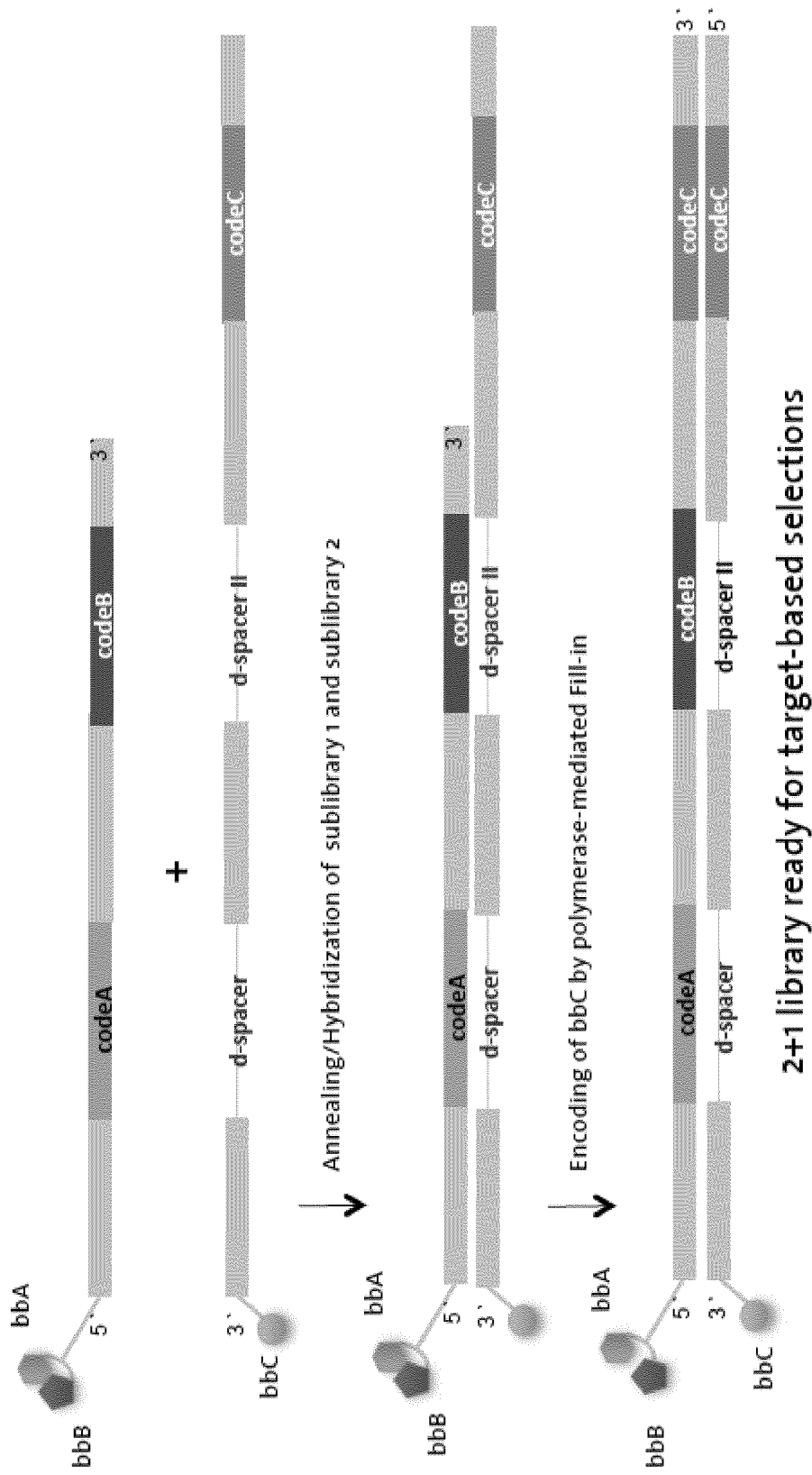

Example 10: Preparation of a DNA-Encoded Library [2+1 Library (FIGS. 2D and 2E)]

The ESAC 2+1 library consists of two sub-libraries. The 5'-sub-library carries two compounds at the 5'-end of a single-stranded oligonucleotide while the 3'-sub-library consists of one compound, coupled to the 3'-end of a complementary single-stranded oligonucleotide. Both sub-library are mixed in equimolar amounts and hybridized by heating. Klenow fill-in is used to transfer coding information from the 3'-strand to the 5'-strand.

10.1 5'-Sublibrary (2 Building Blocks)

The 5'-Sublibrary was generated in split-and-pool fashion. Building block 1 was coupled to an oligonucleotide that contains Code 1. Compound-oligonucleotide conjugates were pooled, split to equimolar amounts and coupled to building block 2. These intermediate library members were encoded via ligation: conjugates were incubated with an equimolar amount of an oligonucleotide that contained code two and an excess of a chimeric adapter oligonucleotide (DNA/RNA hybrid) (see Table 5). The Code 1 and Code 2 oligonucleotides were ligated using T4 DNA Ligase. The chimeric adapter was disintegrated using 250 mM NaOH. Finally, the ligation product was purified using the Qiagen QIAquick gel extraction kit and library members were pooled again in equimolar amounts in order to yield the final 5'-sublibrary.

10.2 3'-Sub-Library

The 3'-sub-library carries building block 3 at the 3'-end of a single-stranded oligonucleotide. The 3'-oligonucleotide, named Elib4.aT, contains a d-spacer (abasic nucleotide backbone) in order to allow hybridization to Code 1. Elib4.aT was ligated (as described above) to a second d spacer that allowed hybridization to Code 2, and purified as described above (see Table 6). The oligonucleotide containing Code 2 was added in a second ligation step. The final product was purified and pooled in equimolar amounts in order to yield the final 3'-sublibrary.

10.2. Hybridization and Klenow Fill-In

The 3'- and 5'-sublibraries were mixed in equimolar amounts. Heating and subsequent cooling down to room temperature leads to the hybridization (=combinatorial assembly) of the two sub-libraries. Klenow polymerase was used to fill in the Code 3 information of the 3'-strand to the 5'-strand as shown in Table 7, which was amplified by PCR.

Figure 3A:
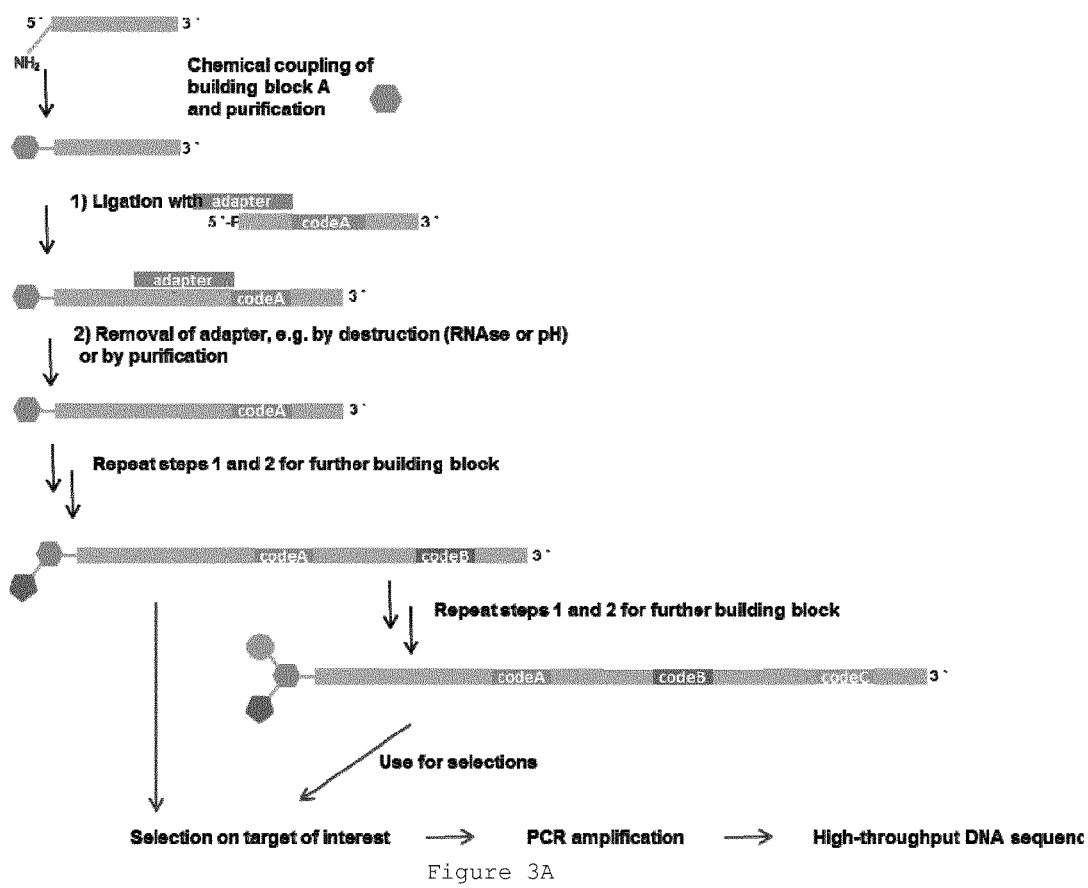

Example 11: Preparation of a DNA-Encoded Library of Three or More Building Blocks [(FIG. 3A)]

5'-Amino-modified oligonucleotides were modified with a first chemical building block as described in Examples 1-3

(i.e. in liquid or on solid phase). The compound-oligonucleotide conjugates were then purified and individually ligated with an encoding oligonucleotide, by the help of a RNA/DNA adaptor oligonucleotide, as described in Examples 1-3. The adaptor molecules were then removed by either pH-based cleavage or RNAse H addition, optionally followed by a purification step, described in Examples 1-3. The obtained encoded compound-oligonucleotide conjugates were pooled in equimolar amounts and then split into a set of b vials, for the modification with b building block 2 (BB2) compounds.

The couplings were performed either in solution or while the DNA was attached to a solid support, as described in Examples 1-3. The b pools of compound-oligonucleotide conjugates were then individually ligated with an encoding oligonucleotide, by the help of a RNA/DNA adaptor oligonucleotide, as described in Examples 1-3. The adaptor molecules were then removed by either pH-based cleavage or RNAse H addition, optionally followed by a purification step, described in Examples 1-3. The obtained set of encoded compound-oligonucleotide conjugates were pooled in equimolar amounts and then split into a set of c vials, for the modification with c building block 3 (BB3) compounds. The couplings were performed either in solution or while the DNA was attached to a solid support, as described in Examples 1-3. The b pools of compound-oligonucleotide conjugates were then individually ligated with an encoding oligonucleotide, by the help of a RNA/DNA adaptor oligonucleotide, as described in Examples 1-3. The adaptor molecules were then removed by either pH-based cleavage or RNAse H addition, optionally followed by a purification step, described in Examples 1-3. The obtained set of encoded compound-oligonucleotide conjugates carrying sets of 3 encoded building blocks were either submitted to further rounds of for the modification with further sets of building blocks followed by encoding or mixed together to the desired sub-library. Optionally, using a suitable DNA polymerase the sub-library was converted into a double stranded DNA-encoded chemical library, which could optionally be stored or directly used for target-based selections.

Figure 3B:
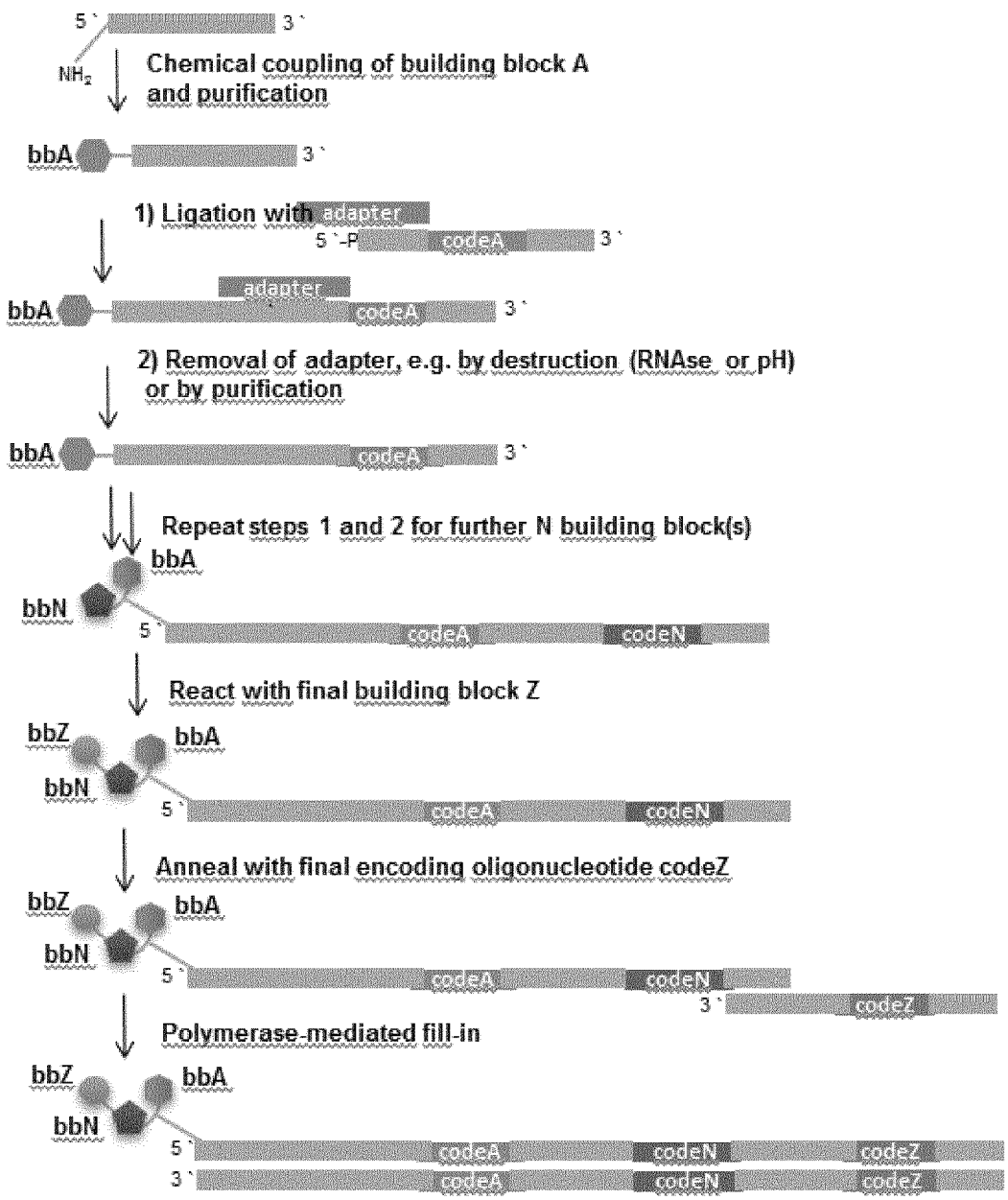

Example 12: Preparation of a DNA-Encoded Library [(FIG. 3B)]

5'-Amino-modified oligonucleotides were modified with a first chemical building block as described in Examples 1-3 (i.e. in liquid or on solid phase). The compound-oligonucleotide conjugates were then purified and individually ligated with an encoding oligonucleotide, by the help of a RNA/DNA adaptor oligonucleotide, as described in Examples 1-3. The adaptor molecules were then removed by either pH-based cleavage or RNAse H addition, optionally followed by a purification step, described in Examples 1-3. The obtained encoded compound-oligonucleotide conjugates were pooled in equimolar amounts and then split into a set of b vials, for the modification with b building block 2 (BB2) compounds. The couplings were performed either in solution or while the DNA was attached to a solid support, as described in Examples 1-3. The b pools of compound-oligonucleotide conjugates were then individually ligated with an encoding oligonucleotide, by the help of a RNA/DNA adaptor oligonucleotide, as described in Examples 1-3. The adaptor molecules were then removed either by pH-based cleavage or RNAse H cleavage, optionally followed by a purification step, described in Examples 1-3. The obtained sets of encoded compound-oligonucleotide conjugates were pooled in equimolar amounts and conjugation with further n sets of building blocks (n>1) was performed as described before. The ultimate encoding step was not performed by ligation but by polymerase-mediated fill-in. In this case, a fill-in reaction with an encoding oligonucleotide complementary to a sequence between the $(n-1)^{th}$ code and the 3' terminus of the compound-oligonucleotide conjugate strand was performed, as described in Examples 5 and 6, leading to a double-stranded DNA-encoded chemical library, which could optionally be stored or directly used for target-based selections.

Example 13: Affinity Screening of a DNA-Encoded Chemical Library Against a Target Protein of Interest Affinity selections were performed using a Thermo Scientific KingFisher magnetic particle processor. Streptavidin-coated magnetic beads (0.1 mg) were resuspended in 100 μl PBS (50 mM NaPi, 100 mM NaCl, pH 7.4) and subsequently incubated with 100 μl biotinylated target protein of interest (0.1 μM/1.0 μM concentration) for 30 min with continuous gentle mixing. target protein-coated beads were washed three times with 200 μl PBST (50 mM NaPi, 100 mM NaCl, 0.05% (v/v) Tween-20, pH 7.4) that was supplemented with 100 μM biotin in order to block remaining binding sites on Streptavidin, and subsequently incubated with 100 μl of the DNA-encoded chemical library (100 nM total concentration, in PBST) for 1 h with continuous gentle mixing. After removing unbound library members by washing with 200 μl PBST for five times, beads carrying bound library members were resuspended in 100 μl buffer EB (QIAGEN) and the DNA compound conjugates were separated from the beads by heat denaturation of Streptavidin and target protein (95° C. for 5 min).

REFERENCES

1 Mannocci, L. et al. *PNAS USA* 105(46):17670-17675
2 Brenner, S. and Lerner, R. A. *PNAS USA* 89 (1992), 5381-5383
3 Nielsen, J., et al., *J. Am. Chem. Soc.* 115 (1993)
4 Needels et al., M. C., *PNAS USA* 90 (1993), 10700-10704
5 Gartner, Z. J., et al., *Science* 305 (2004), 1601-1605
6 Melkko, S., et al., *Nat. Biotechnol.* 22 568-574 (2004)
7 Sprinz, K. I., et al., *Bioorg. Med. Chem. Lett.* 15 (2005), pp. 3908-3911
8 Leimbacher et al *Chemistry.* 2012 Jun. 18; 18(25):7729-37
9 Clark et al *Nat Chem Biol.* 2009 September; 5(9):647-54

TABLE 1

Adapter
5'-CGTC❋ATCCG❋CGCCAT❋GGACTCG-3'

Adapter G1
5'-CGA❋TCCCAT❋GCGCCC❋ATCGACG-3'

Adapter G2
5'-GCCTC❋AGGCGT❋ATCCTAC-3'
❋ RNA nucleotides

TABLE 2

Test Adapter
5'-CGACTCACATGGCGTACCTGC-3'
❋ RNA nucleotide

TABLE 2-continued

Test Ligation Product
5'-CCTGCATCGAATGGATCCGTGXXXXXXXXGCAGCTGCGCCATGG
GACTCGddddddCAGCACACAGAATTCAGAAGCTCC-3'

TABLE 3 lane 1
    Code 1 (45 nt)
5'-GGAGCTTCTGAATTCTGTGTGCTGXXXXXXCGAGTCCCATGGCGC-3' lane 2
    Code 2 5'P (27 nt)
5'-CGGATCGACGYYYYYYYGCCTCGAGGC-3' lane 3
    Adapter (25 nt)
3'-GCTCAGGGTACCGCGGCCTAGCTGC-5' lane 4 hybridization
    Code 1 (45 nt)
5'-GGAGCTTCTGAATTCTGTGTGCTGXXXXXXCGAGT NICK:    Code 2 5'P (27 nt)
CCCATGGCGCCGGATCGACGYYYYYYYGCCTCGAGGC-3'

3'-GCTCAGGGTACCGCGGCCTAGCTGC-5'
    Adapter (25 nt)

lane 5 ligation
    Code 1 + Code 2 (72 nt)
5'-GGAGCTTCTGAATTCTGTGTGCTGXXXXXXCGAGTCCCATGGCG
CCGGATCGACGYYYYYYYGCCTCGAGGC-3'

3'-GCTCAGGGTACCGCGGCCTAGCTGC-5'
    Adapter (25 nt)

lanes 6-9 purified ligation
    Code 1 + Code 2 (72 nt)
5'-GGAGCTTCTGAATTCTGTGTGCTGXXXXXXCGAGTCCCATGGCG
CCGGATCGACGYYYYYYYGCCTCGAGGC-3'

| lane 6 | QIA nucleotide removal kit | NaOH - |
| lane 7 | QIA nucleotide removal kit | NaOH + |
| lane 8 | QIA gel extraction kit | NaOh - |
| lane 9 | QIA gel extraction kit | NaOH + |

TABLE 4 lane 1
    Code 3' (31 nt)
3'-CACTAGGATGzzzzzzCGCGGTACCCTGAGC-5' lane 2
    d-spacer 2 (31 nt)
3'-CGCGGCCTAGCTGCdddddddCGGAGCTCCG-5' lane 3
    Adapter G2 (20 nt)
5'-GCCTCGAGGCGTGATCCTAC-3' lane 4 hybridication
    Adapter G2 (20 nt)
5'-GCCTCGAGGCGTGATCCTAC-3'

3'-CGCGGCCTAGCTGCddddddd
    d-spacer 2 (31 nt)

CGGAGCTCCGCACTAGGATGzzzzzzCGCGGTACCCTGAGC-5'
NICK: Code 3' (31 nt)

TABLE 4-continued lane 5 ligation
    Adapter G2 (20 nt)
5'-GCCTCGAGGCGTGATCCTAC-3'

3'-CGCGGCCTAGCTGCddddddd
    d-spacer 2 + Code 3' (62 nt)

CGGAGCTCCGCACTAGGATGzzzzzzCGCGGTACCCTGAGC-5' lanes 6-11 purified ligation
    d-spacer 2 + Code 3' (62 nt)
3'-CGCGGCCTAGCTGCddddddd
CGGAGCTCCGCACTAGGATGzzzzzzCGCGGTACCCTGAGC-5'

| lane 6 | QIA PCR purification kit | NaOH - |
| lane 7 | QIA nucleotide removal kit | NaOH - |
| lane 8 | QIA gel extr kit with isopropanol | NaOH - |
| lane 9 | QIA gel extr kit no isopropanol | NaOH - |
| lane 10 | MN NTI | NaOH - |
| lane 11 | MN NTC | NaOH - |

TABLE 5

Step 1: Ligate Code 1 + Code 2 (T4 DNA Ligase)
    Code 1 (45 nt)
5'-GGAGCTTCTGAATTCTGTGTGCTGXXXXXXCGAGTCCCATGGCGC-3'

Code 2 5'P (27 nt)
5'-CGGATCGACGYYYYYYYGCCTCGAGGC-3'

3'-GCTCAGGGTACCGCGGCCTAGCTGC-5'
    Adapter (25 nt)

Code 1 + Code 2 (72 nt)
5'-GGAGCTTCTGAATTCTGTGTGCTGXXXXXXCGAGTCCCATGGCGCCGG
ATCGACGYYYYYYYGCCTCGAGGC-3'

3'-GCTCAGGGTACCGCGGCCTAGCTGC-5'
    Adapter (25 nt)

Step 2: Disintegration of chimeric Adapter by NaOH treatment

Step 3: Purification using spin columns
    Code 1 + Code 2 (72 nt)
5'-GGAGCTTCTGAATTCTGTGTGCTGXXXXXXCGAGTCCCATGGCGCCGG
ATCGACGYYYYYYYGCCTCGAGGC-3'

| XXXXXX | 6 variable nucleotides of Code 1 |
| YYYYYYY | 7 variable nucleotides of Code 2 |
| zzzzzz | 6 complementary variable nucleotides of Code 3 |
| ZZZZZZ | 6 variable nucleotides of Code 3 |
| dddddd | abasic nucleotide backbone |
| P | phophate |
| nt | nucleotides |

TABLE 6

Step 1: Ligate Elib4.aT + d-spacer 2
(T4 DNA Ligase)
    Adapter G1 (25 nt)
5'-CGAGTCCCATGGCGCCGGATCGACG-3'

TABLE 6-continued

```
3'-CCTCGAAGACTTAAGACACACGACddddddGCTCAGGGTAC-5'
   Elib4.aT (41 nt)

3'-CGCGGCCTAGCTGCdddddddCGGAGCTCCG-5'
   d-spacer 2 (31 nt)

Adapter G1 (25 nt)
5'-CGAGTCCCATGGCGCCGGATCGACG-3'

3'-CCTCGAAGACTTAAGACACACGACddddddGCTCAGGGTACCGCGGCC
   Elib4.aT + d-spacer 2 (72 nt)

TAGCTGCdddddddCGGAGCTCCG-5'

Step 2: Disintegration of chimeric Adapter by
NaOH treatment

Step 3: Purification using spin columns

3'-CCTCGAAGACTTAAGACACACGACddddddGCTCAGGGTACCGCGGCC
   Elib4.aT + d-spacer 2 (72 nt)

TAGCTGCdddddddCGGAGCTCCG-5'

Step 4: Ligate Elib4.aT/d-spacer 2 + Code 3'
(T4 DNA Ligase)
   Adapter G2 (20 nt)
5'-GCCTCGAGGCGTGATCCTAC-3'

3'-CCTCGAAGACTTAAGACACACGACddddddGCTCAGGGTACCGCGGCC
   Elib4.aT + d-spacer 2 (72 nt)

TAGCTGCdddddddCGGAGCTCCG-5'

3'-CACTAGGATGzzzzzzCGCGGTACCCTGAGC-5'
   Code 3' (31 nt)

Adapter G2 (20 nt)
5'-GCCTCGAGGCGTGATCCTAC-3'

3'-CCTCGAAGACTTAAGACACACGACddddddGCTCAGGGTACCGCGGCC
   Elib4.at + d-spacer 2 + Code 3' (103 nt)

TAGCTGCdddddddCGGAGCTCCGCACTAGGATGzzzzzzCGCGGTACCCT

GAGC-5'

Step 5: Disintegration of chimeric Adapter by
NaOH treatment

Step 6: Purification using spin columns

3'-CCTCGAAGACTTAAGACACACGACddddddGCTCAGGGTACCGCGGCC
   Elib4 intermediate library + d-spacer 2 +
   Code 3' (103 nt)

TAGCTGCdddddddCGGAGCTCCGCACTAGGATGzzzzzzCGCGGTACCCT

GAGC-5'
```

TABLE 7

```
Step 1: Hybridization of Sub-Libraries
   Code 1 + Code 2 (72 nt)
5'-GGAGCTTCTGAATTCTGTGTGCTGXXXXXXCGAGTCCCATGGCG

CCGGATCGACGYYYYYYYYGCCTCGAGGC-3'

3'-CCTCGAAGACTTAAGACACACGACddddddGCTCAGGGTACCGC
   Elib4.aT + d-spacer 2 + Code 3' (103 nt)

GGCCTAGCTGCdddddddCGGAGCTCCGCACTAGGATGzzzzzzCGC

GGTACCCTGAGC-5' step 2: Klenow Polymerase fill-in
   Code 1 + Code 2 (72 nt)
5'-GGAGCTTCTGAATTCTGTGTGCTGXXXXXXCGAGTCCCATGGCG

CCGGATCGACGYYYYYYYYGCCTCGAGGC-3'  --->

3'-CCTCGAAGACTTAAGACACACGACddddddGCTCAGGGTACCGC
   Elib4.aT + d-spacer 2 + Code 3' (103 nt)

GGCCTAGCTGCdddddddCGGAGCTCCGCACTAGGATGzzzzzzCGC

GGTACCCTGAGC-5'

Code 1 + Code 2 + Code 3 (103 nt)
5'-GGAGCTTCTGAATTCTGTGTGCTGXXXXXXCGAGTCCCATGGCG

CCGGATCGACGYYYYYYYYGCCTCGAGGCGTGATCCTACZZZZZZGCG

CCATGGGACTCG-3'

3'-CCTCGAAGACTTAAGACACACGACddddddGCTCAGGGTACCGC
   Elib4.aT + d-spacer 2 + Code 3' (103 nt)

GGCCTAGCTGCdddddddCGGAGCTCCGCACTAGGATGzzzzzzCGC

GGTACCCTGAGC-5'

Final library. Ready to use.
```

---

The invention claimed is:

1. A method of producing a nucleic acid encoded chemical library comprising;
   (i) producing a sub-library according to a method comprising;
      (a) providing a population of first nucleic acid strands, each nucleic acid strand being coupled or couplable to a member of a first diverse population of chemical moieties and comprising a non-hybridisable spacer,
      (b) contacting the first nucleic acid strands with identifier oligonucleotides comprising a first coding sequence and one or more adaptor oligonucleotides, such that the one or more adaptor oligonucleotides hybridize to the nucleic acid strands and the identifier oligonucleotides to form a partially double-stranded complex,
      wherein each first nucleic acid strand is contacted with an identifier oligonucleotide comprising a first coding sequence that encodes a chemical moiety that is coupled or couplable to the first nucleic acid strand, and;

wherein each of said one or more adaptor oligonucleotides hybridizes to more than one first nucleic acid strand in the population and more than one different identifier oligonucleotide, (c) ligating the first nucleic acid strands to the identifier oligonucleotides in the partially double-stranded complexes, such that the identifier oligonucleotides are incorporated into the first nucleic acid strands, thereby producing a sub-library comprising first nucleic acid strands coupled or couplable to a member of a diverse population of chemical moieties, wherein each first nucleic acid strand comprises a first coding sequence that encodes the chemical moiety that is coupled to the first nucleic acid strand and the non-hybridisable spacer;

(ii) hybridizing the first nucleic acid strands to second nucleic acid strands to form double-stranded complexes, wherein the second nucleic acid strands are coupled to a second diverse population of chemical moieties, each second nucleic acid strand comprising a second coding sequence that encodes the chemical moiety that is coupled to it, the position of the second coding sequence in the second nucleic acid strands corresponding in the double-stranded complex to the position of the spacer in the first nucleic acid strands in the double-stranded complexes, such that the second coding sequences do not preferentially hybridise to the first nucleic acid strands, and (iii) extending the second nucleic acid strands along the nucleic acid strands to produce a library comprising members having a double strand nucleic acid molecule comprising the first and second nucleic acid strands;

the first diverse population of chemical moieties being coupled to the first nucleic acid strands and the second diverse population of chemical moieties being coupled to the second nucleic acid strands, said chemical moieties form pharmacophores in the library members, wherein each second nucleic acid strand comprises first and second coding sequences that encode the chemical moieties from the first and second diverse populations.

2. A method according to claim 1 wherein the adaptor oligonucleotide is removed after the ligation by cleaving said adaptor oligonucleotide.

3. A method according to claim 2 wherein the adaptor oligonucleotide comprises one or more ribonucleotide bases.

4. A method according to claim 1 wherein the spacer comprises an abasic linker.

5. A method according to claim 4 wherein the abasic linker is an abasic deoxyribose phosphate linker.

6. A method of producing a nucleic acid encoded chemical library comprising;

(i) providing a sub-library of first nucleic acid strands coupled to first and second diverse populations of chemical moieties ("first and second chemical moieties"), wherein each first nucleic acid strand comprises a first coding sequence which encodes the member of the first diverse population of chemical moieties that is coupled to the first nucleic acid strand, (ii) contacting the first nucleic acid strands with an adaptor oligonucleotide and first identifier oligonucleotides comprising coding sequences, such that the adaptor oligonucleotide hybridizes to the first nucleic acid strands and the first identifier oligonucleotides to form partially double-stranded complexes, wherein each first nucleic acid strand is contacted with a first identifier oligonucleotide comprising a coding sequence which encodes the member of the second population of chemical moieties that is coupled to the first nucleic acid strand, and;

wherein all the first nucleic acid strands in the sub-library are contacted with the same adaptor oligonucleotide, (iii) ligating the first nucleic acid strands to the first identifier oligonucleotides in the complexes, such that the second coding sequences are incorporated into the first nucleic acid strands;

(iv) contacting the first nucleic acid strands with a nucleic acid spacer strand, second identifier oligonucleotides, and a sub-library of second nucleic acid strands coupled to a third diverse population of chemical moieties ("third chemical moieties"), thereby forming partially double-stranded complexes, wherein each first nucleic acid strand is contacted with a second identifier oligonucleotide comprising a third coding sequence that encodes the member of the third population of chemical moieties that is coupled to the second nucleic acid strand, and;

wherein all the nucleic acid strands in the population are contacted with the same nucleic acid spacer strand, (v) ligating the first nucleic acid strand to the second identifier oligonucleotide such that the third coding sequence is incorporated into the nucleic acid strand; and, (vi) optionally ligating the second nucleic acid strand to the nucleic acid spacer strand, wherein the nucleic acid spacer strand comprises;
a) a first hybridization portion which hybridizes to the first nucleic acid strand,
b) a non-hybridizable spacer at a position that corresponds, when the first nucleic acid strand and the nucleic acid spacer strand are hybridised together, to the position of the second coding sequence in the first nucleic acid strand
c) a second hybridization portion which hybridizes to the first nucleic acid strand; and,
d) a complementary annealing region which hybridizes to the second identifier oligonucleotide; and wherein the second nucleic acid strand comprises;
a) a first hybridization portion which hybridizes to the first nucleic acid strand,
b) a non-hybridizable spacer at a position that corresponds, when the first and second strands are hybridised together, to the position of the first coding sequence in the first nucleic acid strand; and
c) a second hybridization portion which hybridizes to the first nucleic acid strand thereby producing a library comprising pharmacophores labelled with double-stranded nucleic acid molecules comprising first and second nucleic acid strands.

7. A method according to claim 6 wherein the adaptor oligonucleotide is removed after the ligation by cleaving said adaptor oligonucleotide.

8. A method according to claim 7 wherein the adaptor oligonucleotide comprises one or more ribonucleotide bases.

9. A method according to claim 6 wherein the spacer comprises an abasic linker.

10. A method according to claim 9 wherein the abasic linker is an abasic deoxyribose phosphate linker.

11. A method of producing a nucleic acid encoded chemical library comprising;
  (i) providing a sub-library of first nucleic acid strands coupled to first and second diverse populations of chemical moieties ("first and second chemical moieties"),
    wherein each first nucleic acid strand comprises a first coding sequence which encodes the member of the first diverse population of chemical moieties that is coupled to the first nucleic acid strand,
  (ii) contacting the first nucleic acid strands with an adaptor oligonucleotide and first identifier oligonucleotides comprising coding sequences, such that the adaptor oligonucleotide hybridizes to the first nucleic acid strands and the first identifier oligonucleotides to form partially double-stranded complexes,
    wherein each first nucleic acid strand is contacted with a first identifier oligonucleotide comprising a coding sequence which encodes the member of the second population of chemical moieties that is coupled to the first nucleic acid strand, and;
    wherein all the first nucleic acid strands in the sub-library are contacted with the same adaptor oligonucleotide,
  (iii) ligating the first nucleic acid strands to the first identifier oligonucleotides in the complexes, such that the second coding sequences are incorporated into the first nucleic acid strands;
  (iv) contacting the first nucleic acid strands with one or more nucleic acid spacer strands, second identifier oligonucleotides, and a sub-library of second nucleic acid strands coupled to a third diverse population of chemical moieties ("third chemical moieties"), thereby forming partially double-stranded complexes,
    wherein each first nucleic acid strand is contacted with a second identifier oligonucleotide comprising a third coding sequence that encodes the member of the third population of chemical moieties that is coupled to the second nucleic acid strand, and
    wherein the second nucleic acid strands, nucleic spacer strand and second identifier oligonucleotides hybridise to the first nucleic acid strand to form a double-stranded complex having a 5' overhang comprising the third coding sequence;
    wherein each spacer strand hybridizes to more than one first nucleic acid strand in the population and more than one different second identifier oligonucleotide,
  (v) extending the first nucleic acid strand along the second identifier oligonucleotide to incorporate the complement of the third coding sequence into the first nucleic acid strand; and,
  (vi) optionally ligating the second nucleic acid strands to the nucleic acid spacer strands and the second identifier oligonucleotides,
  thereby producing a library comprising pharmacophores labelled with double-stranded nucleic acid molecules comprising first and second nucleic acid strands,
    wherein the nucleic acid spacer strand comprises;
    a) a first hybridization portion which hybridizes to the first nucleic acid strand,
    b) a non-hybridizable spacer at a position that corresponds, when the first nucleic acid strand and the nucleic acid spacer strand are hybridised together, to the position of the second coding sequence in the first nucleic acid strand
    c) a second hybridization portion which hybridizes to the first nucleic acid strand; and
    wherein the second nucleic acid strand comprises;
    a) a first hybridization portion which hybridizes to the first nucleic acid strand,
    b) a non-hybridizable spacer at a position that corresponds, when the first and second strands are hybridised together, to the position of the first coding sequence in the first nucleic acid strand; and
    c) a second hybridization portion which hybridizes to the first nucleic acid strand.

12. A method according to claim 11 wherein the adaptor oligonucleotide is removed after the ligation by cleaving said adaptor oligonucleotide.

13. A method according to claim 12 wherein the adaptor oligonucleotide comprises one or more ribonucleotide bases.

14. A method according to claim 11 wherein the spacer comprises an abasic linker.

15. A method according to claim 14 wherein the abasic linker is an abasic deoxyribose phosphate linker.

16. A method of producing a nucleic acid encoded chemical library comprising;
  (i) providing a sub-library of first nucleic acid strands coupled to first and second diverse populations of chemical moieties ("first and second chemical moieties"),
    wherein each first nucleic acid strand comprises a first coding sequence which encodes the member of the first diverse population of chemical moieties that is coupled to the first nucleic acid strand,
  (ii) contacting the first nucleic acid strands with an adaptor oligonucleotide and first identifier oligonucleotides comprising coding sequences, such that the adaptor oligonucleotide hybridizes to the first nucleic acid strands and the first identifier oligonucleotides to form partially double-stranded complexes,
    wherein each first nucleic acid strand is contacted with a first identifier oligonucleotide comprising a coding sequence which encodes the member of the second population of chemical moieties that is coupled to the first nucleic acid strand, and;
    wherein all the first nucleic acid strands in the sub-library are contacted with the same adaptor oligonucleotide,
  (iii) ligating the first nucleic acid strands to the first identifier oligonucleotides in the complexes, such that the second coding sequences are incorporated into the first nucleic acid strands;
  (iv) contacting the first nucleic acid strands with a sub-library of second nucleic acid strands coupled to a third diverse population of chemical moieties ("third chemical moieties"), thereby forming partially double-stranded complexes,
    wherein each second nucleic acid strand comprises first and second non-hybridizable spacer regions at positions corresponding to the first and second coding sequences in the first nucleic acid strand and a third coding sequence that encodes the member of the third population of chemical moieties that is coupled to the second nucleic acid strand, and
    wherein the second nucleic acid strands hybridise to the first nucleic acid strand to form a double-stranded complex having a 5' overhang comprising the third coding sequence;
  (v) extending the first nucleic acid strand along the second nucleic acid strand to incorporate the complement of the third coding sequence into the first nucleic acid strand;

thereby producing a library comprising pharmacophores labelled with double-stranded nucleic acid molecules comprising first and second nucleic acid strands.

17. A method according to claim 16 wherein the sub-library of second nucleic acid strands is produced by a method comprising;
    (a) providing a second nucleic acid strand having a third chemical moiety coupled thereto,
    wherein the second nucleic acid strand comprises a first non-hybridizable spacer region at a position corresponding to the first coding sequence in the first nucleic acid strand,
    (b) contacting the second nucleic acid strand with an adaptor oligonucleotide and a nucleic acid spacer strand comprising a second non-hybridizable spacer region at a position corresponding to the second coding sequence in the first nucleic acid strand,
    such that the adaptor oligonucleotide hybridizes to the second nucleic acid strand and the nucleic acid spacer strand to form a partially double-stranded complex,
    (c) ligating the second nucleic acid strand to the nucleic acid spacer strand in the complex, such that the second non-hybridizable spacer region is incorporated into the second nucleic acid strand;
    (d) contacting the second nucleic acid strand with an adaptor oligonucleotide and a second identifier oligonucleotide comprising a third coding sequence that encodes the third chemical moiety,
    such that the adaptor oligonucleotide hybridizes to the second nucleic acid strand and the second identifier oligonucleotide to form a partially double-stranded complex,
    (e) ligating the second nucleic acid strand to the second identifier oligonucleotide in the complex, such that the third coding sequence is incorporated into the second nucleic acid strand;
    (f) repeating steps (a) to (e) in series or in parallel using different third chemical moieties and third coding sequences and the same adaptor oligonucleotide to produce a diverse population of third chemical moieties coupled to second nucleic acid strands,
    each third chemical moiety being coupled to a second nucleic acid strand which comprises first and second spacer regions and a third coding sequence encoding the third chemical moiety coupled thereto.

18. A method according to claim 16 wherein the adaptor oligonucleotide is removed after the ligation by cleaving said adaptor oligonucleotide.

19. A method according to claim 18 wherein the adaptor oligonucleotide comprises one or more ribonucleotide bases.

20. A method according to claim 16 wherein the spacer region comprises an abasic linker.

21. A method according to claim 20 wherein the abasic linker is an abasic deoxyribose phosphate linker.

22. A method of producing a nucleic acid encoded chemical library comprising;
    (i) providing a sub-library of first nucleic acid strands coupled to first and second diverse populations of chemical moieties ("first and second chemical moieties"),
    wherein each first nucleic acid strand comprises a first coding sequence which encodes the member of the first diverse population of chemical moieties that is coupled to the first nucleic acid strand,
    (ii) contacting the first nucleic acid strands with one or more nucleic acid spacer strands and first identifier oligonucleotides comprising coding sequences, such that the first nucleic acid spacer strand hybridizes to the first nucleic acid strands and the first identifier oligonucleotides to form partially double-stranded complexes,
    wherein each first nucleic acid strand is contacted with a first identifier oligonucleotide comprising a second coding sequence which encodes the member of the second population of chemical moieties that is coupled to the first nucleic acid strand, and;
    wherein each nucleic acid spacer strand hybridizes to more than one first nucleic acid strand in the population and more than one different first identifier oligonucleotide,
    (iii) ligating the first nucleic acid strands to the first identifier oligonucleotides in the complexes, such that the second coding sequences are incorporated into the first nucleic acid strands;
    (iv) contacting the first nucleic acid strands hybridised to the nucleic acid spacer strand with a sub-library of second nucleic acid strands coupled to a third diverse population of chemical moieties ("third chemical moieties") and second identifier oligonucleotides, thereby forming double-stranded complexes,
    wherein each first nucleic acid strand is contacted with a second identifier oligonucleotide that comprises a third coding sequence that encodes the member of the third population of chemical moieties that is coupled to the second nucleic acid strand that is contacted therewith, and;
    (v) ligating the first nucleic acid strand to the second identifier oligonucleotide such that the third coding sequence is incorporated into the nucleic acid strand; and,
    (vi) optionally ligating the second nucleic acid strand to the nucleic acid spacer strand,
    wherein the nucleic acid spacer strand comprises;
    a) a first hybridization portion which hybridizes to the first nucleic acid strand,
    b) a first non-hybridizable spacer at a position that corresponds, when the first nucleic acid strand and the nucleic acid spacer strand are hybridised together, to the position of the second coding sequence in the first nucleic acid strand,
    c) a second hybridization portion which hybridizes to the first nucleic acid strand;
    d) a first annealing region which hybridizes to the second identifier oligonucleotide,
    e) a second non-hybridizable spacer at a position that corresponds, when the second identifier oligonucleotide and the nucleic acid spacer strand are hybridised together, to the position of the third coding sequence in the second identifier oligonucleotide and;
    f) a second annealing region which hybridizes to the second identifier oligonucleotide; and
    wherein the second nucleic acid strand comprises;
    a) a first hybridization portion which hybridizes to the first nucleic acid strand,
    b) a non-hybridizable spacer at a position that corresponds, when the first and second strands are hybridised together, to the position of the first coding sequence in the first nucleic acid strand; and
    c) a second hybridization portion which hybridizes to the first nucleic acid strand
    thereby producing a library comprising pharmacophores labelled with double-stranded nucleic acid molecules comprising first and second nucleic acid strands.

23. A method according to claim 22 wherein the spacer comprises an abasic linker.

24. A method according to claim 23 wherein the abasic linker is an abasic deoxyribose phosphate linker.

25. A method of producing a nucleic acid encoded chemical library according comprising;
   (i) providing a sub-library of first nucleic acid strands coupled to first and second diverse populations of chemical moieties ("first and second chemical moieties"),
   wherein each first nucleic acid strand comprises a first coding sequence which encodes the member of the first diverse population of chemical moieties that is coupled to the first nucleic acid strand,
   (ii) contacting the first nucleic acid strands with one or more nucleic acid spacer strands and first identifier oligonucleotides comprising coding sequences, such that the first nucleic acid spacer strand hybridizes to the first nucleic acid strands and the first identifier oligonucleotides to form partially double-stranded complexes,
   wherein each first nucleic acid strand is contacted with a first identifier oligonucleotide comprising a second coding sequence which encodes the member of the second population of chemical moieties that is coupled to the first nucleic acid strand, and;
   wherein each nucleic acid spacer strand hybridizes to more than one first nucleic acid strand in the population and more than one different first identifier oligonucleotide,
   (iii) ligating the first nucleic acid strands to the first identifier oligonucleotides in the complexes, such that the second coding sequences are incorporated into the first nucleic acid strands;
   (iv) contacting the first nucleic acid strands with a sub-library of second nucleic acid strands coupled to a third diverse population of chemical moieties ("third chemical moieties"), thereby forming double-stranded complexes,
   wherein each first nucleic acid strand is contacted with a second nucleic acid strand comprising a third coding sequence that encodes the member of the third population of chemical moieties that is coupled to the second nucleic acid strand, and the double-stranded complexes have a 5' overhang comprising the third coding sequence,
   (v) extending the first nucleic acid strand along the second nucleic acid strand to incorporate the complement of the third coding sequence into the first nucleic acid strand; and,
   wherein the second nucleic acid strand comprises;
   a) a first hybridization portion which hybridizes to the first nucleic acid strand,
   b) non-hybridizable spacers at positions that correspond, when the first and second strands are hybridised together, to the position of the first and second coding sequences in the first nucleic acid strand; and
   c) a second hybridization portion which hybridizes to the first nucleic acid strand;
   thereby producing a library comprising pharmacophores labelled with double-stranded nucleic acid molecules comprising first and second nucleic acid strands.

26. A method according to claim 25 wherein the spacer comprises an abasic linker.

27. A method according to claim 26 wherein the abasic linker is an abasic deoxyribose phosphate linker.

* * * * *